United States Patent
Kido

(10) Patent No.: US 10,646,166 B2
(45) Date of Patent: May 12, 2020

(54) PERSONAL GENOME INFORMATION ENVIRONMENT PROVIDING DEVICE, PERSONAL GENOME INFORMATION ENVIRONMENT PROVIDING METHOD, AND COMPUTER PROGRAM PRODUCT

(71) Applicant: National Institute of Japan Science and Technology Agency, Kawaguchi-shi, Saitama (JP)

(72) Inventor: Takashi Kido, Tokyo (JP)

(73) Assignee: National Institute of Japan Science and Technology Agency, Kawaguchi-shi, Saitama (JP)

( * ) Notice: Subject to any disclaimer, the term of this patent is extended or adjusted under 35 U.S.C. 154(b) by 1522 days.

(21) Appl. No.: 14/386,457

(22) PCT Filed: Mar. 22, 2013

(86) PCT No.: PCT/JP2013/058433
§ 371 (c)(1),
(2) Date: Sep. 19, 2014

(87) PCT Pub. No.: WO2013/141386
PCT Pub. Date: Sep. 26, 2013

(65) Prior Publication Data
US 2015/0051451 A1    Feb. 19, 2015

(30) Foreign Application Priority Data
Mar. 23, 2012    (JP) .................................. 2012-067762

(51) Int. Cl.
*A61B 5/113*    (2006.01)
*A61B 5/08*    (2006.01)
(Continued)

(52) U.S. Cl.
CPC .............. *A61B 5/7275* (2013.01); *A61B 5/00* (2013.01); *A61B 5/0205* (2013.01);
(Continued)

(58) Field of Classification Search
CPC .......... G06F 19/18; G06F 19/28; G06F 17/30; G06F 19/30; G06F 19/32; G06F 19/321;
(Continued)

(56) References Cited

U.S. PATENT DOCUMENTS

| 2004/0122706 A1 | 6/2004 | Walker et al. |
| 2006/0173663 A1 | 8/2006 | Langheier et al. |

(Continued)

FOREIGN PATENT DOCUMENTS

| JP | 2008-532104 A | 8/2008 |
| JP | 2011-134106 A | 7/2011 |
| WO | 2010/146811 A1 | 12/2010 |

OTHER PUBLICATIONS

European Patent Office, "Extended European Search Report," issued in European Patent Application No. 13 763 802.9, which is a European counterpart of U.S. Appl. No. 14/386,457, dated Jul. 30, 2015, 7 pages.

(Continued)

*Primary Examiner* — Maroun P Kanaan
(74) *Attorney, Agent, or Firm* — Amster, Rothstein & Ebenstein LLP

(57) ABSTRACT

The present invention acquires self-tracking information obtained by integrating habit information and biological signal information. Based on personal genome information and the acquired self-tracking information, characteristic information about characteristics of a user is acquired, and the acquired characteristic information is output.

17 Claims, 43 Drawing Sheets

(51) Int. Cl.
| | |
|---|---|
| *A61B 5/00* | (2006.01) |
| *G16B 20/00* | (2019.01) |
| *G16B 50/00* | (2019.01) |
| *G06Q 50/22* | (2018.01) |
| *G06Q 10/04* | (2012.01) |
| *A61B 5/0205* | (2006.01) |
| *A61B 5/0476* | (2006.01) |
| *A61B 5/11* | (2006.01) |
| *A61B 5/145* | (2006.01) |
| *A61B 5/16* | (2006.01) |
| *A61B 5/024* | (2006.01) |

(52) U.S. Cl.
CPC .......... *A61B 5/0476* (2013.01); *A61B 5/1118* (2013.01); *A61B 5/14532* (2013.01); *A61B 5/167* (2013.01); *A61B 5/4812* (2013.01); *G06Q 10/04* (2013.01); *G06Q 50/22* (2013.01); *G16B 20/00* (2019.02); *G16B 50/00* (2019.02); *A61B 5/024* (2013.01)

(58) Field of Classification Search
CPC .... G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06F 16/9535; A61B 5/00; A61B 5/0205; A61B 5/024; A61B 5/1118; A61B 5/167; A61B 5/4812; A61B 5/7275; G06Q 50/22; G06Q 10/10; G06Q 40/08; G06Q 50/24; A61N 1/08; G16H 10/10; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/14; G16H 70/60; G16H 80/00; G16B 20/00; G16B 50/00

See application file for complete search history.

(56) References Cited

U.S. PATENT DOCUMENTS

| | | | | |
|---|---|---|---|---|
| 2008/0269625 | A1* | 10/2008 | Halperin | A61B 5/113 600/508 |
| 2009/0112114 | A1* | 4/2009 | Ayyagari | A61B 5/08 600/529 |
| 2012/0041778 | A1* | 2/2012 | Kraft | G06F 19/00 705/2 |

OTHER PUBLICATIONS

Takashi Kido, "Self-Tracking Mindfulness Incorporating a Personal Genome", AAAI Technical Report SS-12-05, Self-Tracking and Collective Intelligence for Personal Wellness, pp. 31-36 (2012), Association for the Advancement of Artificial Intelligence.
International Search Report issued for PCT Patent Application No. PCT/JP2013/058433 dated Jul. 30, 2013, 2 pages.
Written Opinion of the International Searching Authority issued for PCT Patent Application No. PCT/JP2013/058433, dated Jul. 30, 2013, 4 pages.
Takashi Kido, "Genetics and Artificial Intelligence for Personal Genome Service—MyFinder: Intimate Community Computing for Scientific Discovery", papers from the AAAI 2011 Spring Symposium, pp. 8-11 (2011).
Pauline C. Ng et al., "An agenda for personalized medicine", Nature, vol. 461, pp. 724-726 (Oct. 8, 2009), Macmillan Publishers Limited.
23andMe, "Genetic Testing for Ancestry", [online] <https://www.23andme.com/>, retrieved Jul. 28, 2014.
PatientsLikeMe, "Live better, together!", [online] <https://www.patientslikeme.com/>, retrieved Jul. 28, 2014.
PharmGKB "The Pharmacogenomics Knowledge Base", [online] <https://www.pharmgkb.org/>, retrieved Jul. 28, 2014.
Folding@home, "Folding@home", [online] <http://folding.stanford.edu/>, retrieved Jul. 28, 2014.
Mihaly Csikszentmihalyi, Finding Flow: The Psychology of Engagement with Everyday Life, pp. 14-16, (1998), Basic Books.
European Patent Office, "Office Communication," issued in European Patent Application No. 13 763 802.9, which is a European counterpart of U.S. Appl. No. 14/386,457, dated Mar. 13, 2019, 9 pages.
European Patent Office, Office Communication, issued in European Patent Application No. 13 763 802.9, which is a European counterpart of U.S. Appl. No. 14/386,457, dated Dec. 17, 2018, 9 pages.

* cited by examiner

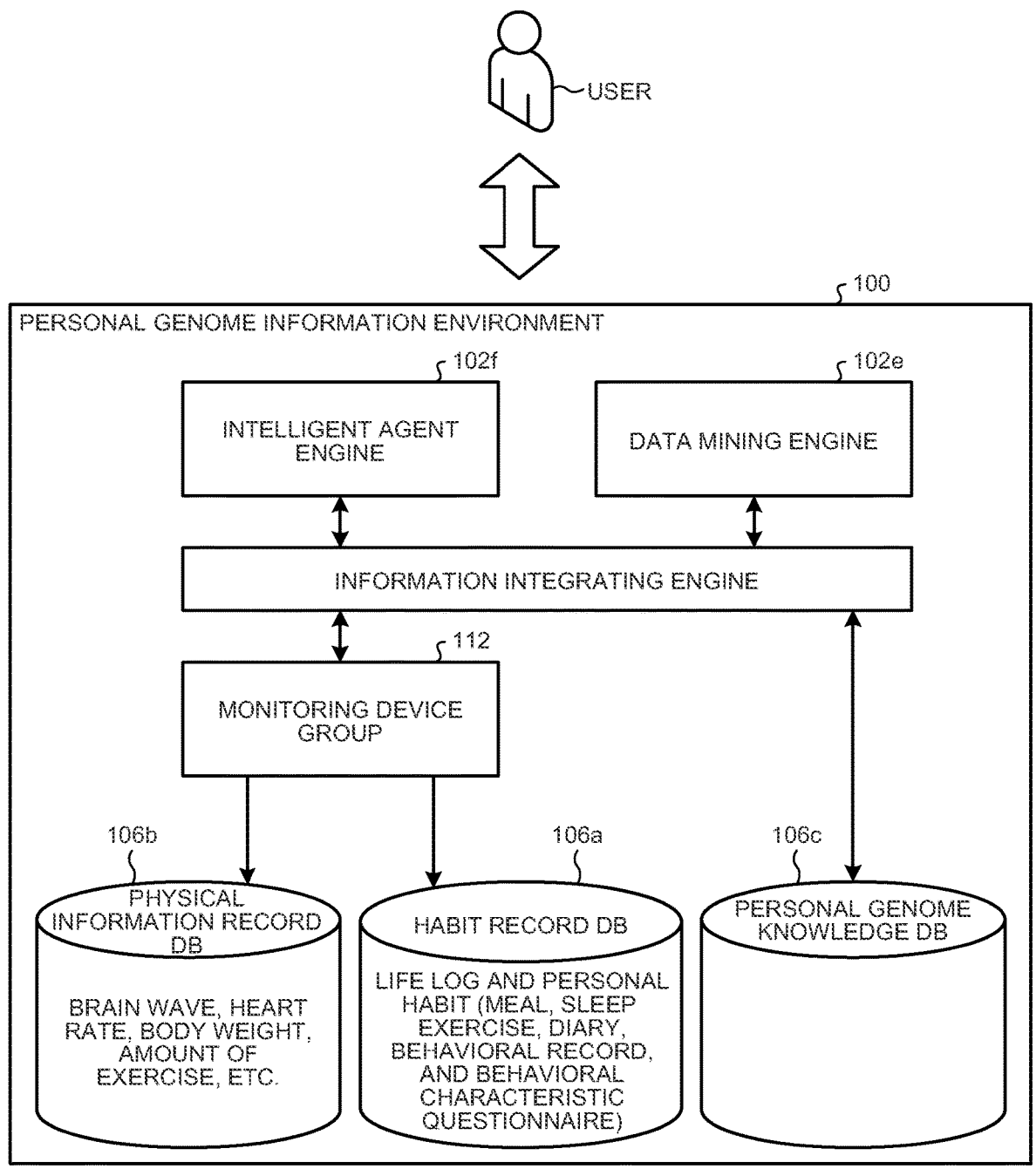

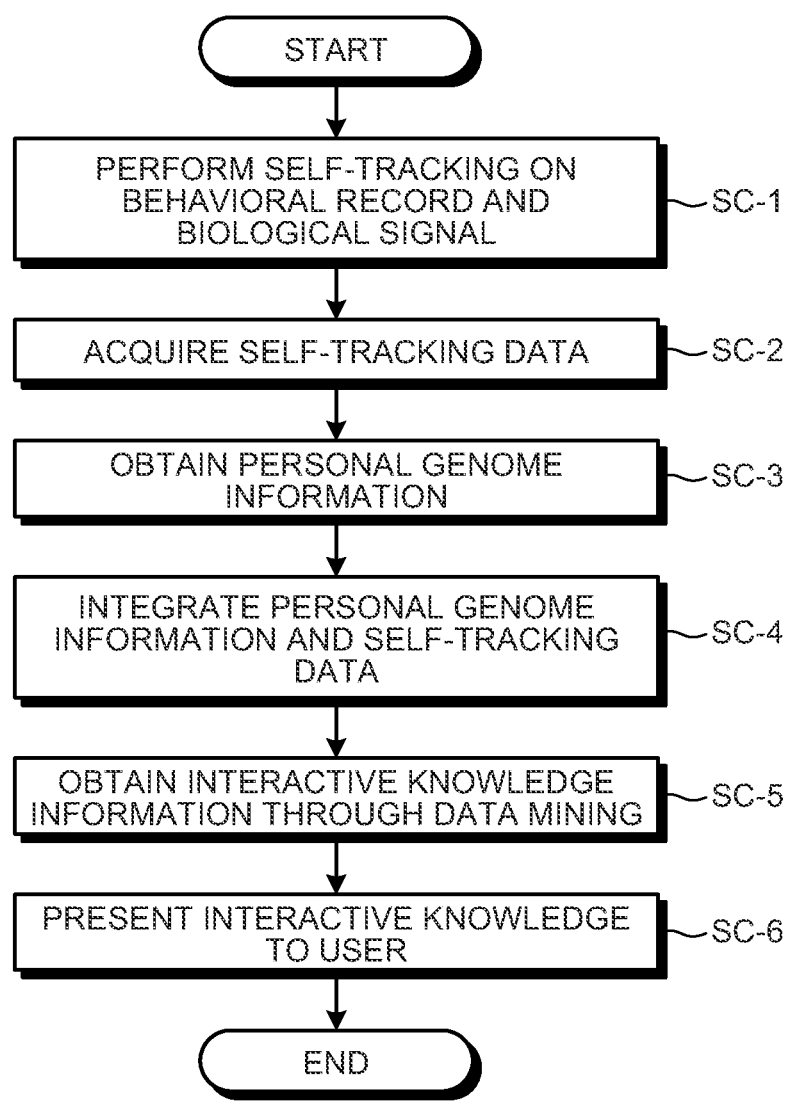

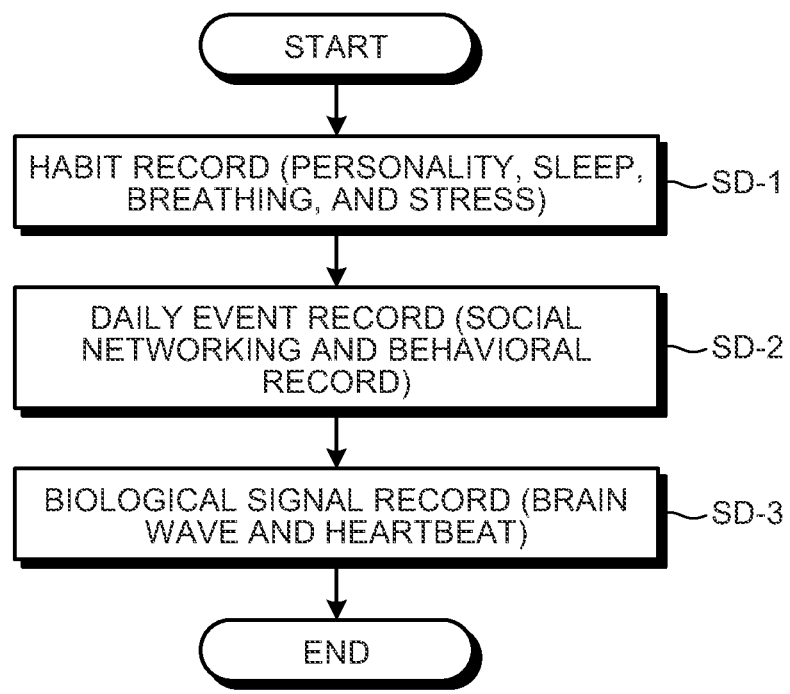

FIG.8

MORNINGNESS-EVENINGNESS QUESTIONNAIRE (MEQ)

YOUR NAME: _____ DATE OF REPLY: __ / __ /20

1. BEARING IN MIND ONLY LIFE RHYTHM THAT SEEMS TO GIVE YOU THE BEST PHYSICAL CONDITION, WHAT TIME WOULD YOU GET UP IF YOU WERE ENTIRELY FREE TO PLAN YOUR DAY? MARK THE APPLICABLE NUMBER ON THE TIME SCALE BELOW WITH O.

AM
5:00   6:00   7:00   8:00   9:00   10:00   11:00   12:00
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |

⬆ NUMBER

2. BEARING IN MIND ONLY LIFE RHYTHM THAT SEEMS TO GIVE YOU THE BEST PHYSICAL CONDITION, WHAT TIME WOULD YOU GO TO BED IF YOU WERE ENTIRELY FREE TO PLAN YOUR EVENING? MARK THE APPLICABLE NUMBER ON THE TIME SCALE BELOW WITH O.

PM                                      AM
8:00   9:00   10:00   11:00   12:00   1:00   2:00   3:00
| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 |

⬆ NUMBER

3. IF THERE IS SPECIFIC TIME AT WHICH YOU HAVE TO GET UP IN THE MORNING, TO WHAT EXTENT DO YOU DEPEND ON BEING WOKEN UP BY ALARM CLOCK?

☐ 1 NOT AT ALL DEPENDENT   ☐ 2 SLIGHTLY DEPENDENT   ☐ 3 FAIRLY DEPENDENT   ☐ 4 VERY DEPENDENT

4. HOW EASY DO YOU USUALLY FIND IT TO GET UP AFTER WAKING UP IN THE MORNING?

☐ 1 NOT AT ALL EASY (DIFFICULT)   ☐ 2 NOT VERY EASY
☐ 3 FAIRLY EASY                   ☐ 4 VERY EASY

5. HOW ALERT DO YOU USUALLY FEEL DURING THE FIRST 30 MINUTE AFTER YOU GET UP?

☐ 1 NOT AT ALL ALERT   ☐ 2 ONLY SLIGHTLY ALERT
☐ 3 FAIRLY ALERT       ☐ 4 VERY ALERT

6. HOW HUNGRY DO YOU USUALLY FEEL DURING THE FIRST 30 MINUTE AFTER YOU GET UP?

☐ 1 NOT AT ALL HUNGRY   ☐ 2 ONLY SLIGHTLY HUNGRY
☐ 3 FAIRLY HUNGRY       ☐ 4 VERY HUNGRY

FIG. 9

7. HOW TIRED DO YOU USUALLY FEEL DURING THE FIRST 30 MINUTES AFTER YOU GET UP?

☐ 1 VERY TIRED  ☐ 2 FAIRLY TIRED
☐ 3 FAIRLY REFRESHED  ☐ 4 VERY REFRESHED

8. IF YOU HAVE NO COMMITMENT THE NEXT DAY, WHAT TIME WOULD YOU GO TO BED COMPARED WITH YOUR USUAL BEDTIME?

☐ 1 SELDOM (OR NEVER) LATER  ☐ 2 LESS THAN ONE HOUR LATER
☐ 3 ONE TO TWO HOUR LATER  ☐ 4 MORE THAN TWO HOUR LATER

9. YOU HAVE DECIDED TO ENGAGE IN SOME PHYSICAL EXERCISE. FRIEND SUGGESTS THAT YOU DO THIS FOR ONE HOUR TWICE PER WEEK AND THE BEST TIME IS BETWEEN 7:00 AND 8:00 AM. BEARING IN MIND ONLY LIFE RHYTHM THAT SEEMS TO GIVE YOU THE BEST PHYSICAL CONDITION, HOW WELL DO YOU THINK YOU WOULD PERFORM?

☐ 1 WOULD PERFORM IT IN PERFECT FORM  ☐ 2 WOULD PERFORM IT IN REASONABLE FORM
☐ 3 WOULD FIND IT DIFFICULT  ☐ 4 WOULD FIND IT VERY DIFFICULT

10. AT WHAT TIME OF NIGHT DO YOU FEEL TIRED AND SLEEPY? MARK THE APPLICABLE NUMBER ON THE TIME SCALE BELOW WITH O.

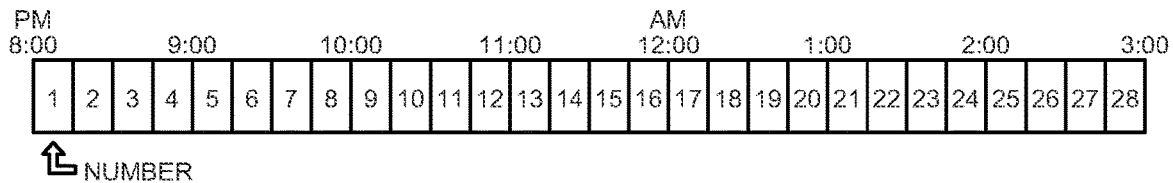

11. YOU WANT TO BE AT YOUR PEAK PERFORMANCE FOR TEST THAT YOU KNOW IS GOING TO BE MENTALLY EXHAUSTING AND WILL LAST FOR TWO HOURS. CONSIDERING THAT YOU ARE ENTIRELY FREE TO PLAN YOUR DAY, AND BEARING IN MIND ONLY LIFE RHYTHM THAT SEEMS TO GIVE YOU THE BEST PHYSICAL CONDITION, WHICH ONE OF THE FOLLOWING TIME ZONE WOULD YOU CHOOSE?

☐ 1 8:00 AM – 10:00 AM  ☐ 2 11:00 AM – 1:00 PM
☐ 3 3:00 PM – 5:00 PM  ☐ 4 7:00 PM – 9:00 PM

12. IF YOU WERE TO GET TO BED AT 11:00 PM, HOW TIRED WOULD YOU BE THEN?

☐ 1 NOT AT ALL TIRED  ☐ 2 A LITTLE TIRED
☐ 3 FAIRLY TIRED  ☐ 4 VERY TIRED

FIG.10

13. FOR SOME REASON YOU HAVE GONE TO BED SEVERAL HOURS LATER THAN USUAL, BUT THERE IS NO NEED TO GET UP AT ANY PARTICULAR TIME THE NEXT MORNING. WHICH ONE OF THE FOLLOWING ARE YOU MOST LIKELY TO DO?

☐ 1 WILL WAKE UP AT USUAL TIME, BUT WILL NOT FALL BACK ASLEEP
☐ 2 WILL WAKE UP AT USUAL TIME AND WILL DOZE THEREAFTER
☐ 3 WILL WAKE UP AT USUAL TIME BUT WILL FALL ASLEEP AGAIN
☐ 4 WILL NOT WAKE UP UNTIL LATER THAN USUAL

14. YOU HAVE TO REMAIN AWAKE BETWEEN 4:00 AND 6:00 AM TO CARRY OUT NIGHT DUTY. YOU HAVE NO COMMITMENT THE NEXT DAY. WHICH ONE OF THE FOLLOWING ALTERNATIVES WOULD SUIT YOU BEST?

☐ 1 WOULD NOT GO TO BED UNTIL DUTY WAS OVER (WOULD SLEEP AFTER DUTY)
☐ 2 WOULD TAKE A NAP BEFORE AND SLEEP AFTER DUTY
☐ 3 WOULD TAKE A GOOD SLEEP BEFORE AND NAP AFTER DUTY
☐ 4 WOULD SLEEP BEFORE DUTY, IF POSSIBLE

15. YOU HAVE TO DO TWO HOURS OF HARD PHYSICAL WORK. CONSIDERING THAT YOU ARE ENTIRELY FREE TO PLAN YOUR DAY, AND BEARING IN MIND ONLY LIFE RHYTHM THAT SEEMS TO GIVE YOU THE BEST PHYSICAL CONDITION, WHICH ONE OF THE FOLLOWING TIME ZONES WOULD YOU CHOOSE?

☐ 1 8:00 AM – 10:00 AM
☐ 2 11:00 AM – 1:00 PM
☐ 3 3:00 PM – 5:00 PM
☐ 4 7:00 PM – 9:00 PM

16. YOU HAVE DECIDED TO ENGAGE IN HARD PHYSICAL EXERCISE. FRIEND SUGGESTS THAT YOU DO THIS FOR ONE HOUR TWICE PER WEEK AND THE BEST TIME IS BETWEEN 10:00 AND 11:00 PM. BEARING IN MIND LIFE RHYTHM THAT SEEMS TO GIVE YOU THE BEST PHYSICAL CONDITION, HOW WELL DO YOU THINK YOU WOULD PERFORM?

☐ 1 WOULD PERFORM IT IN PERFECT FORM
☐ 2 WOULD PERFORM IT IN REASONABLE FORM
☐ 3 WOULD FIND IT DIFFICULT
☐ 4 WOULD FIND IT VERY DIFFICULT

FIG.11

17. SUPPOSE THAT YOU CAN CHOOSE YOUR OWN WORK HOURS. ASSUME THAT YOU WERE TO WORK FIVE CONSECUTIVE HOURS (INCLUDING BREAK), AND THAT YOUR JOB WAS INTERESTING AND PAID BY RESULT. WHICH TIME ZONE WOULD YOU SELECT? SELECT FIVE CONSECUTIVE HOURS FROM THE TIME SCALE BELOW AND MARK THE APPLICABLE NUMBER WITH O.

MIDNIGHT  NOON  MIDNIGHT
12:00

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 12 |
|---|---|---|---|---|---|---|---|---|----|----|----|----|----|----|----|----|----|----|----|----|----|----|----|
| 24 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |

⬆ NUMBER

18. IN WHICH TIME ZONE OF THE DAY DO YOU THINK THAT YOU REACH YOUR BEST PHYSICAL CONDITION? CHOOSE ONLY ONE TIME ZONE, AND MARK THE APPLICABLE NUMBER WITH O.

MIDNIGHT  NOON  MIDNIGHT
12:00

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 12 |
|---|---|---|---|---|---|---|---|---|----|----|----|----|----|----|----|----|----|----|----|----|----|----|----|
| 24 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |

⬆ NUMBER

19. WHEN ASKED WHETHER YOU ARE "MORNING" OR "EVENING" TYPE, WHICH ONE OF THE FOLLOWING TYPES DO YOU ANSWER YOU ARE?

☐ 1 DEFINITELY "MORNING" TYPE
☐ 2 RATHER MORE "MORNING" THAN "EVENING" TYPE
☐ 3 RATHER MORE "EVENING" THAN "MORNING" TYPE
☐ 4 DEFINITELY "EVENING" TYPE

FIG.12

PITTSBURGH SLEEP QUALITY INDEX
(PSQI)

YOUR NAME: _____ DATE OF REPLY: __ / __ /20 __

<PLEASE READ BEFORE YOU ANSWER>
1. ANSWER YOURSELF AS FRANKLY AS POSSIBLE.
2. CHECK ☑ THE APPLICABLE ITEM, OR DIRECTLY FILL IN THE BLANK.
3. WHEN ENTERING TIME, BE SURE TO CHECK "AM" OR "PM".
   *12:00 NOON IS TO BE EXPRESSED AS "0:00 PM", AND 12:00 MIDNIGHT AS "0:00 AM".

---

[QUESTIONS START HERE]
THE QUESTION ASKS YOU ABOUT YOUR MENTAL AND PHYSICAL STATE <u>DURING THE PAST MONTH.</u>
<u>BEARING IN MIND DAY AND NIGHT OF MOST DAYS DURING THE PAST MONTH</u>, ANSWER THE FOLLOWING QUESTIONS AS CORRECTLY AS POSSIBLE.

1. DURING THE PAST MONTH, WHAT TIME HAVE YOU USUALLY GONE TO BED AT NIGHT?

| BEDTIME: ☐ 1  AM   ☐ 2  PM | ABOUT   MINUTE PAST   O'CLOCK |

*12:00 NOON IS TO BE EXPRESSED AS "0:00 PM", AND 12:00 MIDNIGHT AS "0:00 AM".

2. DURING THE PAST MONTH, HOW LONG HAS IT TAKEN YOU FROM WHEN YOU GO TO BED UNTIL YOU FALL ASLEEP?

| ABOUT   MINUTE |

3. DURING THE PAST MONTH, WHAT TIME HAVE YOU USUALLY GOTTEN UP?

| WAKEUP TIME: ☐ 1  AM   ☐ 2  PM | ABOUT   MINUTE PAST   O'CLOCK |

*12:00 NOON IS TO BE EXPRESSED AS "0:00 PM", AND 12:00 MIDNIGHT AS "0:00 AM".

4. DURING THE PAST MONTH, HOW MANY HOURS OF ACTUAL SLEEP DID YOU GET AT NIGHT? (<u>THIS MAY DIFFER FROM THE NUMBER OF HOURS YOU SPENT IN BED.</u>)

| SLEEPING HOUR:<br>ABOUT   HOUR   MINUTE PER DAY IN AVERAGE |

FIG.13

9. DURING THE PAST MONTH, HOW MUCH OF PROBLEM HAS IT BEEN FOR YOU TO KEEP UP ENOUGH ENTHUSIASM TO GET THINGS DONE?

- ☐ 1 NO PROBLEM AT ALL
- ☐ 2 ONLY VERY SLIGHT PROBLEM
- ☐ 3 SOMEWHAT OF PROBLEM
- ☐ 4 VERY BIG PROBLEM

10. DO YOU HAVE FAMILY OR ROOMMATE?

- ☐ 1 NO FAMILY OR ROOMMATE ⇒ END OF QUESTION
- ☐ 2 FAMILY/ROOMMATE IN OTHER ROOM
- ☐ 3 FAMILY/ROOMMATE IN THE SAME ROOM, BUT NOT IN THE SAME BED
- ☐ 4 FAMILY/ROOMMATE IN THE SAME BED

ANSWER THE FOLLOWING QUESTION.

IF YOU HAVE FAMILY OR ROOMMATE, ASK HIM/HER <u>ABOUT YOUR SLEEP</u> ON HOW OFTEN IN THE PAST MONTH YOU HAVE HAD THE FOLLOWING.

| | NEVER | LESS THAN ONCE PER WEEK | ONCE OR TWICE PER WEEK | THREE OR MORE TIMES PER WEEK |
|---|---|---|---|---|
| A. LOUD SNORING | ☐1 | ☐2 | ☐3 | ☐4 |
| B. PAUSE FOR A WHILE BETWEEN BREATH DURING SLEEP | ☐1 | ☐2 | ☐3 | ☐4 |
| C. LEG TWITCHING OR JERKING WHILE YOU SLEEP | ☐1 | ☐2 | ☐3 | ☐4 |
| D. EPISODE OF DISORIENTATION OR CONFUSION DURING SLEEP | ☐1 | ☐2 | ☐3 | ☐4 |
| J. OTHER RESTLESSNESS WHILE YOU SLEEP; PLEASE DESCRIBE<br><br>[REASON] _____<br>_____<br>_____<br><br>HOW OFTEN HAS THIS HAPPENED DURING THE PAST MONTH? | ☐1 | ☐2 | ☐3 | ☐4 |

FIG.14

| 1 | I AM STRONGLY WILLING TO BE STRICT WITH MYSELF, AND AM ALWAYS TIDY. | ☐ |
|---|---|---|
| 2 | I AM GOOD AT RESPONDING FLEXIBLY TO CIRCUMSTANCE. | ☐ |
| 3 | I LIKE TO GIVE CAREFUL CONSIDERATION TO KNOWLEDGE AND INFORMATION OBTAINED AND ANALYZE THEM. | ☐ |
| 4 | I AM ALWAYS SEEKING FOR VARIOUS POSSIBILITY. | ☐ |
| 5 | I CAN ACCEPT MOST THINGS THAT SEEM TROUBLEOME. | ☐ |
| 6 | I BOLDLY EXPRESS WHAT SHOULD BE SAID EVEN TO A SUPERIOR. | ☐ |
| 7 | WHEN MAKING DECISIONS, I LIKE TO CONCLUDE AFTER REACHING A CONSENSUS, RESPECTING EVERYONE'S OPINION. | ☐ |
| 8 | I THINK THAT WHAT MATTERS MOST IS BEING INDIVIDUAL AND SHOWING UNIQUENESS. | ☐ |
| 9 | I OFTEN CARE FOR OTHERS AHEAD OF MYSELF. | ☐ |
| 10 | I THINK THAT COMPETITION IS UNAVOIDABLE TO GAIN HONOR OR STATUS. | ☐ |
| 11 | I AM UNEASY UNLESS THING IS TIDY UP TO DETAIL. | ☐ |
| 12 | I TRY TO STEP OUT OF SITUATION WHERE TROUBLE IS LIKELY TO OCCUR. | ☐ |
| 13 | I WANT TO USE AS MUCH INFORMATION, KNOWLEDGE, AND TIME IN HAND AS POSSIBLE FOR MYSELF. | ☐ |
| 14 | I THINK THAT FEW PEOPLE REALLY UNDERSTAND ME. | ☐ |
| 15 | I AM CAUTIOUS, AND CAREFUL AND ANXIOUS ABOUT VARIOUS THINGS. | ☐ |
| 16 | I EVEN SOMEWHAT FORCEFULLY TRY TO PUSH THINGS FORWARD AS I DESIRE. | ☐ |
| 17 | I SOMETIMES TAKE THINGS LIGHTLY AND FINISH IMPERFECTLY. | ☐ |
| 18 | I THINK THAT WHAT MATTERS MOST IS INTIMATE AND LOVING HUMAN RELATIONSHIP. | ☐ |
| 19 | I TRY TO BE RESPONSIBLE FOR FAITHFULLY CARRYING OUT ENTRUSTED WORK. | ☐ |
| 20 | I LIKE RELAXED PACE, AND SELDOM HURRY. | ☐ |
| 21 | I TEND TO BE GOOD AT ARRANGING THINGS, AND EFFICIENTLY HANDLE EVERYTHING WITHOUT FLAW. | ☐ |
| 22 | I SET TARGET ONE LEVEL ABOVE, AND MAKE EFFORT TO IMPROVE MYSELF. | ☐ |
| 23 | I AM SOCIABLE AND TRY TO MAKE DELIGHTFUL OCCASION FOR PEOPLE AROUND AND MYSELF. | ☐ |
| 21 | TIME TO BE ALONE IS NECESSARY TO CONCENTRATE ON THINGS OF INTEREST. | ☐ |
| 25 | I AM PRIVATELY PROUD OF MY OWN SENSE OF BEAUTY AND SENSIBILITY. | ☐ |
| 26 | I UNDERSTAND WELL WHAT OTHERS WANT, AND TRY TO RESPOND TO THEM. | ☐ |
| 27 | I CONFRONT DIFFICULT SITUATION WITHOUT BEING AFRAID OF GETTING HURT. | ☐ |
| 28 | I TEND TO COMPLY WITH OTHERS WITHOUT EXPRESSING WHAT I THINK. | ☐ |
| 29 | I AM TEMPERAMENTAL, AND SOMETIMES SHOW PERVERSE SIDE. | ☐ |
| 30 | WHEN MAKING JUDGMENT OR DECISION, I CAN FEEL SECURE IF I GET AN APPROVAL OF PERSON I TRUST. | ☐ |

FIG.15

| | NEVER | ALMOST NEVER | SOME-TIMES | FAIRLY OFTEN | VERY OFTEN |
|---|---|---|---|---|---|
| IN THE LAST MONTH, HOW OFTEN HAVE YOU FELT ANXIOUS FOR SOMETHING THAT HAPPENED UNEXPECTEDLY? | N | AN | S | FO | VO |
| IN THE LAST MONTH, HOW OFTEN HAVE YOU FELT UNABLE TO CONTROL THE IMPORTANT THINGS IN YOUR LIFE? | N | AN | S | FO | VO |
| IN THE LAST MONTH, HOW OFTEN HAVE YOU FELT NERVOUS AND "STRESSED"? | N | AN | S | FO | VO |
| IN THE LAST MONTH, HOW OFTEN HAVE YOU DEALT SUCCESSFULLY WITH DAY TO DAY PROBLEM AND ANNOYANCE? | N | AN | S | FO | VO |
| IN THE LAST MONTH, HOW OFTEN HAVE YOU FELT THAT YOU WERE EFFECTIVELY COPING WITH IMPORTANT CHANGES THAT WERE OCCURRING IN YOUR LIFE? | N | AN | S | FO | VO |
| IN THE LAST MONTH, HOW OFTEN HAVE YOU FELT CONFIDENT ABOUT YOUR ABILITY TO HANDLE YOUR PERSONAL PROBLEM? | N | AN | S | FO | VO |
| IN THE LAST MONTH, HOW OFTEN HAVE YOU FELT THAT THING WAS GOING YOUR WAY? | N | AN | S | FO | VO |
| IN THE LAST MONTH, HOW OFTEN HAVE YOU FOUND THAT YOU COULD NOT COPE WITH ALL THE THINGS THAT YOU HAD TO DO? | N | AN | S | FO | VO |
| IN THE LAST MONTH, HOW OFTEN HAVE YOU BEEN ABLE TO CONTROL IRRITATION IN YOUR LIFE? | N | AN | S | FO | VO |
| IN THE LAST MONTH, HOW OFTEN HAVE YOU FELT THAT YOU WERE ON TOP OF THINGS? | N | AN | S | FO | VO |
| IN THE LAST MONTH, HOW OFTEN HAVE YOU BEEN ANGRY ABOUT THINGS THAT HAPPENED OUTSIDE OF YOUR CONTROL? | N | AN | S | FO | VO |
| IN THE LAST MONTH, HOW OFTEN HAVE YOU FOUND YOURSELF THINKING ABOUT THINGS THAT YOU HAVE TO ACCOMPLISH? | N | AN | S | FO | VO |
| IN THE LAST MONTH, HOW OFTEN HAVE YOU BEEN ABLE TO CONTROL THE WAY YOU SPEND YOUR TIME? | N | AN | S | FO | VO |
| IN THE LAST MONTH, HOW OFTEN HAVE YOU FELT DIFFICULTY WAS PILING UP SO HIGH THAT YOU COULD NOT OVERCOME IT? | N | AN | S | FO | VO |

FIG.16

| DATE | PRACTICE | NOTICED THING | IMPRESSION |
|---|---|---|---|
| EXAMPLE) WEDNESDAY MONTH: O DAY: × | ☑ BREATHING 30 MINUTES<br>☑ HABIT 2 TIMES | MUSIC WAS SOUNDING IN MY HEAD.<br>I WAS THINKING ABOUT DINNER. | I LOST ATTENTION QUICKLY DURING BREATHING.<br>I GOT BETTER VIEW THAN USUAL DURING WALKING. |
| EXAMPLE) DAY OF WEEK: ☐☐ MONTH: ☐ DAY: ☐ | ☐ BREATHING ☐☐MINUTES<br>☐ HABIT☐☐TIMES | | |
| EXAMPLE) DAY OF WEEK: ☐☐ MONTH: ☐ DAY: ☐ | ☐ BREATHING ☐☐MINUTES<br>☐ HABIT☐☐TIMES | | |
| EXAMPLE) DAY OF WEEK: ☐☐ MONTH: ☐ DAY: ☐ | ☐ BREATHING ☐☐MINUTES<br>☐ HABIT☐☐TIMES | | |
| EXAMPLE) DAY OF WEEK: ☐☐ MONTH: ☐ DAY: ☐ | ☐ BREATHING ☐☐MINUTES<br>☐ HABIT☐☐TIMES | | |
| EXAMPLE) DAY OF WEEK: ☐☐ MONTH: ☐ DAY: ☐ | ☐ BREATHING ☐☐MINUTES<br>☐ HABIT☐☐TIMES | | |
| EXAMPLE) DAY OF WEEK: ☐☐ MONTH: ☐ DAY: ☐ | ☐ BREATHING ☐☐MINUTES<br>☐ HABIT☐☐TIMES | | |
| EXAMPLE) DAY OF WEEK: ☐☐ MONTH: ☐ DAY: ☐ | ☐ BREATHING ☐☐MINUTES<br>☐ HABIT☐☐TIMES | | |

FIG.20
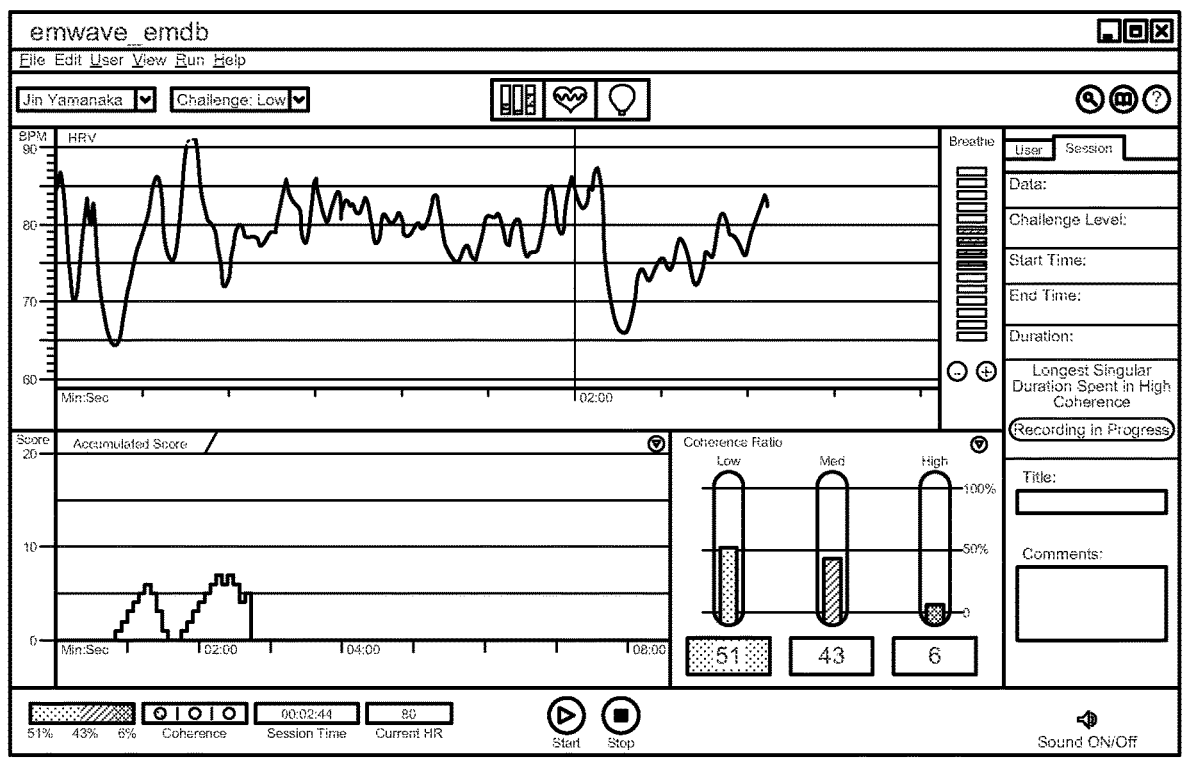
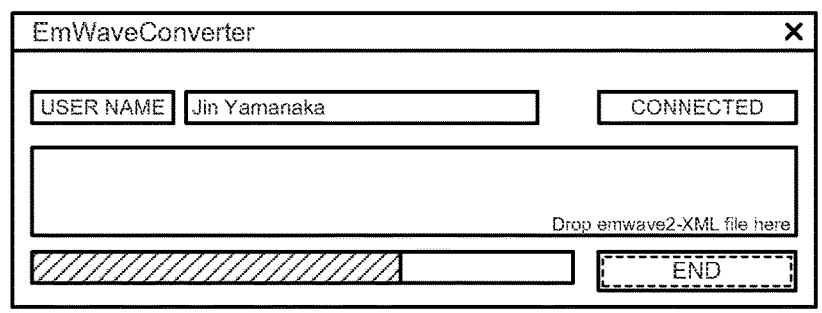

FIG.31

| Gene | Previously associated variant | Description | Reference |
|---|---|---|---|
| AKT1 | Rs1130214 | cognitive performance (CANTAB: Verbal L&M) | (Need, 2009) |
| BDNF | rs6265 | cognitive performance (CANTAB: Verbal L&M) | (Need, 2009) |
| CAMTA1 | rs4908449 | cognitive performance (CANTAB: Verbal L&M) | (Need, 2009) |
| CLSTN2 | rs6439886 | cognitive performance (CANTAB: Verbal L&M) | (Need, 2009) |
| COMT | rs4680 | cognitive performance (CANTAB: Verbal L&M) | (Need, 2009) |
| DAOA | rs17571 | cognitive performance (CANTAB: Set shifting) | (Need, 2009) |
| HIR2A | rs3918342, rs1421292 | cognitive performance (CANTAB: Verbal L&M) | (Need, 2009) |
| KINBRA | rs6314 | cognitive performance (CANTAB: Verbal L&M) | (Need, 2009) |
|  | rs17070145 | cognitive performance (CANTAB: Verbal L&M) | (Need, 2009) |
| NRG1 | rs35753505, rs6994992, SNP8NRG433E1006 | cognitive performance (CANTAB: Situated) attention and spatial and verbal L&M | (Need, 2009) |
| OXTR | rs53576 | optimism and empathy | (Saphire Bernstein, 2011) (Kogan, 2011) (Rodrigues, 2009) (Similie, 2011) (Klein, 2007) |
| DRD2/ANKK1 | rs1800497 | extraversion, avoidance of errors | (Reuter, 2011) |
| COMT Val158Met | rs4680 | altruism | |

FIG. 32
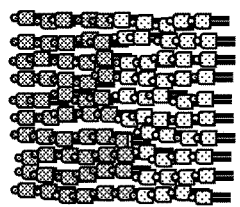
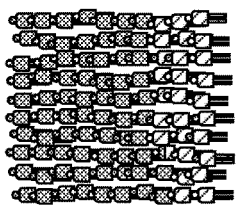

FIG.41
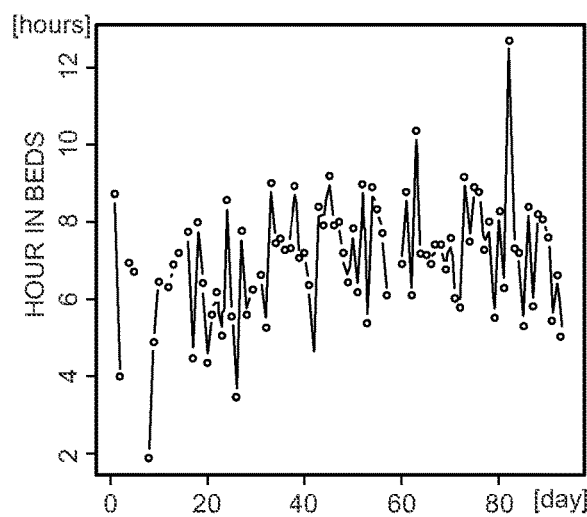
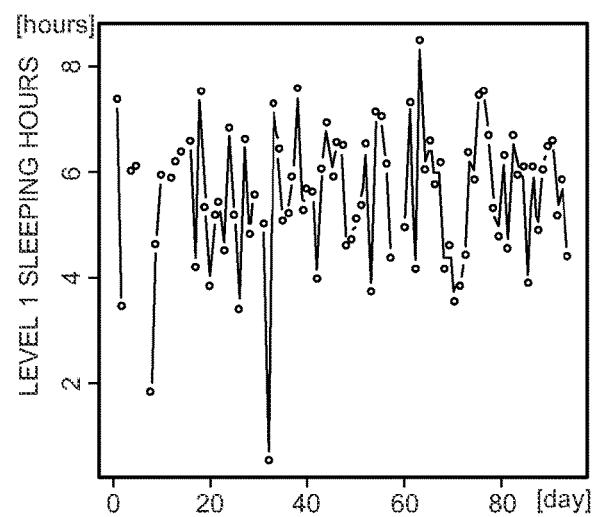
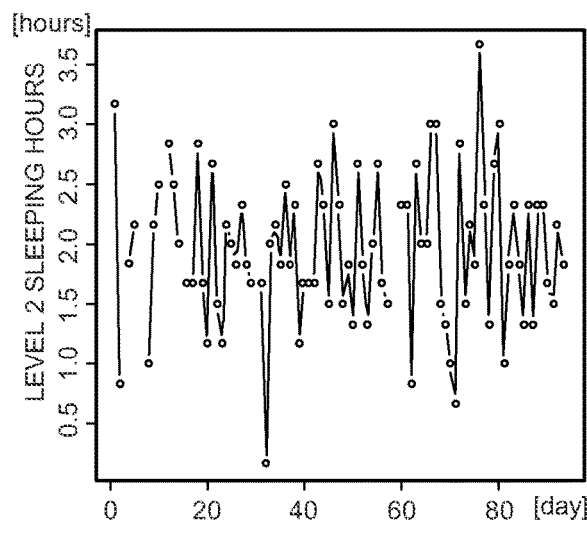
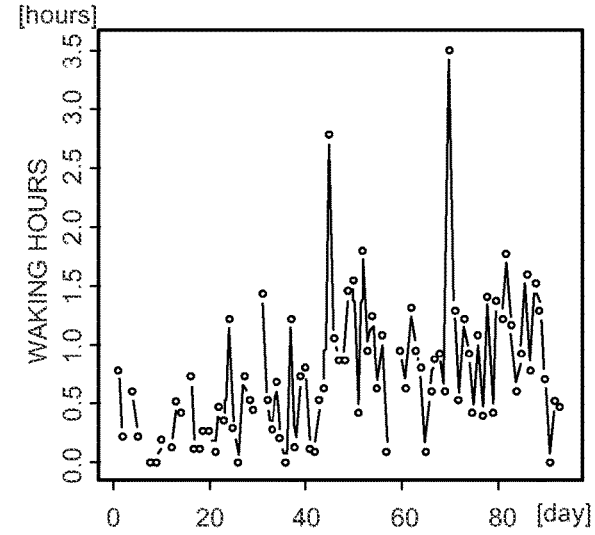

PERSONAL GENOME INFORMATION ENVIRONMENT PROVIDING DEVICE, PERSONAL GENOME INFORMATION ENVIRONMENT PROVIDING METHOD, AND COMPUTER PROGRAM PRODUCT

CROSS REFERENCE TO RELATED APPLICATIONS

This patent application is a U.S. national stage application under 35 U.S.C. § 371 of International Patent Application No. PCT/JP2013/058433 filed on Mar. 22, 2013, which claims the benefit of foreign priority to Japanese Patent Application No. JP 2012-067762 filed on Mar. 23, 2012, the disclosures of all of which are hereby incorporated by reference in their entireties. The International Application was published in Japanese on Sep. 26, 2013, as International Publication No. WO 2013/141386 A1 under PCT Article 21(2).

TECHNICAL FIELD

The present invention relates to a personal genome information environment providing device, a personal genome information environment providing method, and a computer program product.

BACKGROUND ART

Technologies for providing physical or mental healthcare information have conventionally been disclosed.

In a method for prediction of disease risk described in Non Patent Literature 1, a technology for achieving personalized medicine is disclosed that aims at making use of differences in genes among individuals for preventive medical care by using recent rapid cost reduction in innovative technologies, such as next-generation sequencing and sequencer technologies, to predict personal disease risk by finding genes related to diseases.

In social networking services described in Non Patent Literature 2 to 5, participatory health care and participatory scientific discoveries, that is, a technology called "citizen science" is disclosed that shares human information connected via the Internet by actively using communities such as social networking sites, and uses the information for problem solving, health care, and scientific discoveries. Such social networking services facilitate many general people in good health to obtain personal genome information that has conventionally been used mainly among only medical researchers in genetic research for sick people. This allows the social networking services to collect a dramatically larger number of pieces of sample data than that conventionally collected, and presents a possibility of finding new knowledge completely different from conventionally acquired knowledge.

Since old times, a variety of knowledge in religion, philosophy, human relations, and the like for finding a mentally and physically healthy way of life natural to oneself has historically accumulated, and practical programs have been developed in recent years in fields such as coaching and self-development. Examples of such programs have included the Napoleon Hill program (success philosophy), the Dale Carnegie program (human relations), the Enneagram (human relations), and the neuro-linguistic programming (NLP) (self-training based on cognitive psychology). However, such programs have been systematized mainly based on many experiences and cases, and are not necessarily supported by scientific data. In a method called an experience sampling method (ESM) described in Non Patent Literature 6, a technology is disclosed that approaches factors that cause people to feel happiness based on scientific data. Specifically, in the ESM, a technology is disclosed in which pagers are distributed to participants, then data is gathered on how the participants felt in what state when the pagers sounded, and an analysis is made as to in what state people feel happiness.

CITATION LIST

Non Patent Literature

Non Patent Literature 1: Pauline C. Ng, Sarah S. Murray, Samuel Levy, and J. Craig Venter, An agenda for personalized medicine, Nature, External system, Oct. 8, 2009; 461 (7265):724-6.
Non Patent Literature 2: 23 and Me (https://www.23andme.com/)
Non Patent Literature 3: PatientsLikeMe (http://www.patientslikeme.com/)
Non Patent Literature 4: PharmGKB (http://www.pharmgkb.org/)
Non Patent Literature 5: Folding@home (http://folding.stanford.edu/)
Non Patent Literature 6: Csikszentmihalyi, Mihaly (1998), Finding Flow: The Psychology of Engagement with Everyday Life, Basic Books.

SUMMARY OF INVENTION

Problem to be Solved by the Invention

However, the method for prediction of disease risk described in Non Patent Literature 1 mainly focuses on applications in the medical field, thus having a problem of not having been developed from the viewpoint of how personal genome information can have an influence on a person in non-medical fields. While search for related genes, disease prediction, and the like are greatly affected by racial differences, this method for prediction of disease risk currently focuses on data on Europeans and Americans, and does not take the racial differences into account in predicting physical constitutions, and the prediction model itself is still under research, which is a problem. Regarding this method for prediction of disease risk, different prediction results are reported from a plurality of genetic testing companies, which is a problem.

In the conventional social networking services described in Non Patent Literature 2 to 5, research has scarcely been performed so far on benefit and risk of a framework of a participatory scientific discovery project, which is a problem.

The conventional ESM described in Non Patent Literature 6 only covers analysis of data in the form of a questionnaire based on subjectivity without using objective data such as biological signals, and is limited in the number and available time of the participants, which is a problem.

The present invention has been made in view of the above-described problems, and it is an object thereof to provide a personal genome information environment providing device, a personal genome information environment providing method, and a computer program product that can achieve an information providing environment in which, by employing personal genome information serving as scientific data into the personal lifestyle of a person beyond the boundary of the medical field, the person can heuristically find awareness or a way of life suited to the person, can then use the finding for competency development, improvement in human relations, or the like, and can find a mentally and physically healthy way of life natural to the person.

Means for Solving Problem

In order to attain this object, a personal genome information environment providing device according to one aspect of the present invention is a personal genome information environment providing device comprising a monitoring device unit that performs self-tracking of habit information and biological signal information of a user, an output unit, a control unit, and a storage unit, wherein the storage unit includes a personal genome information storage unit that stores personal genome information associating genetic information of the user with genetic knowledge information, and the control unit includes a self-tracking information acquiring unit that acquires self-tracking information obtained by integrating the habit information and the biological signal information that are detected by the monitoring device unit, a characteristic information acquiring unit that acquires characteristic information about characteristics of the user based on the personal genome information stored in the personal genome information storage unit and the self-tracking information acquired by the self-tracking information acquiring unit, and an information outputting unit that outputs, via the output unit, the characteristic information acquired by the characteristic information acquiring unit.

The personal genome information environment providing device according to another aspect of the present invention is the personal genome information environment providing device described above, wherein the characteristic information includes interactive knowledge information, the characteristic information acquiring unit includes an information integrating unit that acquires integrated information obtained by integrating the personal genome information stored in the personal genome information storage unit and the self-tracking information acquired by the self-tracking information acquiring unit, and a data mining unit that acquires the interactive knowledge information by performing data mining on the integrated information acquired by the information integrating unit, and the information outputting unit outputs, via the output unit, the interactive knowledge information acquired by the data mining unit.

The personal genome information environment providing device according to still another aspect of the present invention is the personal genome information environment providing device described above, wherein the characteristic information includes any one, some, or all of risk prediction information on genetic diseases, drug efficacy prediction information, and personality prediction information.

The personal genome information environment providing device according to still another aspect of the present invention is the personal genome information environment providing device described above, wherein the interactive knowledge information includes correlation information on a correlation between the genetic information and the self-tracking information, and the data mining unit acquires the interactive knowledge information by performing the data mining using genetic statistical analysis on the integrated information acquired by the information integrating unit.

The personal genome information environment providing device according to still another aspect of the present invention is the personal genome information environment providing device described above, wherein the habit information is information based on any one, some, or all of meals, sleep, exercises, diaries, behavioral records, and behavioral characteristics questionnaires.

The personal genome information environment providing device according to still another aspect of the present invention is the personal genome information environment providing device described above, wherein the biological signal information is information based on any one, some, or all of brain waves, heart rates, sleep waveforms, blood sugar levels, body weights, and amounts of exercises.

A personal genome information environment providing method according to still another aspect of the present invention is a personal genome information environment providing method executed by a personal genome information environment providing device that includes a monitoring device unit that performs self-tracking of habit information and biological signal information of a user, an output unit, a control unit, and a storage unit, wherein the storage unit including a personal genome information storage unit that stores personal genome information associating genetic information of the user with genetic knowledge information, the method executed by the control unit comprising a self-tracking information acquiring step of acquiring self-tracking information obtained by integrating the habit information and the biological signal information that are detected by the monitoring device unit, a characteristic information acquiring step of acquiring characteristic information about characteristics of the user based on the personal genome information stored in the personal genome information storage unit and the self-tracking information acquired at the self-tracking information acquiring step, and an information outputting step of outputting, via the output unit, the characteristic information acquired at the characteristic information acquiring step.

The personal genome information environment providing method according to still another aspect of the present invention is the personal genome information environment providing method described above, wherein the characteristic information includes interactive knowledge information, the characteristic information acquiring step includes an information integrating step of acquiring integrated information obtained by integrating the personal genome information stored in the personal genome information storage unit and the self-tracking information acquired at the self-tracking information acquiring step, and a data mining step of acquiring the interactive knowledge information by performing data mining on the integrated information generated at the information integrating step, and at the information outputting step, the interactive knowledge information acquired at the data mining step is output via the output unit.

The personal genome information environment providing method according to still another aspect of the present invention is the personal genome information environment providing method described above, wherein the characteristic information includes any one, some, or all of risk prediction information on genetic diseases, drug efficacy prediction information, and personality prediction information.

The personal genome information environment providing method according to still another aspect of the present invention is the personal genome information environment providing method described above, wherein the interactive knowledge information includes correlation information on a correlation between the genetic information and the self-tracking information, and at the data mining step, the interactive knowledge information is acquired by performing the data mining using genetic statistical analysis on the integrated information generated at the information integrating step.

The personal genome information environment providing method according to still another aspect of the present invention is the personal genome information environment providing method described above, wherein the habit information is information based on any one, some, or all of meals, sleep, exercises, diaries, behavioral records, and behavioral characteristics questionnaires.

The personal genome information environment providing method according to still another aspect of the present invention is the personal genome information environment providing method described above, wherein the biological signal information is information based on any one, some, or all of brain waves, heart rates, sleep waveforms, blood sugar levels, body weights, and amounts of exercises.

A computer program product according to still another aspect of the present invention is a computer program product having a non-transitory tangible computer readable medium including programmed instructions for causing, when executed by a personal genome information environment providing device that includes a monitoring device unit that performs self-tracking of habit information and biological signal information of a user, an output unit, a control unit, and a storage unit including a personal genome information storage unit that stores personal genome information associating genetic information of the user with genetic knowledge information, the personal genome information environment providing device to perform a personal genome information environment providing method comprising a self-tracking information acquiring step of acquiring self-tracking information obtained by integrating the habit information and the biological signal information that are detected by the monitoring device unit, a characteristic information acquiring step of acquiring characteristic information about characteristics of the user based on the personal genome information stored in the personal genome information storage unit and the self-tracking information acquired at the self-tracking information acquiring step, and an information outputting step of outputting, via the output unit, the characteristic information acquired at the characteristic information acquiring step.

The computer program product according to still another aspect of the present invention is the computer program product described above, wherein the characteristic information includes interactive knowledge information, the characteristic information acquiring step includes an information integrating step of acquiring integrated information obtained by integrating the personal genome information stored in the personal genome information storage unit and the self-tracking information acquired at the self-tracking information acquiring step, and a data mining step of acquiring the interactive knowledge information by performing data mining on the integrated information generated at the information integrating step, and at the information outputting step, the interactive knowledge information acquired at the data mining step is output via the output unit.

The computer program product according to still another aspect of the present invention is the computer program product described above, wherein the characteristic information includes any one, some, or all of risk prediction information on genetic diseases, drug efficacy prediction information, and personality prediction information.

The computer program product according to still another aspect of the present invention is the computer program product described above, wherein the interactive knowledge information includes correlation information on a correlation between the genetic information and the self-tracking information, and at the data mining step, the interactive knowledge information is acquired by performing the data mining using genetic statistical analysis on the integrated information generated at the information integrating step.

The computer program product according to still another aspect of the present invention is the computer program product described above, wherein the habit information is information based on any one, some, or all of meals, sleep, exercises, diaries, behavioral records, and behavioral characteristics questionnaires.

The computer program product according to still another aspect of the present invention is the computer program product described above, wherein the biological signal information is information based on any one, some, or all of brain waves, heart rates, sleep waveforms, blood sugar levels, body weights, and amounts of exercises.

Effect of the Invention

According to this invention, self-tracking information (such as information obtained by integrating habit information and biological signal information) obtained by integrating the habit information (such as a life log of, for example, information on behaviors iterated or repeated on a daily basis, such as meals, sleep, exercises, diaries, behavioral records, or behavioral characteristics) and the biological signal information (such as numerically displayable biological signals, such as blood pressures, pulse rates, brain waves, blood measurements, or amounts of exercises) is acquired; based on personal genome information (such as information based on an analysis result of personal genes) and the self-tracking information, characteristic information about characteristics of a user (such as information on characteristics of the user based on the self-tracking information) is acquired; and the characteristic information is output. This enables a dialogue with an intelligent agent that analyzes the characteristics of a person and encourages the person to gain awareness based on a genetic tendency prediction based on the analysis result of the personal genes and daily records of behavioral habits, so that information for personal living environment improvement can be provided. Thus, an advantageous effect is obtained that the person can be aware of the person's own individuality and the tendency of the person's own behavioral characteristics, and can enhance the sense of improvement toward mentally and physically healthy lifestyle habits suited to the person. In other words, according to this invention, an advantageous effect is obtained that the person can modify working of the person's own brain, mind, and body, and can acquire the mentally and physically healthy lifestyle habits suited to the person by gaining awareness of the person's own individuality. According to this invention, an advantageous effect is obtained that the invention leads to creation of a new field, that is, a web-based genome analysis (such as an analysis for personal living environment improvement using the Web). According to this invention, an advantageous effect is obtained that the invention can contribute to development of a technology to compare and test interactions between a new information environment provided by genetic information and people by employing the knowledge of social information science.

According to this invention, integrated information obtained by integrating the personal genome information and the self-tracking information is obtained; interactive knowledge information is acquired by performing data mining on the integrated information; and the interactive knowledge information is output. As a result, an advantageous effect is obtained that the user can effectively perform the data mining to find the correlation between the genes and the personal behavioral characteristics by introducing a mechanism of safely gathering the personal life log and genome information according to the policy of each person in a community in a voluntary manner while acquiring habits of voluntary self-observation and self-discovery. As a result, according to this invention, for example, an advantageous effect is obtained that each person can participate in a scientific discovery community while enjoying obtaining feedback useful for discovering the personality and improving the abilities of oneself in such a manner as a brain training game.

According to this invention, the characteristic information includes any one, some, or all of risk prediction information on genetic diseases, drug efficacy prediction information, and personality prediction information, so that an advantageous effect is obtained that a scientific discovery platform can be built that provides new knowledge on genetic interpretation in fields such as medicine, pharmacy, and behavioral science. According to this invention, an advantageous effect is obtained that data useful for scientific discovery in fields such as medicine, pharmacy, and behavioral science can be gathered, and cycles useful for new scientific discoveries can be created.

According to this invention, the interactive knowledge information includes correlation information on the correlation between the genetic information and the self-tracking information, and the interactive knowledge information is acquired by the data mining using genetic statistical analysis on the integrated information, so that an advantageous effect is obtained that an interaction understanding can be promoted between the new information environment provided by the genetic information and the self-tracking information and the person.

According to this invention, the habit information is information based on any one, some, or all of meals, sleep, exercises, diaries, behavioral records, and behavioral characteristics questionnaires, so that an advantageous effect is obtained that a habit required by the user can be selected.

According to this invention, the biological signal information is information based on any one, some, or all of brain waves, heart rates, sleep waveforms, blood sugar levels, body weights, and amounts of exercises, so that a biological signal required by the user can be selected.

BRIEF DESCRIPTION OF DRAWINGS

FIG. 5 is a block diagram of the example of the configuration of the personal genome information environment providing device according to the embodiment.

FIG. 6 is a flowchart of an example of processing by the personal genome information environment according to the embodiment.

FIG. 7 is a flowchart of an example of processing by the personal genome information environment according to the embodiment.

FIG. 8 is a diagram of an example of a behavioral characteristics questionnaire according to the embodiment.

FIG. 9 is a diagram of the example of the behavioral characteristics questionnaire according to the embodiment.

FIG. 10 is a diagram of the example of the behavioral characteristics questionnaire according to the embodiment.

FIG. 11 is a diagram of the example of the behavioral characteristics questionnaire according to the embodiment.

FIG. 12 is a diagram of an example of a behavioral characteristics questionnaire according to the embodiment.

FIG. 13 is a diagram of the example of a behavioral characteristics questionnaire according to the embodiment.

FIG. 14 is a diagram of an example of a behavioral characteristics questionnaire according to the embodiment.

FIG. 15 is a diagram of an example of a behavioral characteristics questionnaire according to the embodiment.

FIG. 16 is a diagram of an example of a behavioral characteristics questionnaire according to the embodiment.

FIG. 20 is a diagram of an example of the biological signal acquisition according to the embodiment.

FIG. 31 is a diagram of an example of data stored in a personal genome knowledge database according to the embodiment.

FIG. 32 is a diagram of an example of data stored in the personal genome knowledge database according to the embodiment.

FIG. 41 is a diagram of an example of graphs of changes in sleep-related data obtained by the monitoring device unit according to the embodiment.

MODE(S) FOR CARRYING OUT THE INVENTION

The following explains in detail embodiments of a personal genome information environment providing device, a personal genome information environment providing method, and a computer program product according to the present invention, based on the drawings. This invention is not limited by the embodiments.

Outline of Embodiment According to Present Invention

Figure 1:
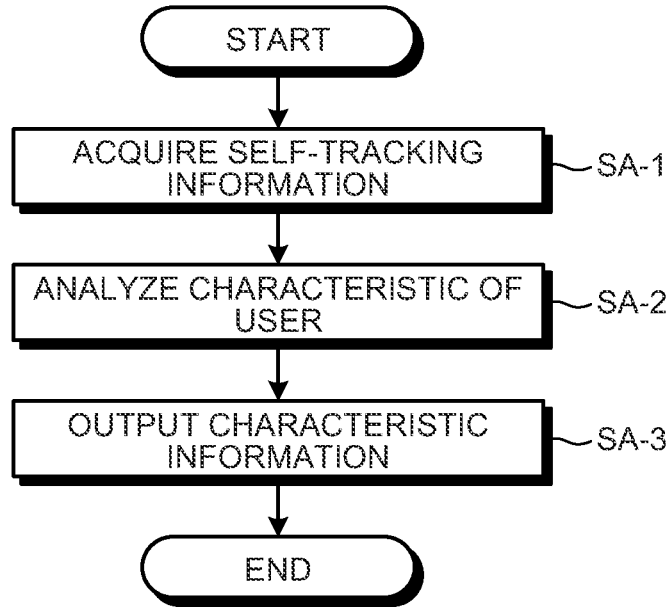
FIG. 1 is a flowchart of the basic principle according to an embodiment of the present invention.

An outline of an embodiment according to the present invention will be explained below with reference to FIGS. 1 to 3, and thereafter, the configuration, processing, and the like according to the present embodiment will be explained in detail. FIG. 1 is a flowchart of the basic principle according to the present embodiment. The present embodiment broadly has the following basic features.

Specifically, as shown in FIG. 1, a control unit of a personal genome information environment providing device according to the present embodiment acquires self-tracking information obtained by integrating habit information of a user and biological signal information of the user that are detected by a monitoring device unit (Step SA-1). The habit information (life log) may be information based on any one, some, or all of meals, sleep, exercises, diaries, behavioral records, and behavioral characteristics questionnaires (behavioral characteristics) (such as information on behaviors iterated or repeated on a daily basis). The biological signal information may be information based on numerically displayable biological signals, such as any one, some, or all of blood pressures, brain waves, heart rates, pulse rates, sleep waveforms, blood sugar levels, blood measurements, body weights, and amounts of exercises.

Based on personal genome information (such as information based on an analysis result of genes of a person) stored in a storage unit and the self-tracking information that has been acquired at Step SA-1, the control unit of the personal genome information environment providing device analyzes characteristics of the user, and obtains characteristic information on the characteristics (Step SA-2). The characteristic information is any one, some, or all of risk prediction information on genetic diseases, drug efficacy prediction information, and personality prediction information, and may be, for example, information on characteristics of each user based on the self-tracking information.

The control unit of the personal genome information environment providing device then outputs the characteristic information obtained at Step SA-2 via an output unit (Step SA-3), and ends the processing.

In this manner, the personal genome information environment providing device extracts behavioral characteristics and thinking characteristics of a person by performing simple self-tracking of daily habitual behavior and biological signal information of the person using a mobile device or the like, and gathering mental and physical state changes together with the behavioral records of the person, and combines the genome information and the behavioral record information of the person. Thereby, the personal genome information environment providing device can provide a personal genome information environment that encourages a person to find one's individuality or personality and to gain new awareness.

An example of the processing at Steps SA-2 and SA-3 of FIG. 1 will further be explained with reference to FIGS. 2 and 3. FIG. 2 is a flowchart of an example of the processing by the personal genome information environment providing device according to the present embodiment. FIG. 3 is a diagram of an example of the concept of the present embodiment.

Figure 2:
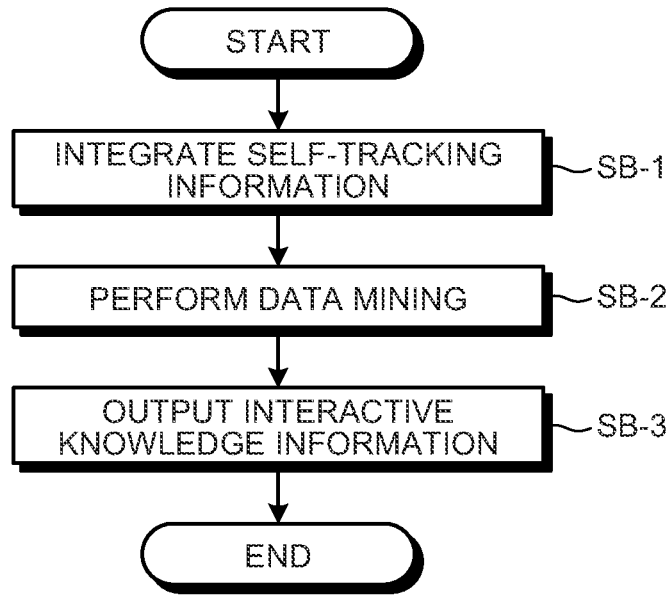
FIG. 2 is a flowchart of an example of processing by a personal genome information environment providing device according to the embodiment.
Figure 3:
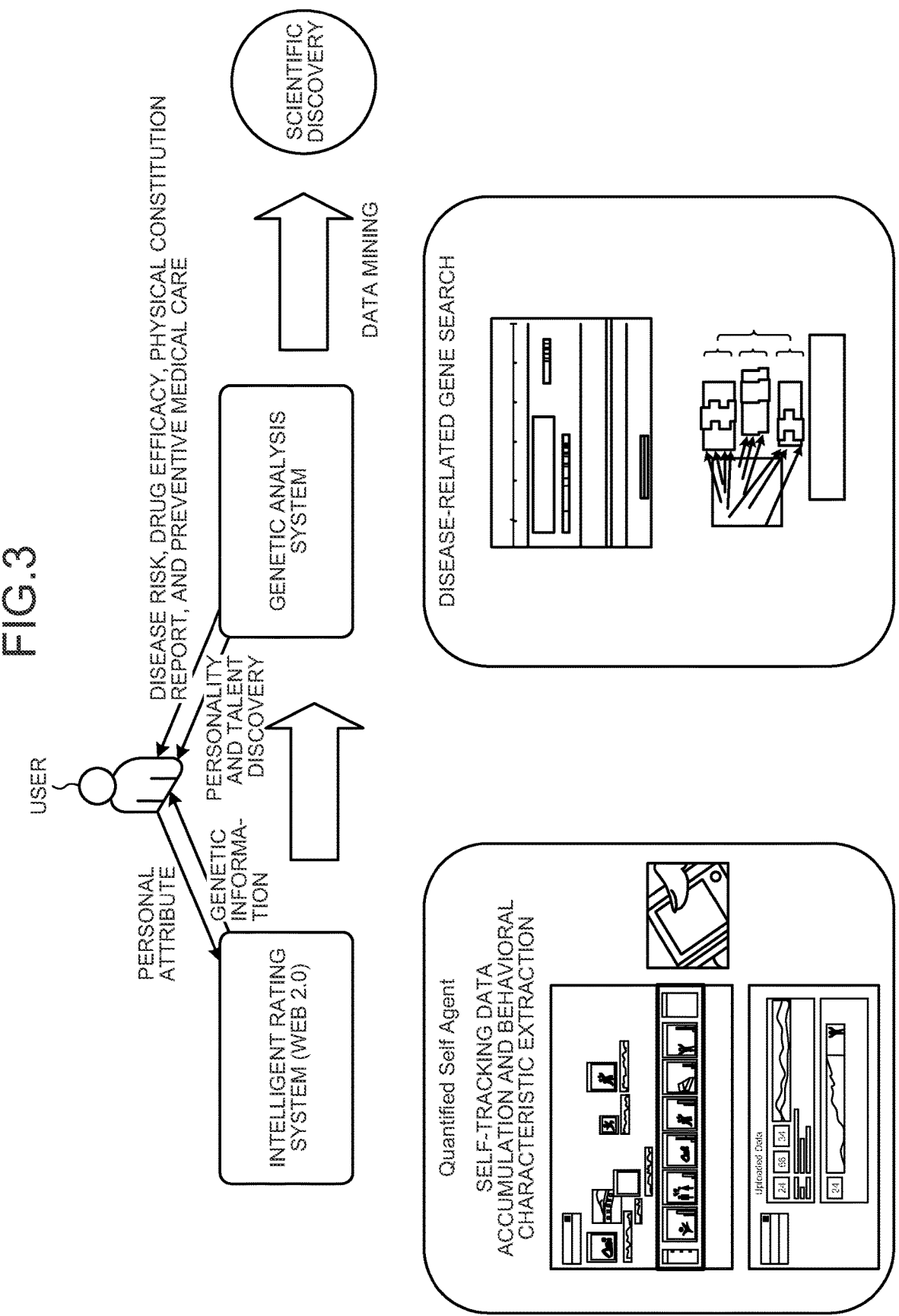
FIG. 3 is a diagram of an example of the concept of the embodiment.

As shown in FIG. 2, the control unit of the personal genome information environment providing device according to the present embodiment acquires integrated information obtained by integrating the personal genome information stored in the storage unit and the self-tracking information obtained by integrating the habit information of the user and the biological signal information of the user (Step SB-1). For example, as shown in FIG. 3, an intelligent rating system (control unit) that is a platform of personalized medicine or the like acquires integrated information obtained by integrating genetic information of the user and self-tracking data (such as personal attributes) of the user that is the behavioral characteristics and the like extracted from data self-tracked by the monitoring device unit and accumulated.

The control unit of the personal genome information environment providing device then acquires interactive knowledge information by performing data mining on the integrated information acquired at Step SB-1 (Step SB-2). The control unit may acquire the interactive knowledge information by performing data mining using genetic statistical analysis on the integrated information acquired at Step SB-1. The interactive knowledge information may include correlation information on the correlation between the genetic information and the self-tracking information. For example, as shown in FIG. 3, a genetic analysis system (control unit) acquires interactive knowledge information (information on, for example, disease risk, drug efficacy, a physical constitution report, preventive medical care, personality, or talent discoveries) that is a new citizen-participatory scientific discovery or the like by performing the data mining using the genetic statistical analysis, such as search for disease-related genes, on the integrated information.

The control unit of the personal genome information environment providing device then outputs, via the output unit, the interactive knowledge information acquired at Step SB-2 (Step SB-3), and ends the processing.

In this manner, by allowing each person to voluntarily share accumulated personal habit records, biological signal information, and personal genome information among a community, and statistically analyzing the correlation between the shared behavioral characteristics and thinking characteristics, and genes, the personal genome information environment providing device can provide a mechanism and a platform for testing or newly finding relativity between characteristics that attract attention in scientific fields, such as medicine, pharmacy, and behavioral science, and the genes. Specifically, the personal genome information environment providing device can provide an information environment in which a person heuristically finds awareness or a way of life suited to the person (including developing competency and improving human relations) based on the scientific data, by using the mechanism in which the person easily accumulates daily personal events, how the person felt then, and in what mental and physical state the person was then, by integrating subjective data and biological signals (brain waves or heart rates) using the latest self-tracking device.

This is the end of the explanation for the outline of the present embodiment.

Configuration of Personal Genome Information Environment Providing Device 100

The detailed configuration of the personal genome information environment providing device 100 according to the present embodiment will be explained below with reference to FIGS. 4 and 5.

Configuration: Part 1

An example of the configuration of the personal genome information environment providing device 100 according to the present embodiment will first be explained below with reference to FIG. 4. FIG. 4 is a block diagram of the example of the configuration of the personal genome information environment providing device 100 according to the present embodiment, schematically showing only portions of the configuration related to the present invention.

Figure 4:
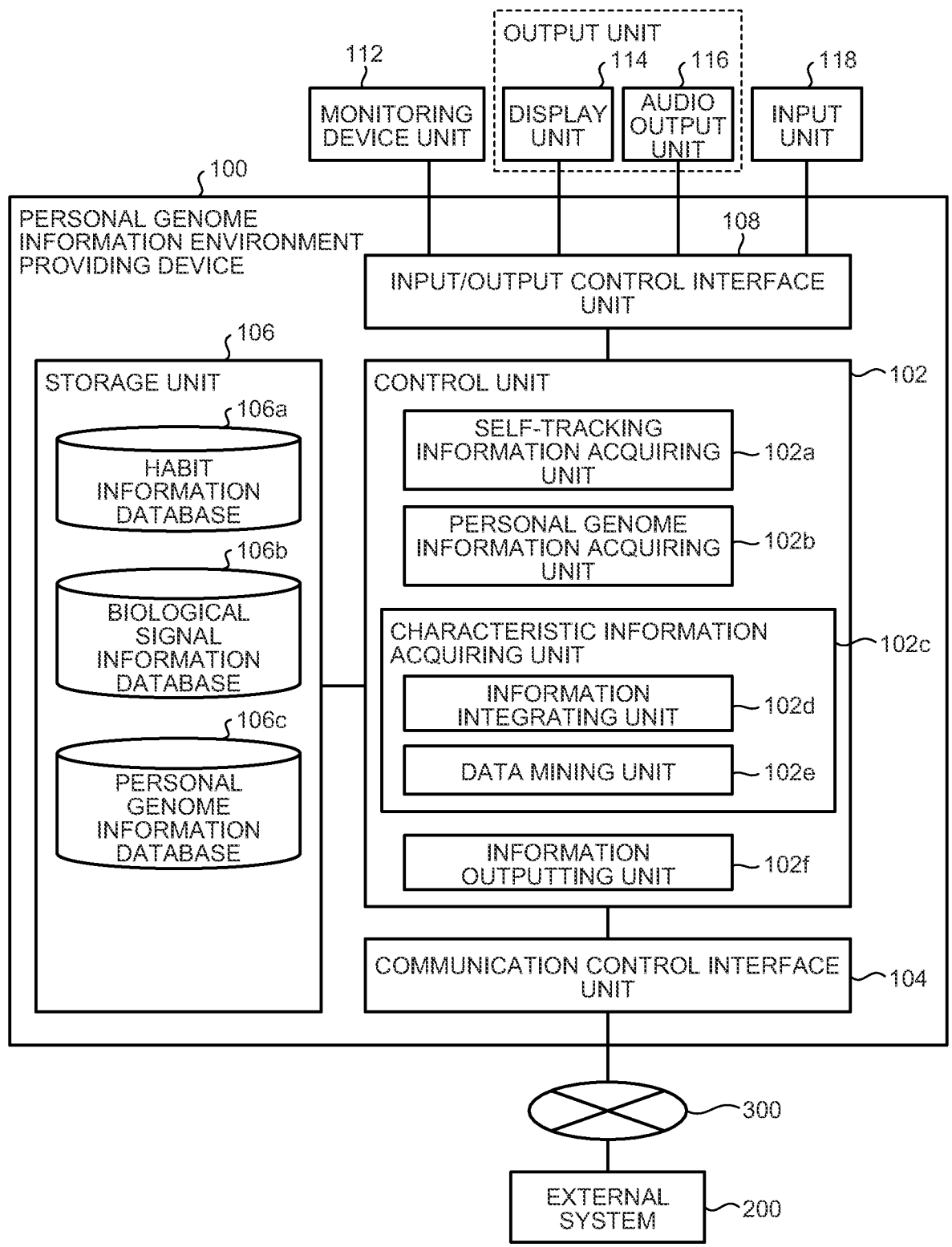
FIG. 4 is a block diagram of an example of the configuration of the personal genome information environment providing device according to the embodiment.

In FIG. 4, a network 300 has a function of interconnecting the personal genome information environment providing device 100 and an external system 200, and is, for example, the Internet.

In FIG. 4, the external system 200 is connected with the personal genome information environment providing device 100 via the network 300, and has a function of providing any one or both of an external database related to genetic information and the like for users and a website that executes external programs or the like, such as social networking.

The external system 200 may be configured as a web server, an application service provider (ASP) server, or the like. The external system 200 may have a hardware configuration constituted by a commercially available information processing device, such as a workstation or a personal computer, and accessory devices thereof. Functions of the external system 200 are implemented by a CPU, a disk drive, a memory device, an input device, an output device, a communication control device, and the like included in the hardware configuration of the external system 200, and programs and the like that control these devices.

In FIG. 4, the personal genome information environment providing device 100 is a personal genome information environment that broadly includes a control unit 102, a communication control interface unit 104, an input/output control interface unit 108, and a storage unit 106. The control unit 102 is a CPU and the like that integrally control the whole of the personal genome information environment providing device 100. The communication control interface unit 104 is an interface connected to a communication device (not shown), such as a router, connected to a communication line or the like. The input/output control interface unit 108 is an interface connected to a monitoring device unit 112, to an output unit including at least a display unit 114 and an audio output unit 116, and to an input unit 118. The storage unit 106 is a device that stores various databases and tables. These units of the personal genome information environment providing device 100 are communicably connected to one another via any communication paths. The personal genome information environment providing device 100 is further communicably connected to the network 300 via the communication device, such as a router, and a wired or wireless communication line, such as a dedicated line.

The various databases and tables (a habit information database 106*a*, a biological signal information database 106*b*, and a personal genome information database 106*c*) stored in the storage unit 106 are storage units such as fixed disk drives. For example, the storage unit 106 stores a variety of programs, tables, files, databases, web pages, and the like that are used for various types of processing.

Of these components of the storage unit 106, the habit information database 106*a* is a habit information storage unit that stores the habit information of the user, and is, for example, a habit record database that records lifestyle habits (life log) of an individual user. The habit information may be information based on any one, some, or all of meals, sleep, exercises, diaries, behavioral records, and behavioral characteristics questionnaires. For example, the habit information may be any one, some, or all of event records, records of replies to questionnaires, records of a social networking service (SNS), diaries, and mental and physical state record information expressed by icons.

The biological signal information database 106*b* is a biological signal information storage unit that stores the biological signal information of the user, and is, for example, a physical information record database that records the biological signals. The biological signal information may be information based on any one, some, or all of brain waves, heart rates (heartbeat sensor data), sleep waveforms, blood sugar levels, body weights, and amounts of exercises.

The personal genome information database 106*c* is a personal genome information storage unit that stores the personal genome information associating the genetic information of the user with genetic knowledge information, and is, for example, a personal genome knowledge database that stores the personal genome information of an individual user and knowledge data about genes. The genetic knowledge information may be information on any one, some, or all of base sequences, genotypes, phenotypes, and annotations. These pieces of the genetic knowledge information are stored in advance in the personal genome information database 106*c*. The control unit 102 of the personal genome information environment providing device 100 may download the latest data from the external system 200 or the like via the network 300 in a periodical manner, or according to processing by the control unit 102 (for example, when triggered by an event where the control unit 102 needs data), or both, and may thus update the genetic knowledge information stored in the personal genome information database 106c.

In FIG. 4, the communication control interface unit 104 controls communication between the personal genome information environment providing device 100 and the network 300 (or the communication device, such as a router). In other words, the communication control interface unit 104 has a function of communicating data with other terminals via the communication line.

In FIG. 4, the input/output control interface unit 108 controls the monitoring device unit 112, the display unit 114, the audio output unit 116, and the input unit 118.

The monitoring device unit 112 is a monitoring device unit that performs self-tracking of the habit information of the user and the biological signal information of the user, and is, for example, a monitoring device group that is a group of portable devices or the like that enable measurement and acquisition of any one, some, or all of the habit information of the user, the biological signal information of the user, and the like. The monitoring device unit 112 may be detachable from the personal genome information environment providing device 100 (may be mobile), and may directly receive data from the external system (external device) 200 via the network 300.

A monitor (including a home television) or the like can be used as the display unit 114 (hereinafter, the display unit 114 may be described as a monitor). The audio output unit 116 may be an audio output unit (such as a speaker) that outputs audio information as a sound. The input unit 118 may be, for example, a key input unit, a touchscreen, a control pad (such as a touchpad or a gamepad), a mouse, a keyboard, or a microphone.

In FIG. 4, the control unit 102 has an internal memory for storing a control program such as an operating system (OS), programs that define various procedures and the like, and necessary data. The control unit 102 performs information processing for executing various types of processing by using these programs and the like. The control unit 102 functionally and conceptually includes a self-tracking information acquiring unit 102a, a personal genome information acquiring unit 102b, a characteristic information acquiring unit 102c, and an information outputting unit 102f.

Of these units, the self-tracking information acquiring unit 102a is a self-tracking information acquiring unit that acquires the self-tracking information obtained by integrating the habit information and the biological signal information that have been detected by the monitoring device unit 112, and is, for example, an information integrating engine including a module obtained by integrating the habit information and the biological signal information.

The personal genome information acquiring unit 102b is a personal genome information acquiring unit that acquires the genetic information of the user, and obtains the personal genome information associating the genetic information with the genetic knowledge information. The personal genome information acquiring unit 102b may further store the personal genome information into the personal genome information database 106c.

The characteristic information acquiring unit 102c is a characteristic information acquiring unit that analyzes characteristics of the user and acquires characteristic information about the characteristics based on the personal genome information and the self-tracking information acquired by the self-tracking information acquiring unit 102a. The characteristic information may include any one, some, or all of the risk prediction information on genetic diseases, the drug efficacy prediction information, and the personality prediction information. The characteristic information may also include the interactive knowledge information. The interactive knowledge information may include the correlation information on the correlation between the genetic information and the self-tracking information. As shown in FIG. 4, the characteristic information acquiring unit 102c includes at least an information integrating unit 102d and a data mining unit 102e.

The information integrating unit 102d is an information integrating unit that acquires the integrated information obtained by integrating the personal genome information and the self-tracking information acquired by the self-tracking information acquiring unit 102a, and is, for example, an information integrating engine including a module obtained by integrating the genome data and the self-tracking data.

The data mining unit 102e is a data mining unit that acquires the interactive knowledge information by performing the data mining on the integrated information acquired by the information integrating unit 102d, and is, for example, a data mining engine including a module that discovers knowledge from the genome data and the self-tracking data. The data mining unit 102e may acquire the interactive knowledge information by performing the data mining using the genetic statistical analysis on the integrated information acquired by the information integrating unit 102d.

The information outputting unit 102f is a characteristic information outputting unit that outputs, via the output unit, the characteristic information acquired by the characteristic information acquiring unit 102c, and is, for example, an intelligent agent engine serving as an interface that encourages a person to gain awareness. The information outputting unit 102f may output, via the output unit, the interactive knowledge information obtained by the data mining unit 102e. The information outputting unit 102f may be, for example, an intelligent agent engine serving as an interface that encourages the user to gain awareness while interactively presenting knowledge to the user. The information outputting unit 102f may display the characteristic information and the like on the display unit 114. The information outputting unit 102f may output the characteristic information and the like via the audio output unit 116.

This is the end of the explanation for Part 1 of the configuration according to the present embodiment.

Configuration: Part 2

The example of the configuration of the personal genome information environment providing device 100 according to the present embodiment will be explained below with reference to FIG. 5. FIG. 5 is block diagram of the example of the configuration of the personal genome information environment providing device 100 according to the present embodiment, schematically showing only portions of the configuration related to the present invention.

In FIG. 5, the habit record database (habit information database) 106a of the personal genome information environment (personal genome information environment providing device) 100 stores the user's life log, that is, habit records (habit information) about lifestyle habits of the person, including meals, sleep, exercises, diaries, behavioral records, behavioral characteristics questionnaires, event records, records of replies to questionnaires, SNS records, diaries, mental and physical state records expressed by icons, and the like that have been self-tracked by the monitoring device group (monitoring device unit) 112.

The physical information record database (biological signal information database) 106b of the personal genome information environment 100 stores the physical information (biological signal information) that is biological signals such as the brain waves, the heart rates, the body weights, and the amounts of exercises of the user that have been self-tracked by the monitoring device group 112.

The personal genome knowledge database (personal genome information database) 106c stores the genome information of a person and the knowledge data about genes.

The information integrating engine of the personal genome information environment 100 is a module including the module (self-tracking information acquiring unit 102a) obtained by integrating the habit information stored in the habit record database 106a and the biological signal information stored in the physical information record database 106b, and the module (information integrating unit 102d) obtained by integrating the self-tracking data and the genome data that is stored in the personal genome knowledge database 106c.

The data mining engine (data mining unit) 102e is a module that discovers knowledge from the self-tracking data stored in the habit record database 106a and the physical information record database 106b, and the genome data stored in the personal genome knowledge database 106c.

The intelligent agent engine (information outputting unit) 102f is an interface that encourages the user to gain awareness while interactively presenting knowledge to the user.

In this manner, by having the configuration including the habit record database 106a, the physical information record database 106b, the personal genome knowledge database 106c, and the intelligent agent engine 102f, the personal genome information environment 100 is configured to perform scientific evidence accumulation and support for discovery of behavioral characteristics, which are not available by conventional coaching support technologies.

This is the end of the explanation for the example of the configuration of the personal genome information environment providing device 100 according to the present embodiment.

Processing by Personal Genome Information Environment 100

The following explains details of processing by the thus-configured personal genome information environment 100 according to the present embodiment with reference to FIGS. 6 to 39.

An example of the processing by the personal genome information environment 100 according to the present embodiment will first be explained with reference to FIG. 6. FIG. 6 is a flowchart of the example of the processing by the personal genome information environment 100 according to the present embodiment.

As shown in FIG. 6, if the monitoring device unit 112 has self-tracked the habit information (behavioral records), the control unit 102 acquires the behavioral records, and stores them in the habit record database 106a, or if the monitoring device unit 112 has self-tracked the biological signal information (biological signals) of the user, the control unit 102 acquires the biological signals, and stores them in the physical information record database 106b (Step SC-1). The behavioral records may be information based on any one, some, or all of meals, sleep, stresses, breathing, personality, exercises, diaries, behavioral records, behavioral characteristics questionnaires, and events (such as daily events and social networking). The biological signals may be physical information based on any one, some, or all of brain waves, heart rates (heartbeat sensor data), sleep waveforms, blood sugar levels, body weights, and amounts of exercises. The monitoring device unit 112 may be a mobile terminal or the like that detects, for example, amounts of exercises, sleep, brain waves, and body weights.

An example of the self-tracking processing according to the present embodiment will be explained with reference to FIG. 7. FIG. 7 is a flowchart of the example of the processing by the personal genome information environment 100 according to the present embodiment.

As shown in FIG. 7, if the monitoring device unit 112 has self-tracked the habit information (habit records) on personality, sleep, breathing, stresses, or the like using the questionnaires, the control unit 102 acquires the habit records, and stores them in the habit record database 106a (Step SD-1). The habit records may be entered by the user via the input unit 118, or may be received via the network 300.

Then, if the monitoring device unit 112 has self-tracked the habit information (event records) on the daily social networking, the behavioral records, or the like, the control unit 102 acquires the event records, and stores them in the habit record database 106a (Step SD-2). The event records may be entered by the user via the input unit 118, or may be received via the network 300.

Then, if the monitoring device unit 112 has self-tracked the biological signal information (biological signal records) on brain waves, heartbeats, or the like, the control unit 102 acquires the biological signal records, then stores them in the physical information record database 106b (Step SD-3), and ends the processing.

This is the end of the explanation for the example of the self-tracking processing according to the present embodiment.

Examples of behavioral characteristics questionnaires according to the present embodiment will be explained with reference to FIGS. 8 to 16. FIGS. 8 to 16 are diagrams of the examples of the behavioral characteristics questionnaires according to the present embodiment.

The behavioral characteristics questionnaire shown in FIGS. 8 to 11 is a morningness-eveningness questionnaire (MEQ) that is a questionnaire for selectively rating sleeping habits. The behavioral characteristics questionnaire shown in FIGS. 12 and 13 is a Pittsburgh sleep quality index (PSQI) questionnaire that is another questionnaire for selectively rating the sleeping habits. The behavioral characteristics questionnaire shown in FIG. 14 is a questionnaire for rating the personality type of the user, and is an enneagram questionnaire of a type in which question items about personality are selected or not selected. The behavioral characteristics questionnaire shown in FIG. 15 is a questionnaire for rating the stress state of the user, and is a questionnaire of a type in which question items about stresses are selected from five levels ("never", "almost never", "sometimes", "fairly often", and "very often"). The behavioral characteristics questionnaire shown in FIG. 16 is a questionnaire for rating the breathing (meditation experience) of the user, and is a questionnaire of a type in which the user enters the date of the meditation experience, durations and times of the practice (habits), what the user has noticed during the practice, and impressions.

Figure 17:
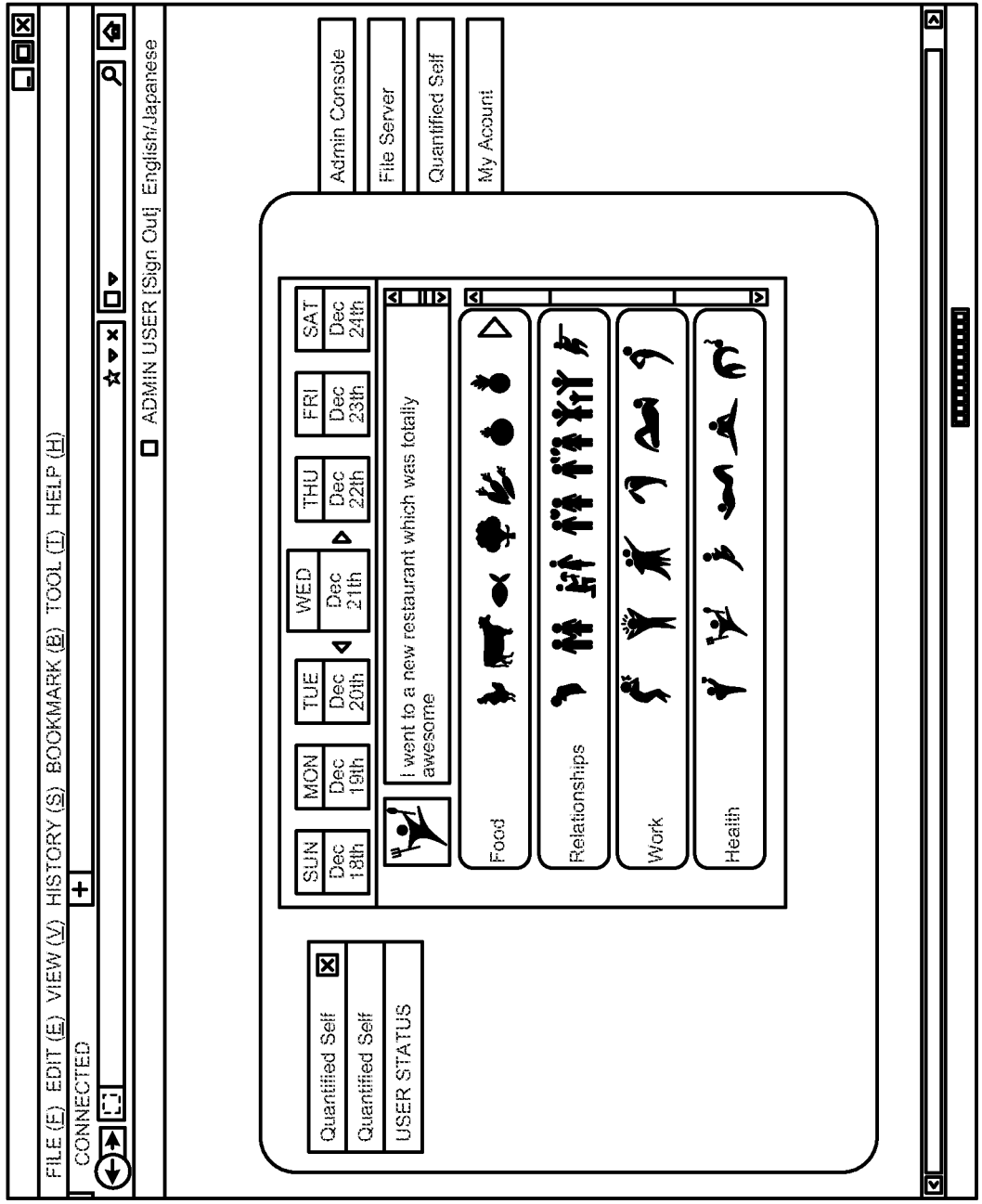
FIG. 17 is a diagram of an example of behavioral records according to the embodiment.
Figure 18:
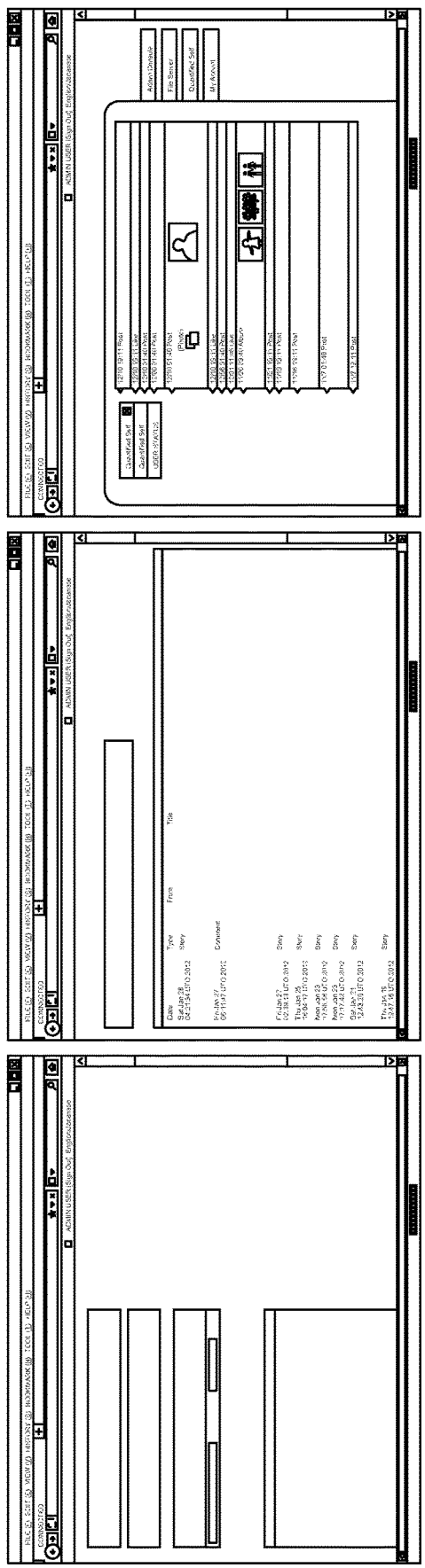
FIG. 18 is a diagram of the example of the behavioral records according to the embodiment.

An example of the behavioral records according to the present embodiment will be explained with reference to FIGS. 17 and 18. FIGS. 17 and 18 are diagrams of the example of the behavioral records according to the present embodiment.

The behavioral records shown in FIG. 17 are self-tracking data of daily events, and are data in which the user can easily keep a record by selecting a predefined visual symbol for a daily event or an emotion at the moment on a mobile terminal. By recording a short message as necessary, the user can think back on what event caused what emotion. These pieces of self-tracking data (record) may be data that is associated with the biological signals, such as brain waves and heartbeats, and in which visual symbols and messages, or the biological signal information (biological signals), are/is accumulated and can be reviewed daily, weekly, or monthly. In other words, according to the present embodiment, states can be recorded using mental and physical state symbols (emotions and events), which is not possible by conventional technologies.

The behavioral records shown in FIG. 18 are self-tracking data of social interaction on a social networking service (SNS), and are data obtained by taking behaviors of the user on Facebook (registered trademark) or Twitter (registered trademark) as data, and rearranging the data on the time axis. The self-tracking data may be text messages sent to the SNS by the user, text messages by other people following the user, messages sent on a mobile phone or a smartphone when the user exercised, ate, or went out, photographs, or data obtained by recording information on the web. The self-tracking data may be shared data of information posted by other people, or data obtained by recording information on attendance at or absence from events, and the like. Integrating these records and chronologically rearranging them in an easily understandable manner gives the user awareness about the behavioral characteristics.

Figure 19:
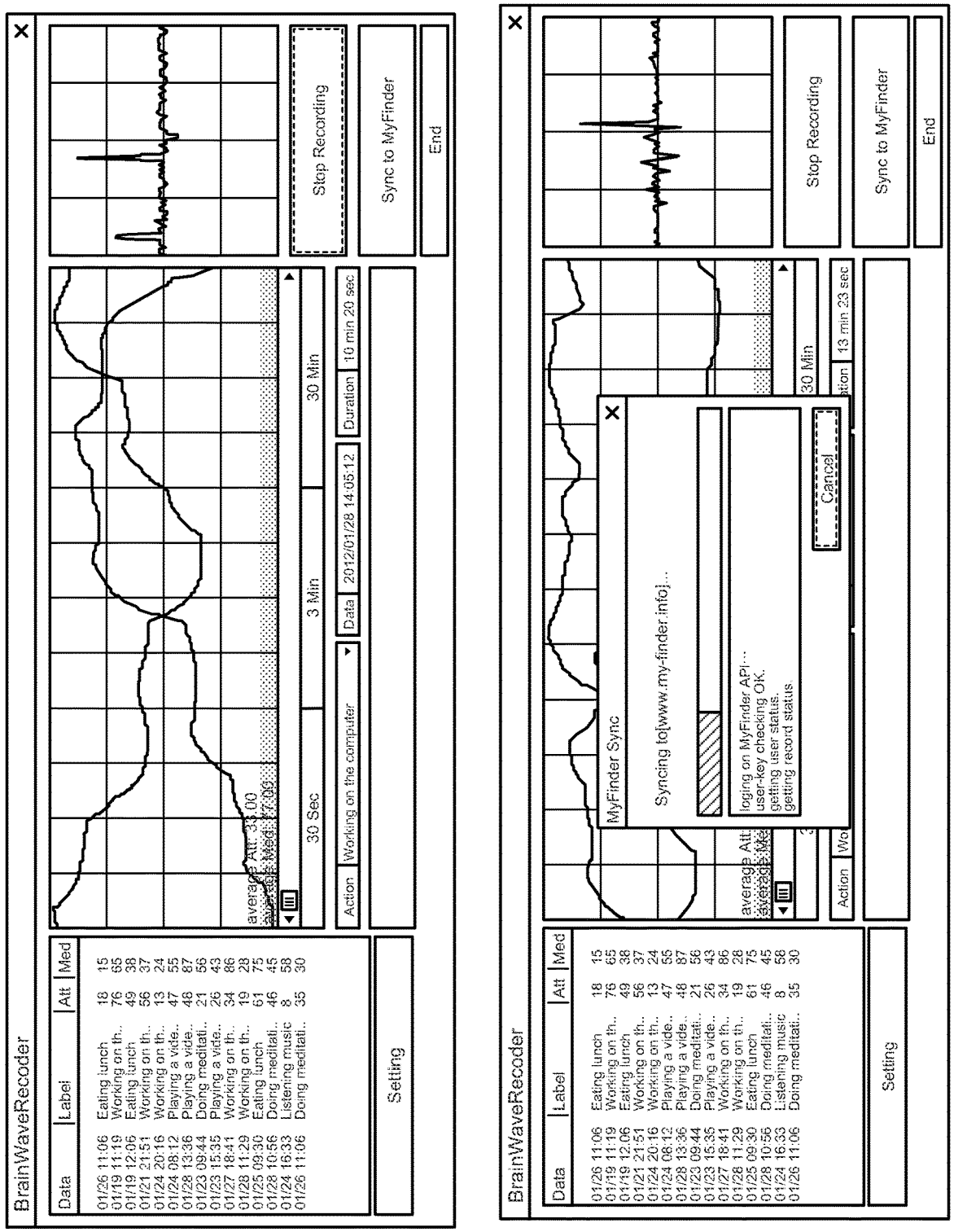
FIG. 19 is a diagram of an example of a biological signal acquisition according to the embodiment.

Examples of the biological signal acquisition according to the present embodiment will be explained with reference to FIGS. 19 and 20. FIGS. 19 and 20 are diagrams of the examples of the biological signal acquisition according to the present embodiment.

As shown in FIG. 19, if the monitoring device unit 112 of a mobile type (portable electroencephalogram (EEG) sensor) has self-tracked an electroencephalogram signal, the control unit 102 receives the electroencephalogram signal via a network (such as a wireless network), then classifies the signal into components of the degree of concentration and the degree of relaxation, and stores (downloads) the components together with the measured signal as raw data into the physical information record database 106b. As shown in FIG. 20, if the mobile monitoring device unit 112 (heartbeat sensor) has self-tracked a heartbeat signal, the control unit 102 receives the heartbeat signal via the network, and calculates three components representing coherence ratios while storing (downloading) the components together with the measured signal as raw data into the physical information record database 106b.

Examples of the mobile monitoring device unit 112 according to the present embodiment will be explained with reference to FIGS. 21 to 28. FIGS. 21 to 28 are diagrams of the examples of the mobile monitoring device unit 112 according to the present embodiment.

Figure 21:
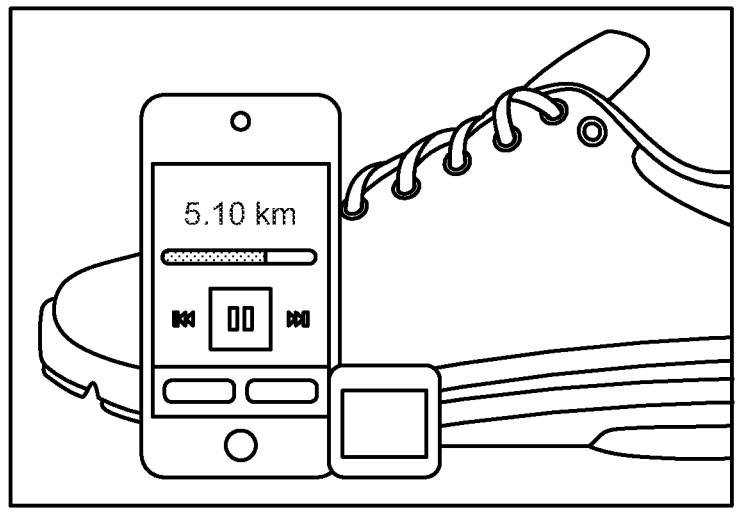
FIG. 21 is a diagram of an example of a mobile monitoring device unit according to the embodiment.
Figure 22:
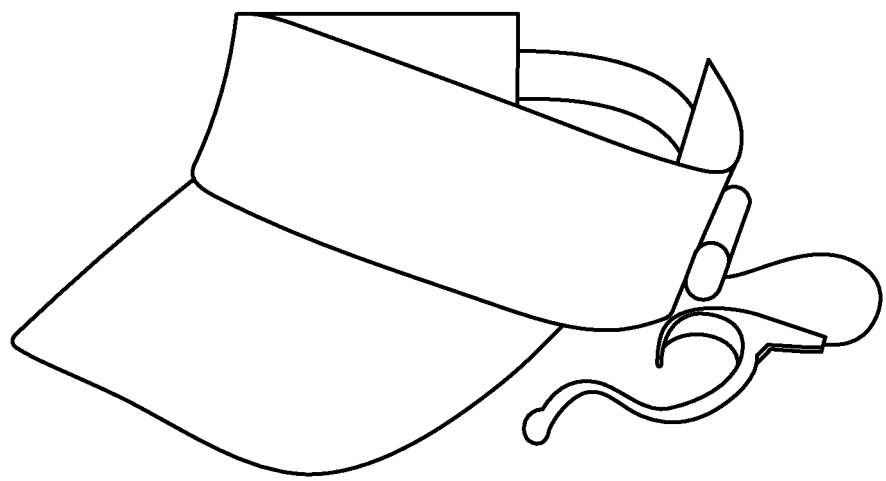
FIG. 22 is a diagram of an example of the mobile monitoring device unit according to the embodiment.
Figure 23:
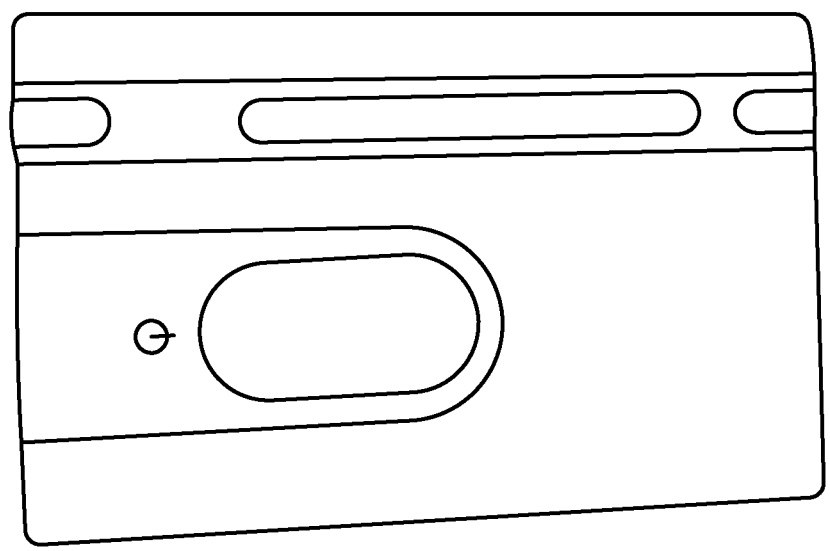
FIG. 23 is a diagram of an example of the mobile monitoring device unit according to the embodiment.
Figure 24:
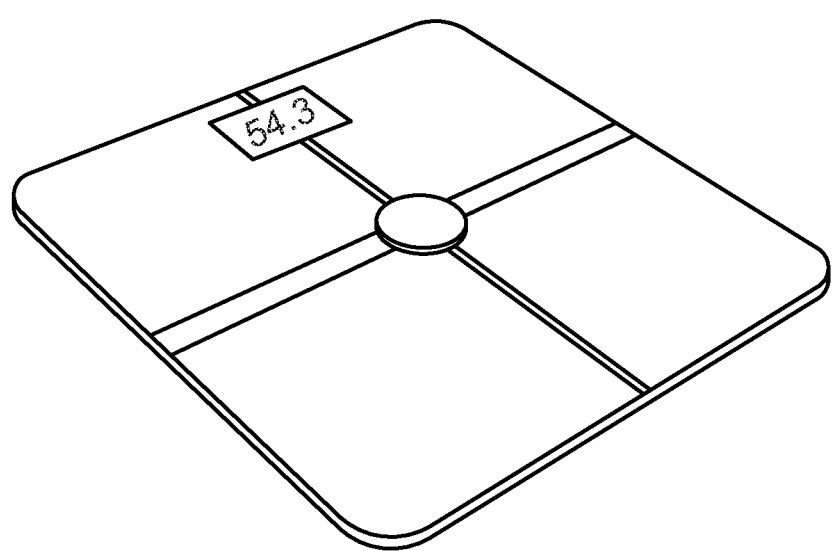
FIG. 24 is a diagram of an example of the mobile monitoring device unit according to the embodiment.
Figure 25:
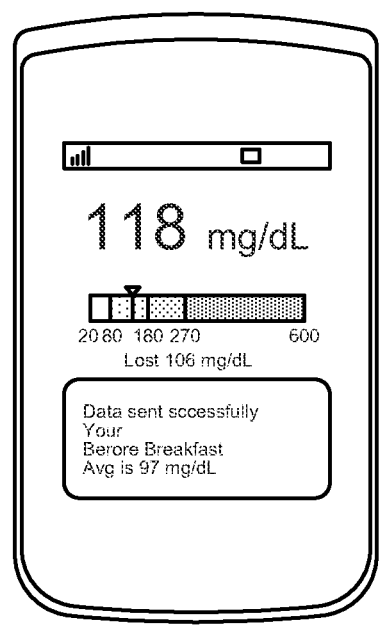
FIG. 25 is a diagram of an example of the mobile monitoring device unit according to the embodiment.
Figure 26:
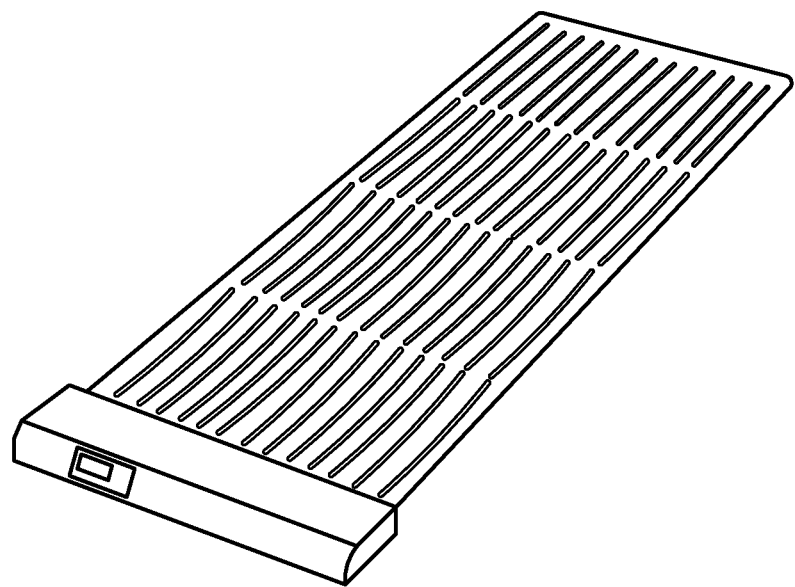
FIG. 26 is a diagram of an example of the mobile monitoring device unit according to the embodiment.
Figure 27:
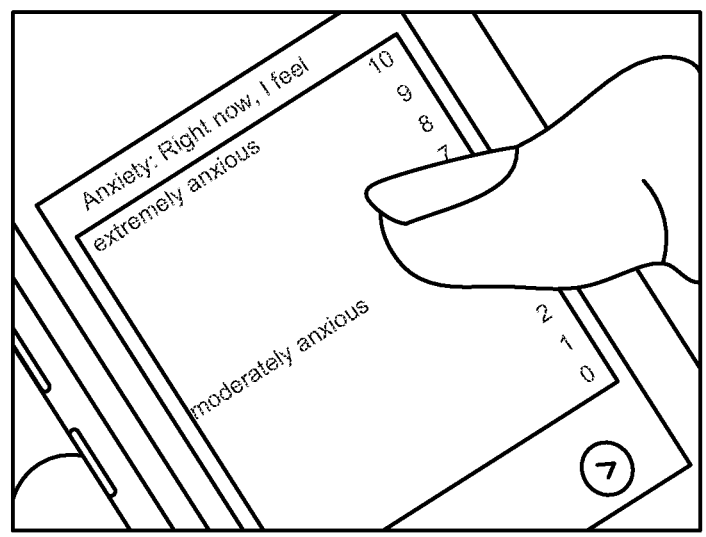
FIG. 27 is a diagram of an example of the mobile monitoring device unit according to the embodiment.
Figure 28:
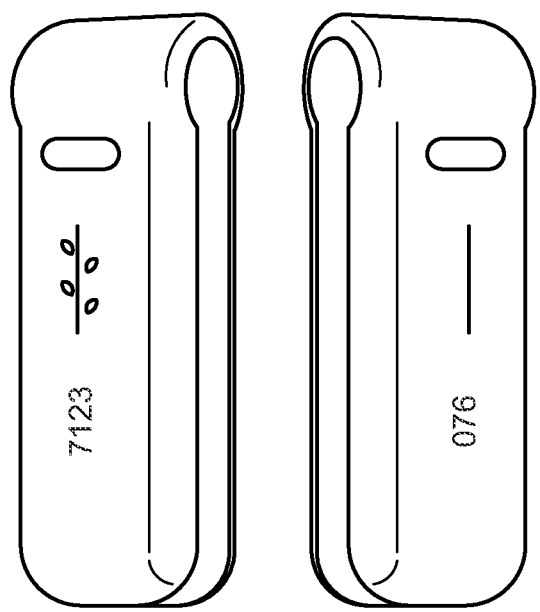
FIG. 28 is a diagram of an example of the mobile monitoring device unit according to the embodiment.

The mobile monitoring device unit 112 shown in FIG. 21 is a monitoring device that is mounted in a shoe, and measures data (such as the number of steps in a marathon and calorie consumption) related to the amount of exercise. The mobile monitoring device unit 112 shown in FIG. 22 is a monitoring device in the form of a sun visor that measures data (such as electroencephalographic data, and concentration and relaxation) related to the brain wave. The mobile monitoring device unit 112 shown in FIG. 23 is a monitoring device that is mounted on the chest or the like, and measures data (such as heartbeat data, and stress and relaxation) related to heartbeats. The mobile monitoring device unit 112 shown in FIG. 24 is a monitoring device that has a Wi-Fi function or the like, and measures data related to the body weight. The mobile monitoring device unit 112 shown in FIG. 25 is a monitoring device that measures data related to the blood sugar level. The mobile monitoring device unit 112 shown in FIG. 26 is a monitoring device that is used by being laid under the user during sleeping, and measures data (such as sleep data, sleep waveform data, and sleeping hours) related to sleeping. The mobile monitoring device unit 112 shown in FIG. 27 is a monitoring device that performs measurement of the state of mind of the user (such as mood tracking). The mobile monitoring device unit 112 shown in FIG. 28 is a clip-on pedometer, and is a monitoring device that measures the number of steps and the calorie consumption of the user.

In this manner, the present embodiment may, for example, perform simple acquisition of the self-tracking data in the non-medical field, and integration of the self-tracking data with the genetic information, which are not possible by conventional technologies.

Referring back to FIG. 6, the information integrating engine 102a acquires the self-tracking information (self-tracking data) obtained by integrating the behavioral records stored in the habit record database 106a and the biological signal stored in the physical information record database 106b (Step SC-2).

Figure 29:
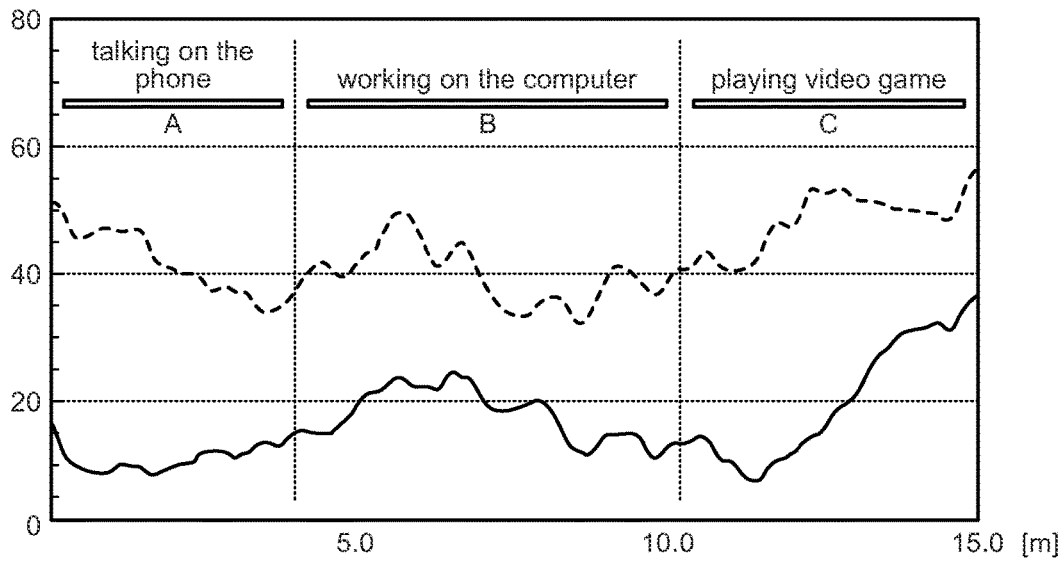
FIG. 29 is a diagram of an example of self-tracking information obtained by integrating the behavioral records and the biological signals according to the embodiment.

An example of the self-tracking information obtained by integrating the behavioral records and the biological signals according to the present embodiment will be explained with reference to FIG. 29. FIG. 29 is a diagram of the example of the self-tracking information obtained by integrating the behavioral records and the biological signals according to the present embodiment.

The self-tracking information shown in FIG. 29 is data obtained by mapping events that are the self-tracked behavioral records and electroencephalographic data that is the self-tracked biological signals, and can accumulate a tendency on what brain-wave pattern is obtained when the user is in what state. Specifically, in the self-tracking information shown in FIG. 29, the brain-wave patterns are mapped for the times when the user is talking on the phone, working on the computer, and playing a video game. In the self-tracking information shown in FIG. 29, both the degree of concentration and the degree of relaxation are high when the user is playing a video game. Accumulating such data and giving the user feedback can cause an expectation of helping the user to objectively understand the mental state of oneself, and to perform self-control. In other words, the present embodiment can associate the mental and physical state symbols (emotions and events), the biological signals, and the personal genome information with one another, which is not possible by conventional technologies.

In this manner, the present embodiment may, for example, provide the information integration technology for the self-tracking data in the non-medical field, which is not possible by conventional technologies.

The following explains an example of implementation of the information integrating engine (information integrating system) 102a in the self-tracking data acquisition according to the present embodiment.

First, personal attribute integration software (information integration server software and browser extension software) may be a storage unit (server) and a set of software for continuously accumulating and organizing various types of data of the user (such as sleep data, electroencephalographic data, and questionnaire data). The software may be composed of the following two components: a data collection agent built in a cloud, and extension software that acquires the state of the user in real time by using browser extension. The data collection agent may be data collection agents built on various platforms. Health monitoring devices (for sleep data, body weight data, and the like) used by the user may accumulate the collected data on web services provided by manufacturers of the respective devices. The data collection agent may be software that continuously acquires updated data by automatically logging in to the web services on behalf of the user using servers in the cloud, and sends the data to the control unit 102. The data collection agent may perform high-accuracy crawling and extraction using software that has a function of being capable of understanding an object-oriented scripting language and internally executing a simulation. Building the software in the cloud enables a response to an increase in the number of users in a low-cost and scalable manner.

The browser extension software may be browser extension software that extends the operation of a web browser, and may be activated when the browser has started and accessed an appropriate uniform resource locator (URL) and acquire user data (such as a brain wave or a pulse rate) connected to an information processing terminal, such as a personal computer (PC). When the user has answered a questionnaire or finished a work test on a web site, the browser extension software may acquire real-time electroencephalographic data and real-time pulse data of the user at the moment, and may send the data to the control unit 102 in a manner corresponding to the result of the questionnaire. The browser extension software may have an additional function so as to be capable of acquiring the electroencephalographic data, the pulse data, and image data obtained from a web camera or the like, and may further associate the data with an application programming interface (API) so as to be capable of corresponding to the data of the user.

A prototype of the present invention may be a platform that accumulates continuous health data of the user, results of replies to questionnaires, test scores of an appropriate work online, and electroencephalographic and pulse data at the time of reply. The prototype may function as a scalable data analysis cluster by being built in the cloud and implementing various types of analysis software. The prototype may be demonstration software that estimates personal attributes (genetic data and other attribute data) of the user from the accumulated data and also the current physical and mental state from continuously accumulated health data or the like, and interactively provides awareness potentially demanded by the user. The prototype of the present invention may provide appropriate information to the user and give the user natural enlightenment, and may also securely provide the accumulated data and the analysis tools to a citizen science group by using an API.

A cloud manager (cluster management software) may be a set of software that integrally manages computer instances. The computer instances may be a relational database that manages data, software for executing an API (file server/data providing server with authority management), software for data analysis, software for executing questionnaire software (a web server and a set of questionnaire software), and other software for data management. The cloud manager may collectively manage user information and authority information that use these instances, and may provide secure and integrated data access. The cloud manager may further provide an encryption function for highly confidential data, such as genetic data. Thus, the confidentiality of the data can be maintained according to the authority level by preventing the user from accessing the data unless the user uses the API software, and, in the event of data leakage, the confidentiality thereof can be maintained by encrypting the data.

Referring back to FIG. 6, the personal genome information acquiring unit 102*b* acquires the genetic information of the user, then acquires (obtains) the personal genome information that associates the genetic information with the genetic knowledge information, and stores the personal genome information in the personal genome knowledge database 106*c* (Step SC-3). The genetic information of the user may be entered by the user via the input unit 118, or may be received from the external system 200 via the network 300.

Figure 30:
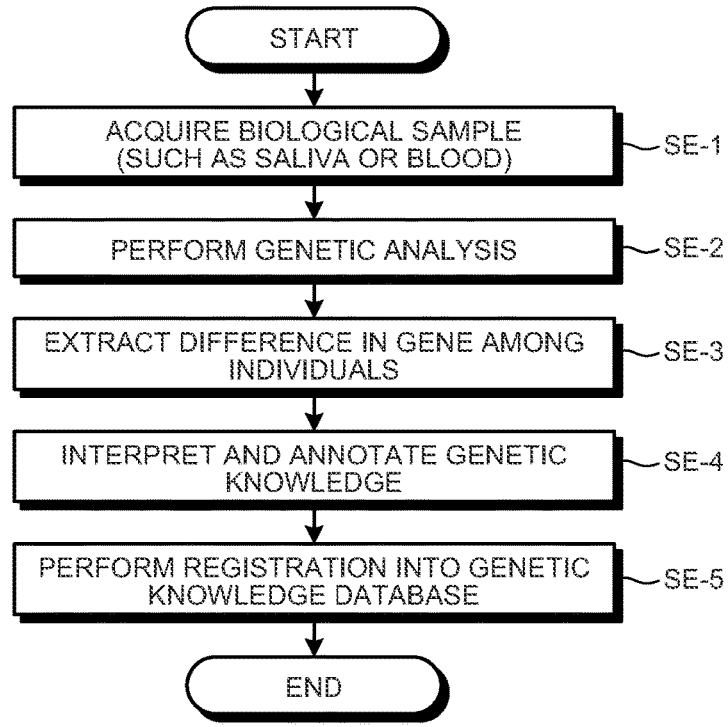
FIG. 30 is a flowchart of an example of processing by the personal genome information environment according to the embodiment.

An example of the personal genome information acquiring processing according to the present embodiment will be explained with reference to FIG. 30. FIG. 30 is a flowchart of the example of the processing by the personal genome information environment 100 according to the present embodiment.

As shown in FIG. 30, the personal genome information acquiring unit 102*b* acquires biological sample data about a biological sample, such as saliva or blood of the user (Step SE-1).

The personal genome information acquiring unit 102*b* then performs genetic analysis on the biological sample data acquired at Step SE-1 to obtain the genetic information of the user (Step SE-2).

The personal genome information acquiring unit 102*b* then extracts a difference in genes among individuals based on the genetic information of the user obtained at Step SE-2 (Step SE-3).

The personal genome information acquiring unit 102*b* then performs interpretation and annotation on the difference in genes among individuals extracted at Step SE-3 in terms of genetic knowledge by using the genetic knowledge information stored in the personal genome knowledge database 106*c* (Step SE-4).

The personal genome information acquiring unit 102*b* then acquires the personal genome information that associates the genetic information with the genetic knowledge information based on the annotation performed at Step SE-4, and stores (registers) the personal genome information in the personal genome knowledge database (genetic knowledge database) 106*c* (Step SE-5).

This is the end of the explanation for the example of the personal genome information acquiring processing according to the present embodiment.

Examples of data stored in the personal genome knowledge database 106*c* according to the present embodiment will be explained with reference to FIGS. 31 and 32. FIGS. 31 and 32 are diagrams of the examples of the data stored in the personal genome knowledge database 106*c* according to the present embodiment.

As shown in FIG. 31, the personal genome knowledge database 106*c* according to the present embodiment stores the genetic knowledge information about genes for each of which a relation to cognition, sensation, or behavioral characteristics has been reported. Specifically, the personal genome knowledge database 106*c* stores the genetic knowledge information that associates the genes, genetic variants, phenotypes influenced by the genetic variants, and papers suggesting statistical relativity of the influences with one another. For example, the personal genome knowledge database 106*c* stores the genetic knowledge information about oxytocin receptor (OXTR) as a gene affecting optimism, dopamine receptor D2 (DRD2) as a gene affecting extraversion, and catechol-O-methyl transferase (COMT) as a gene affecting altruism. While genetic research has conventionally focused on investigation of causes of diseases, preventive medical care, and examination of sick people for drug development, dramatic cost reduction and spread of genetic analysis technology have increased the possibility of discovering previously unfound new knowledge by investigating genes of healthy people.

As shown in FIG. 32, the personal genome knowledge database 106c according to the present embodiment stores the personal genome information that is a relative disease risk prediction (genetic diagnosis report) for type-2 diabetes of users (men of Asian ethnicity). In this manner, the disease risk prediction is relatively calculated under the influence of a plurality of genes, and may be calculated to have different values depending on due to the difference in the method for selecting the genetic variant, the influence of racial variation, and the difference in the method of risk calculation. An evaluation of reliability of the risk prediction and a prediction algorithm that takes the racial variation into account may also be provided.

In this manner, the present embodiment may, for example, perform interpretation of correlation between sensation, thinking, or behavioral characteristics, and a personal genome, which is not possible by conventional personal genome systems. The present embodiment may, for example, acquire personal genome information that associates genetic information and phenotype information related to developmental disorders or the like with each other, which is not possible by conventional technologies.

Referring back to FIG. 6, the information integrating engine 102d acquires the integrated information obtained by integrating the personal genome information stored in the personal genome knowledge database 106c and the self-tracking data acquired by the self-tracking information acquiring unit 102a (Step SC-4).

Figure 33:
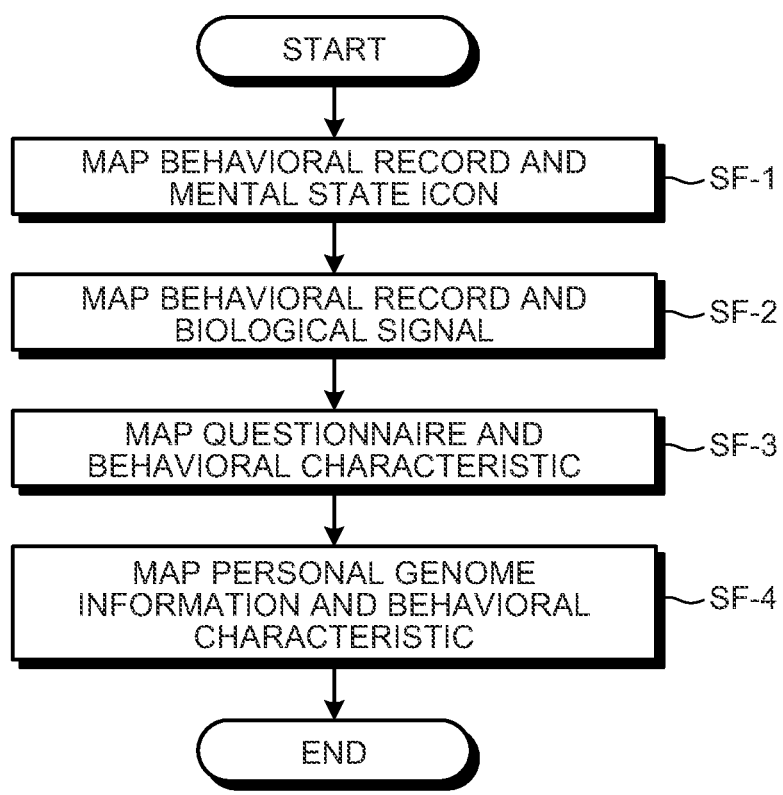
FIG. 33 is a flowchart of an example of processing by the personal genome information environment according to the embodiment.

An example of the information integration processing according to the present embodiment will be explained with reference to FIG. 33. FIG. 33 is a flowchart of the example of the processing by the personal genome information environment 100 according to the present embodiment.

As shown in FIG. 33, the information integrating engine 102d maps the behavioral records included in the self-tracking data and the mental state icons included in the self-tracking data on the body of the user (Step SF-1).

The information integrating engine 102d then maps the behavioral records included in the self-tracking data and the biological signals included in the self-tracking data on the body of the user (Step SF-2).

The information integrating engine 102d then maps data about the questionnaires included in the self-tracking data and the behavioral characteristics included in the self-tracking data on the body of the user (Step SF-3).

The information integrating engine 102d then maps the personal genome information stored in the personal genome knowledge database 106c and the behavioral characteristics included in the self-tracking data on the body of the user, then acquires the integrated information obtained by integrating the personal genome information and the self-tracking data (Step SF-4), and ends the processing.

This is the end of the explanation for the example of the information integration processing according to the present embodiment.

Figure 34:
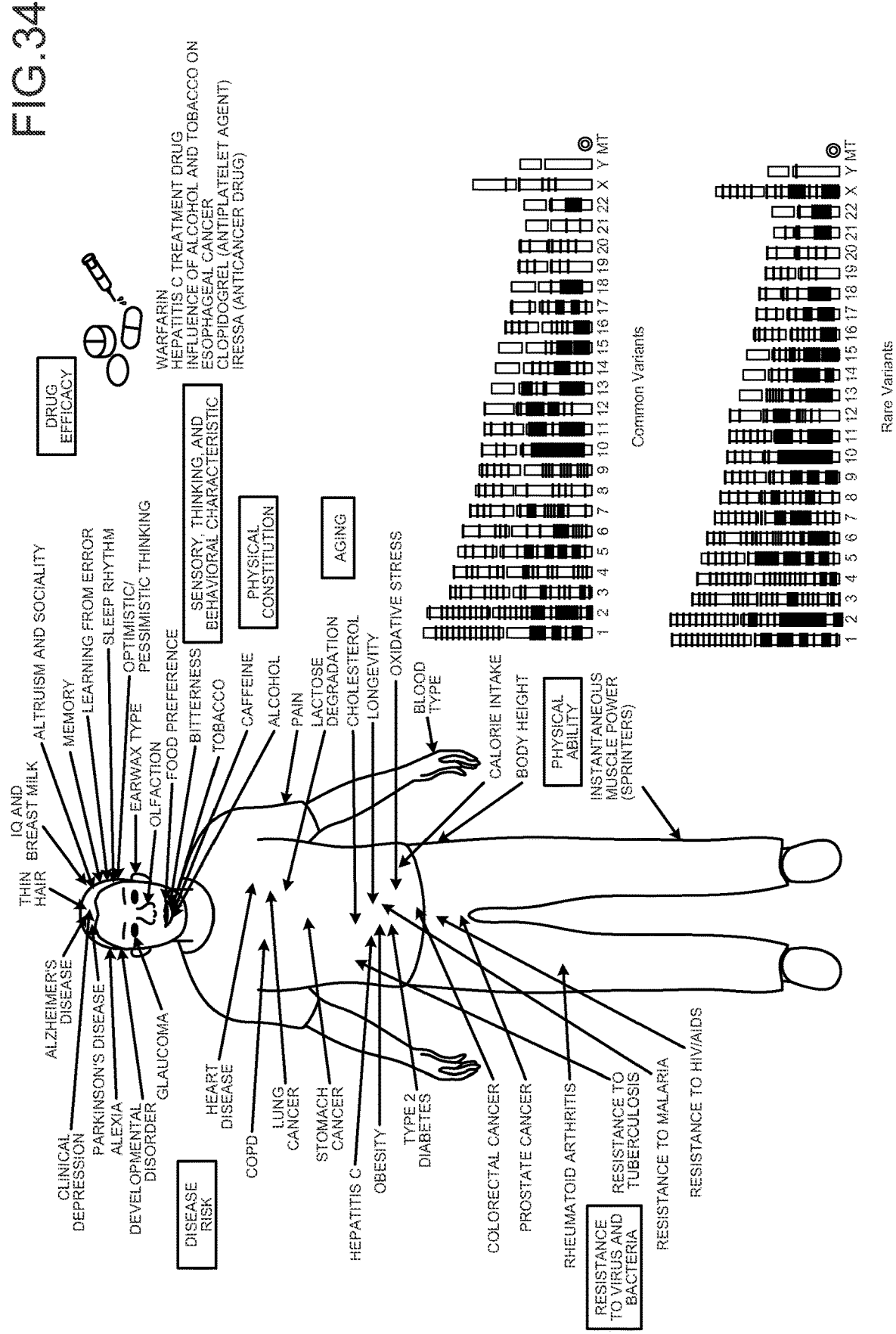
FIG. 34 is a diagram of an example of mapping according to the embodiment.

An example of the mapping according to the present embodiment will be explained with reference to FIG. 34. FIG. 34 is a diagram of the example of the mapping according to the present embodiment.

The left diagram of FIG. 34 is a map of a physical constitution and characteristics (disease risk, resistance to viruses and bacteria, drug efficacy, sensation, thinking, behavioral characteristics, physical constitution, aging, and physical abilities) related to genes according to the present embodiment on the human body. The right diagram of FIG. 34 depicts positions of genes on a human chromosome that increase or decrease the disease risk based on the physical constitution and the characteristics due to frequent mutation (common variants), and depicts positions of genes on the human chromosome that increase or decrease the disease risk based on the physical constitution and the characteristics due to infrequent mutation (rare variants). In other words, the present embodiment can associate the mental and physical state symbols (emotions and events) with the personal genome, which is not possible by conventional technologies.

Figure 35:
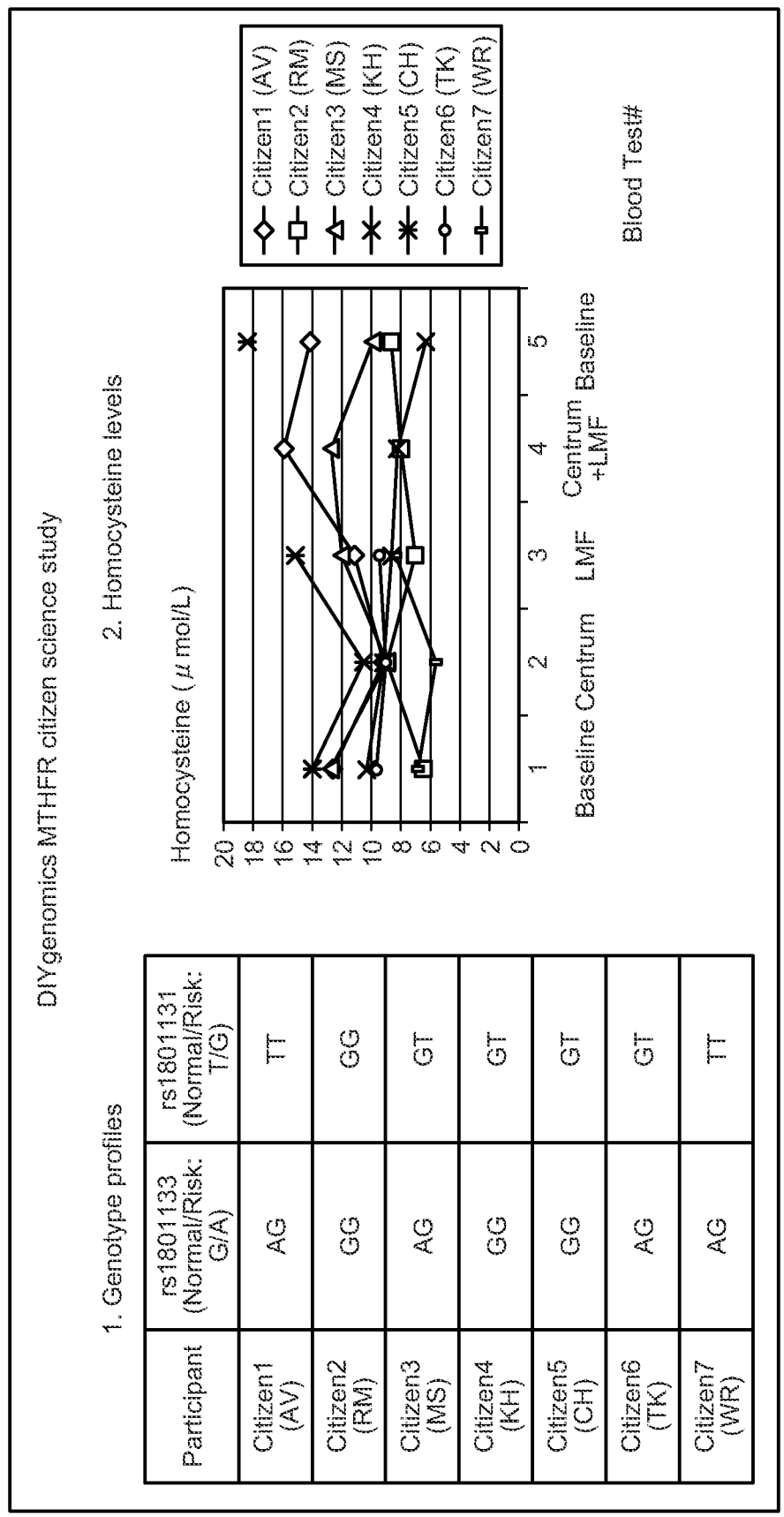
FIG. 35 is a diagram of an example of integrated information according to the embodiment.

An example of the integrated information according to the present embodiment will be explained with reference to FIG. 35. FIG. 35 is a diagram of the example of the integrated information according to the present embodiment.

FIG. 35 depicts the integrated information obtained by integrating genotype information and effect information on vitamin supplements (homocysteine levels in the blood). The genotype information serving as personal genome information is information that associates gene polymorphisms (genetic information) of seven participants who voluntarily gathered and participated in a survey for testing the effects of vitamin supplements with information about the metabolism of vitamin D depending on the difference in gene polymorphism, that is, information (genetic knowledge information) indicating that a person whose genetic variant corresponding to rs1801133 contains A, or a person whose genetic variant corresponding to rs1801131 contains G has a physical constitution that makes it difficult to metabolize vitamin D, and thus, a vitamin supplement of vitamin D is highly likely to be effective. The effect information on vitamin supplements serving as self-tracking data is a test result for the seven participants obtained by using an approach of citizen science. Specifically, the effect information on vitamin supplements is information obtained by performing the self-tracking on the homocysteine levels in the blood of the seven participants who have continually taken two types of vitamin supplements for two weeks. This led to observation of effects of the first vitamin supplement on six out of seven participants. The integrated information was obtained that indicates that the second vitamin supplement is effective for some people but not effective for the other people. This is an example indicating the possibility that participatory scientific projects can be carried out by citizen science.

In this manner, the present embodiment may, for example, use the genetic information of the user, which is not possible by conventional coaching systems or conventional biofeedback systems. The present embodiment may, for example, integrate the self-tracking data in the non-medical field and the genetic information, which is not possible by the conventional personal genome systems. The present embodiment may, for example, perform information integration between personal genomes and life-log information (self-tracking data), which is not possible by conventional technologies.

Referring back to FIG. 6, the data mining engine 102e acquires (obtains) the interactive knowledge information by performing the data mining on the integrated information acquired by the information integrating engine 102d (Step SC-5).

Figure 36:
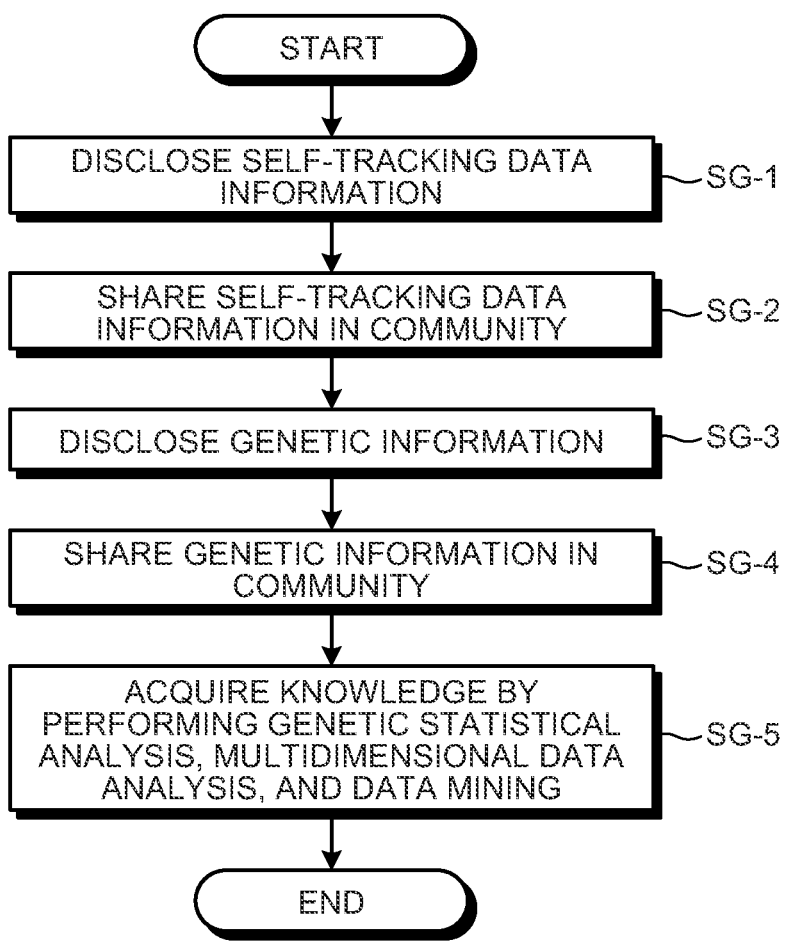
FIG. 36 is a flowchart of an example of processing by the personal genome information environment according to the embodiment.

An example of the data mining processing according to the present embodiment will be explained with reference to FIG. 36. FIG. 36 is a flowchart of the example of the processing by the personal genome information environment 100 according to the present embodiment.

As shown in FIG. 36, the data mining engine 102e discloses information of the self-tracking data included in the integrated information (Step SG-1).

The data mining engine 102e then shares information of the self-tracking data disclosed at Step SG-1 in the community (Step SG-2).

The data mining engine 102e then discloses the personal genome information (genetic information) included in the integrated information (Step SG-3).

The data mining engine 102e then shares the genetic information disclosed at Step SG-3 in the community (Step SG-4).

The data mining engine 102e then acquires the interactive knowledge information by performing the genetic statistical analysis, multidimensional data analysis, and the data mining (Step SG-5).

This is the end of the explanation for the example of the data mining processing according to the present embodiment.

Figure 37:
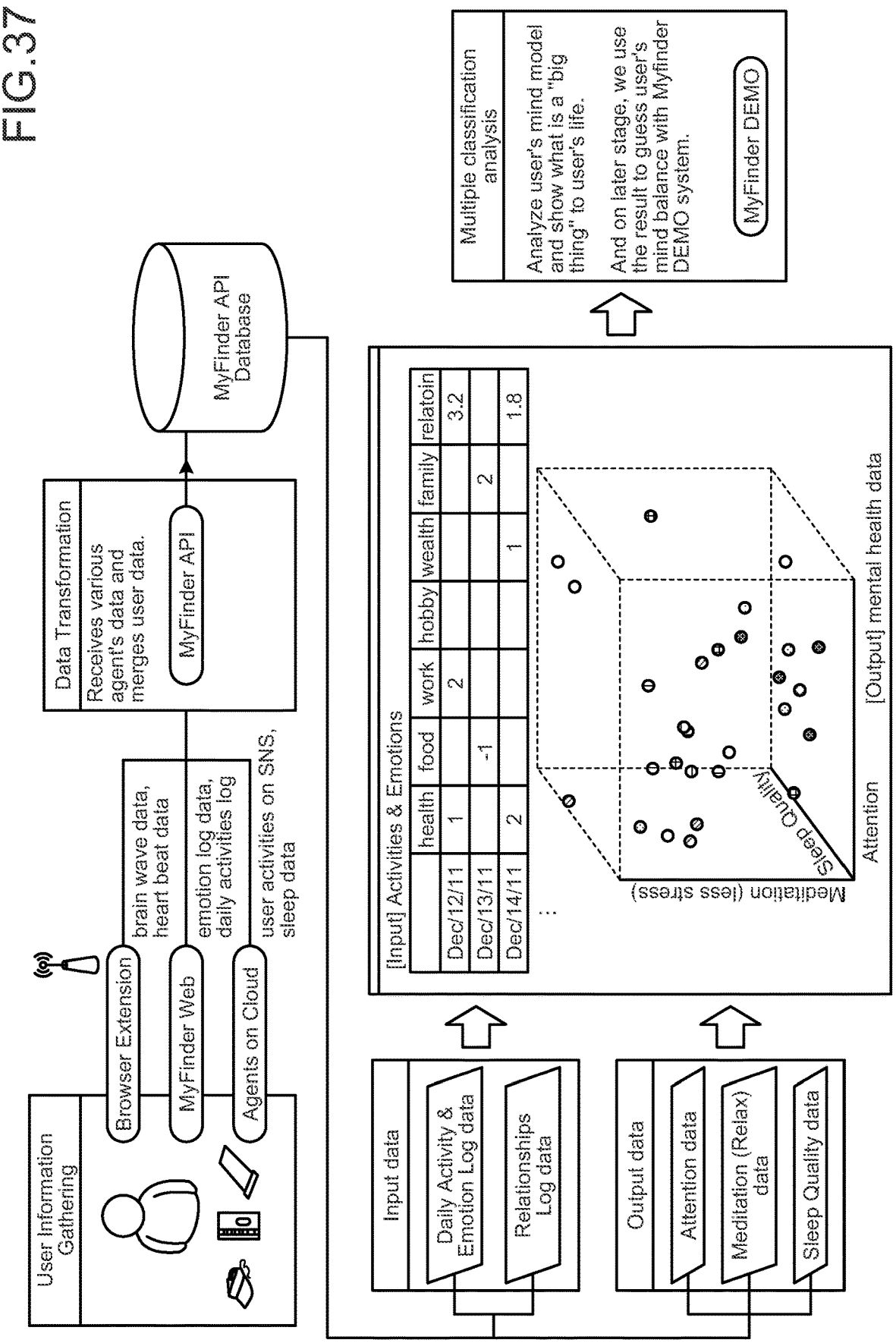
FIG. 37 is a diagram of an example of data mining processing according to the embodiment.

Another example of the data mining processing according to the present embodiment will be explained with reference to FIG. 37. FIG. 37 is a diagram of another example of the data mining processing according to the present embodiment.

As shown in FIG. 37, the data mining processing according to the present embodiment gathers data, such as the self-tracked daily event data, icons indicating emotional states, and electroencephalogram signals (concentration and relaxation), and analyzes relativity in a multidimensional space. The data mining processing according to the present embodiment also extracts patterns of cognitive characteristics and behavioral characteristics of a person, and examines relativity between the patterns and the personal genome information. This allows each person to become aware of the person's own tendencies so as to know the person's own mental state, behavioral characteristics, or physical constitutional tendencies, and can help the person to guide oneself toward a state in which the person is the happiest by performing self-control according to the characteristics.

In this manner, the present embodiment may, for example, perform analysis in the fields of sensation, thinking, and behavioral characteristics in the non-medical field, which is not possible by the conventional personal genome systems. The present embodiment may, for example, perform risk interpretation taking racial variations into account, which is not possible by the conventional personal genome systems. The present embodiment may, for example, analyze relativity between behavioral, sensory, or thinking characteristics and the differences in genes among individuals, which is not possible by conventional technologies.

Referring back to FIG. 6, the intelligent agent engine 102f presents the interactive knowledge information to the user by displaying the interactive knowledge information acquired by the data mining unit 102e on the display unit 114 (Step SC-6), and ends the processing. The intelligent agent engine 102f may output the interactive knowledge information acquired by the data mining unit 102e via the audio output unit 116.

Figure 38:
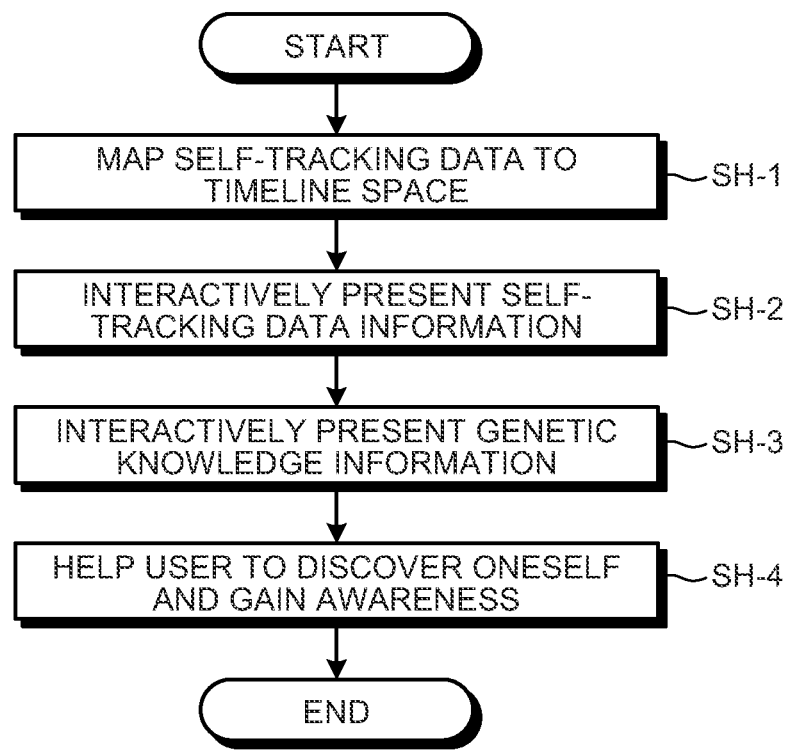
FIG. 38 is a flowchart of an example of processing by the personal genome information environment according to the embodiment.

An example of the interactive knowledge presentation processing according to the present embodiment will be explained with reference to FIG. 38. FIG. 38 is a flowchart of the example of the processing by the personal genome information environment 100 according to the present embodiment.

As shown in FIG. 38, the intelligent agent engine 102f maps the self-tracking data included in the interactive knowledge information to a timeline space (Step SH-1).

The intelligent agent engine 102f then interactively presents the information of the self-tracking data included in the interactive knowledge information (Step SH-2).

The intelligent agent engine 102f then interactively presents the information of the genetic knowledge included in the interactive knowledge information (Step SH-3).

The intelligent agent engine 102f then helps the user to discover oneself and gain awareness through the interactive information presentation performed at Steps SH-2 and SH-3 (Step SH-4).

This is the end of the explanation for the example of the processing by the personal genome information environment 100 according to the present embodiment.

Figure 39:
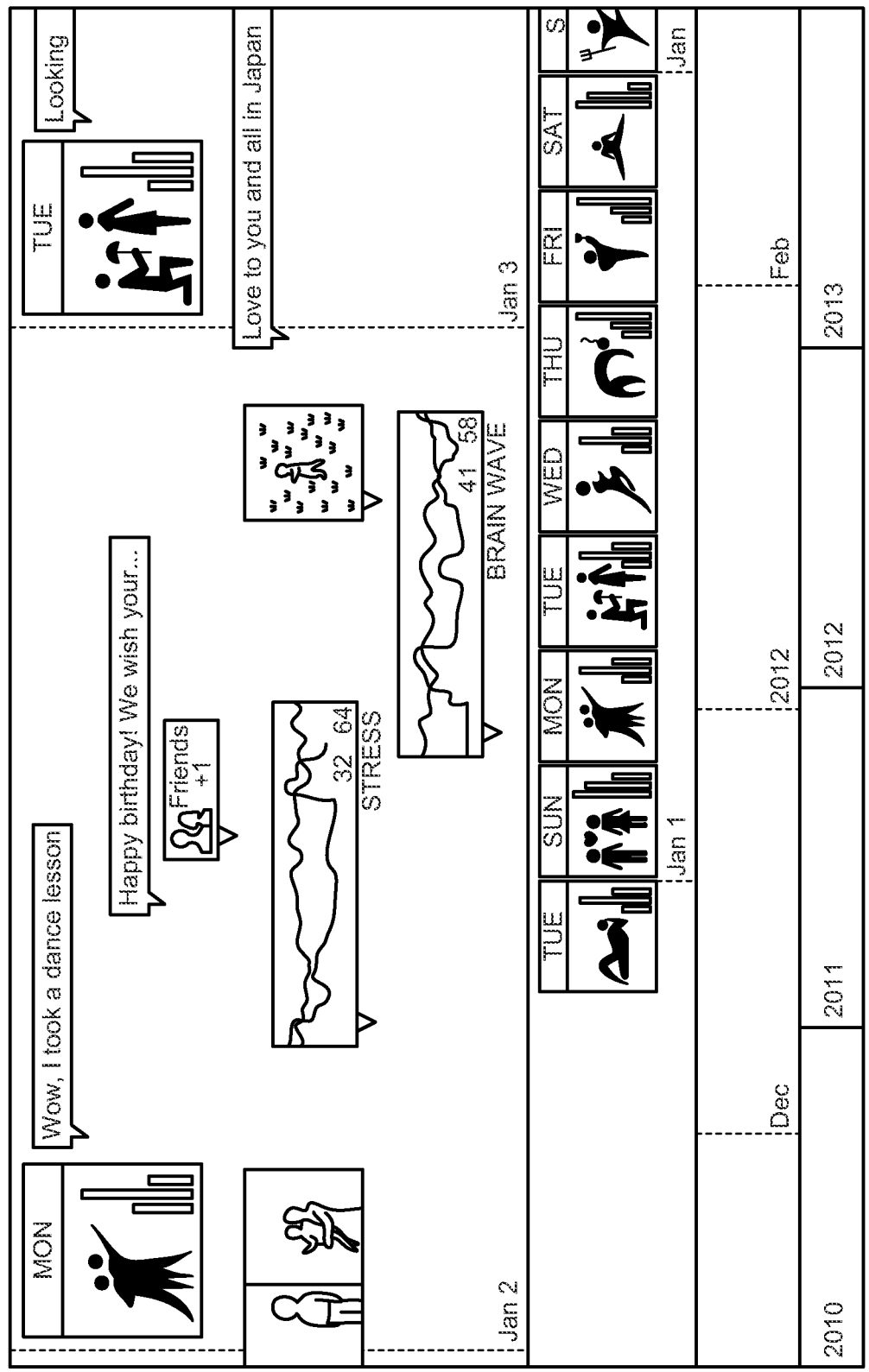
FIG. 39 is a diagram of an example of a display screen according to the embodiment.

An example of an interactive display in a self-tracking event according to the present embodiment will be explained with reference to FIG. 39. FIG. 39 is a diagram of the example of the display screen according to the present embodiment.

As shown in FIG. 39, the intelligent agent engine 102f associates daily events, emotions at the moments, and biological signals, such as brain waves and heartbeats, with one another, and reconstructs and interactively displays them along a timeline. Such a display allows the user to think back on what the user felt or thought and how the user biologically reacted in what situations. By displaying these pieces of self-tracking data along a daily, weekly, or monthly timeline, the user can be given awareness about the user's own behavioral characteristics, how to use time, tendency patterns of biological signals, or the like by habitually reviewing the record. By accumulating such patterns of behavioral characteristics, thinking characteristics, and cognitive characteristics, and the personal genome information in a manner associated with each other, and sharing them in a participatory scientific community, a platform can be provided for finding new roles of genes. In other words, the present embodiment can facilitate interactive self-discovery using an integrated display of time series events, mental and physical states, and biological signals in a chart form, which is not possible by conventional technologies.

In this manner, the present embodiment may, for example, have a function of helping the user to ask and answer the user's own questions and gain awareness, which is not available by conventional medical diagnosis systems. The present embodiment may, for example, have an interactive function of encouraging the user to gain awareness, which is not available by the conventional personal genome systems. The present embodiment may, for example, provide user modeling and policy selection based on reactions of the user about risk and benefit, which is not possible by conventional technologies. The present embodiment may, for example, have an interactive display function of the self-tracking data, which is not available by conventional technologies. The present embodiment may, for example, perform analysis of personal behavioral pattern and provide motivation to promote awareness using a dialogue board, which is not possible by conventional technologies. The present embodiment may, for example, achieve visualization of sensation, thinking, or behavioral characteristics, which is not possible by conventional technologies.

Citizen Science Project Using Present Invention

A specific example of a citizen science project using the present invention will be explained below.

In the present embodiment, by sharing in the community the data voluntarily self-tracked by each person using the present invention, a project can be carried out that leads to a new scientific discovery. In the present embodiment, this new participatory framework different from conventional methods is termed "citizen science". In the present embodiment, the present invention serves as the platform for actually carrying out a citizen science effort in this participatory community.

In the citizen science effort, data is accumulated by using various self-tracking devices related to health care and the like, and the project contributing to various scientific discoveries is carried out through the participatory online community. The self-tracking devices may be health and fitness applications for smartphones (such as myZeo that tracks sleep states, FitBit or BodyMedia that tracks calories burned and quality of sleep, a Scosche heart rate monitor, a Telcare product that measures glucose in blood, and a Withings weight scale). In the present embodiment, the citizen science effort can, for example, aim at doing research on relativity between sleep rhythm, diabetes, or personality, and genes by using these self-tracking devices. In each theme, finding a combined correlation between the personal genome information and the self-tracking data that are gathered in the present invention can cause an expectation of contribution to new scientific discoveries and application to improvement in health or prevention of illness, improvement in lifestyle habits, or behavior modification suited to a person.

The method for carrying out the citizen science effort may be such that the project is performed as a participatory cohort project by crowdsourcing (a method in which the general public are asked for participation in analysis via the Internet). In principle, participants are free to participate at participants' free will in the citizen science project, which is continuously carried out. The participants first check the informed consent, then agree to share genotypes of variants to be surveyed, and reply to the online survey. Feedback about new knowledge obtained by the citizen science effort may be individually made from the participatory community to the participants, as appropriate. For example, the participants may be able to apply for participation in various types of intervention research, such as improvement in sleeping habits and improvement in social intelligence skills.

The analysis step of citizen science may be carried out based on the following two-stage design. As a first stage, hypothesis formulation and hypothesis testing may be performed by analyzing whether results obtained in advance by the participatory scientific research through the crowdsourcing is reproduced. As a second stage, analysis may be made through the intervention research as to whether a causal relation holds in the relativity between a genetic variation found at the first stage and the hypothesis in question. Specifically, systematic analysis may be made as to whether differences in research results exist between a group where the genetic variation has occurred and a group where no genetic variation has occurred through the various types of intervention research using mobile applications or the like. Using such a framework of citizen science enables the following research designs.

As a first research design, the citizen science effort can carry out sleep rhythm research that investigates whether the genetic variation is related to the sleep rhythm of a person (such as short period/long period or morningness/eveningness). The present embodiment can test various hypotheses about the sleep rhythm by using sleeping habit records (phenotypes) and genetic data.

The present embodiment may test whether sleeping habits are improved through the intervention research. The intervention research may be performed by way of testing a hypothesis that, for example, wearing glasses that block blue light from two hours before bedtime reduces sleep latency and increases slow-wave sleeping hours. These can be evaluated, for example, by a combination of myZeo data, genotype data, and a questionnaire survey. Personal knowledge can be shared among community members by extracting data from the self-tracking devices or self-monitoring experiences of the participants.

The self-tracking data useful in these types of research may be as explained below. The phenotype data may be morningness-eveningness questionnaire (MEQ) data, Pittsburgh sleep quality index (PSQI) questionnaire data, insomnia severity index (ISI) data, myZeo data, ActiGraph data, or the like.

The genetic data related to the sleep research may be as explained below. Of single nucleotide polymorphisms (SNPs) affecting sleep, caffeine-related SNPs may be cytochrome P450, family 1, subfamily A: CYP1A2: rs762551, rs2472297; aryl hydrocarbon receptor (AHR): rs4410790; adenosine deaminase (ADA): rs73598374; or the like.

The SNPs related to healthy sleep profiles may be adenosine A2a receptor (ADORA2A): rs5751876; period 3 (PER3): rs57875989, rs228697, AB047536 5-repeat, rs10462021; period 2 (PER2): rs2304669; adenosine deaminase (ADA): rs73598374; brain-derived neurotrophic factor (BDNF): rs6265; catechol-O-methyltransferase (COMT): rs4680 (Val158Met); prion protein preproprotein (PRNP): rs1799990; aryl hydrocarbon receptor nuclear (ARNTL): rs95215856; aryl hydrocarbon receptor nuclear 2 (ARNTL2): rs5797225, rs7137588, rs4964059; CLOCK: rs1801260, rs95215860; arylalkylamine N-acetyltransferase (AANAT): rs4238989; glutamate receptor, ionotropic, alpha-amino-3-hydroxy-5-methyl-4-isoxazole propionate 3 isoform (GRIA3): rs687577; or the like.

The SNPs related to sleep disorders may be T cell receptor alpha-chain C region (TCRA): rs1154155; purinergic receptor P2Y11 (P2RY11): rs2305795, rs4804122; thyrotropic embryonic factor (TEF) isoform 1: rs738499; serotonin 2A receptor (5-HT2A): rs6311; or the like.

An example (improvement to comfortable sleeping habits suited to a person) of citizen science performed by self-tracking of sleep and behavioral data according to the present embodiment will be explained with reference to FIGS. 40 to 45.

Figure 40:
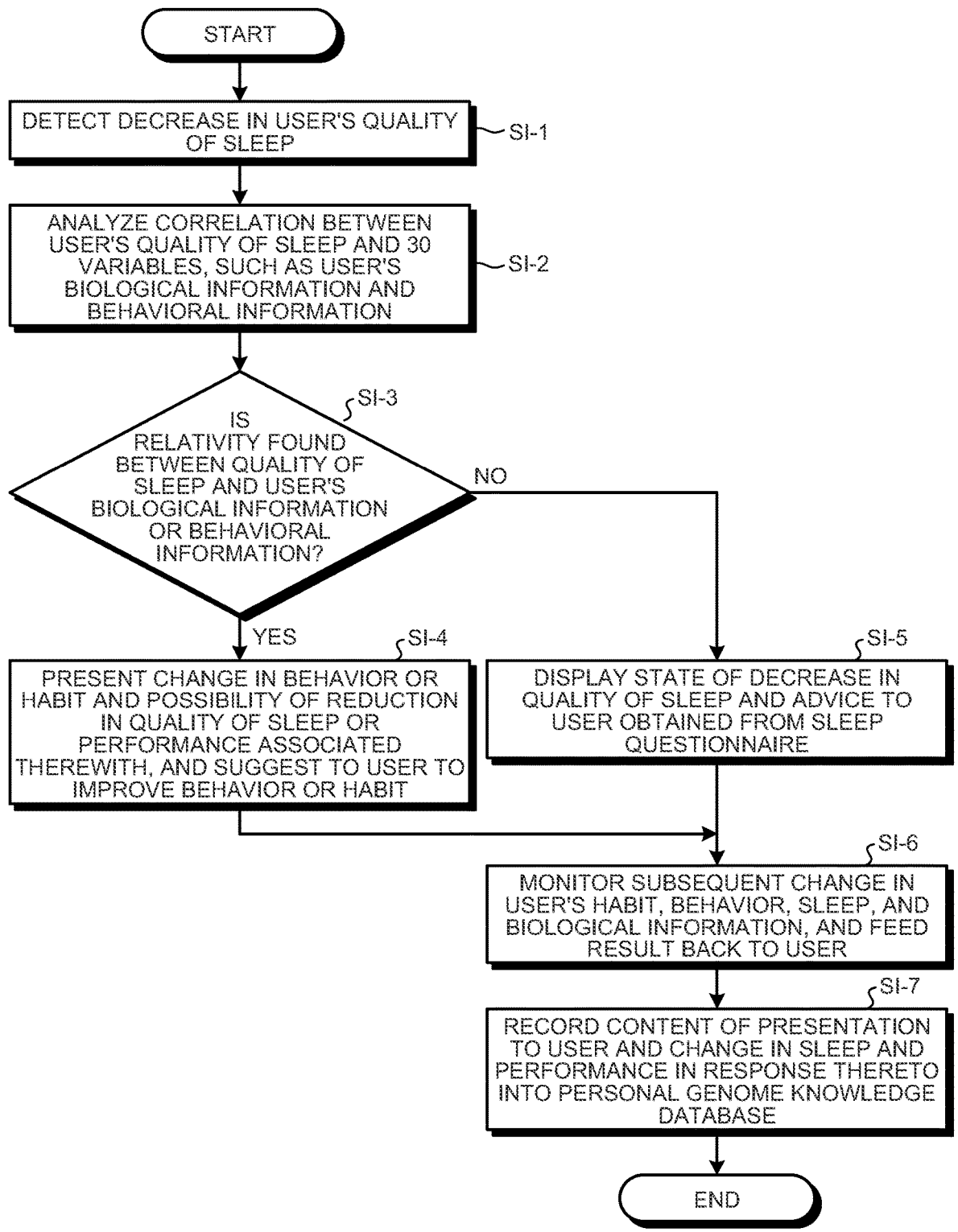
FIG. 40 is a flowchart of an example of processing in citizen science performed by self-tracking of sleep and behavioral data according to the embodiment.

The example of processing in citizen science by the self-tracking of sleep and behavioral data according to the present embodiment will first be explained with reference to FIG. 40. FIG. 40 is a flowchart of the example of the processing in citizen science performed by the self-tracking of sleep and behavioral data according to the present embodiment.

As shown in FIG. 40, the self-tracking information acquiring unit 102a uses the monitoring device unit 112 to perform the self-tracking of the behavioral data (sleep data) of the user, and detects a decrease in quality of sleep of the user (Step SI-1), and the information integrating engine derives an indicator that defines the quality of sleep (sleep efficiency), and presents the time-series change of the index to the user. The sleep data obtained by the monitoring device unit 112 may be temporal change in wakeup time, level 1 sleeping hours (shallow sleep), level 2 sleeping hours (deep sleep), or waking hours.

Other behavioral data self-tracked by the monitoring device unit 112 may be: biological information (brain wave, heartbeat, or body weight); behavioral information (calorie consumption or number of steps); habit information (bedtime, wakeup time, or depth of sleep); human relation information (interaction data on SNS); information on operational behavior on PC (input speed and error rate with keyboard and mouse); or emotional information (self-declared extraction of emotion using icons); or a body weight, a body mass index (BMI), a body fat percentage, a skeletal muscle rate, a basal metabolism, a visceral fat level, a physical age, activity calories, total calorie consumption, an exercise distance, fat burned, a basal body temperature, whether appetite has increased, whether irritated, whether supplement was taken, whether sleepy at daytime, bedtime, hours in bed, sleeping hours, whether edema is present, or the like.

An example of sleep-related data obtained by the monitoring device unit 112 according to the present embodiment will be explained with reference to FIG. 41. FIG. 41 is a diagram of an example of graphs of changes in the sleep-related data obtained by the monitoring device unit 112 according to the present embodiment.

As shown in FIG. 41, the monitoring device unit 112 according to the present embodiment can perform the self-tracking of the bedtime, the level 1 sleeping hours, the level 2 sleeping hours, and the waking hours of the user.

Figure 42:
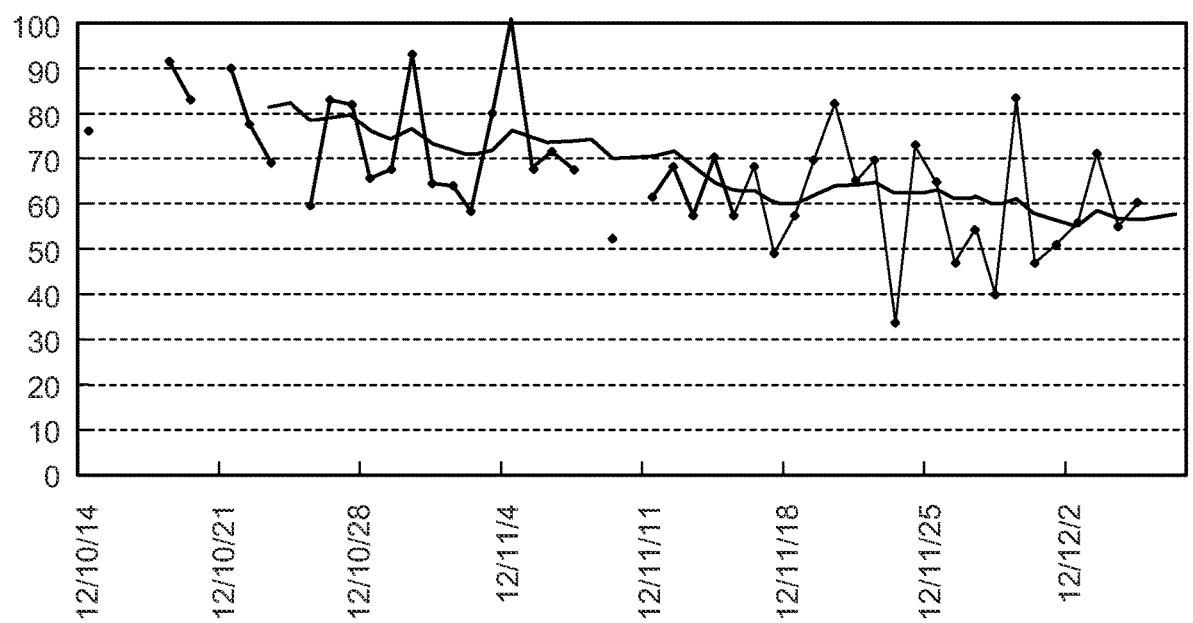
FIG. 42 is a diagram of an example of an information presentation according to the embodiment.
Figure 43:
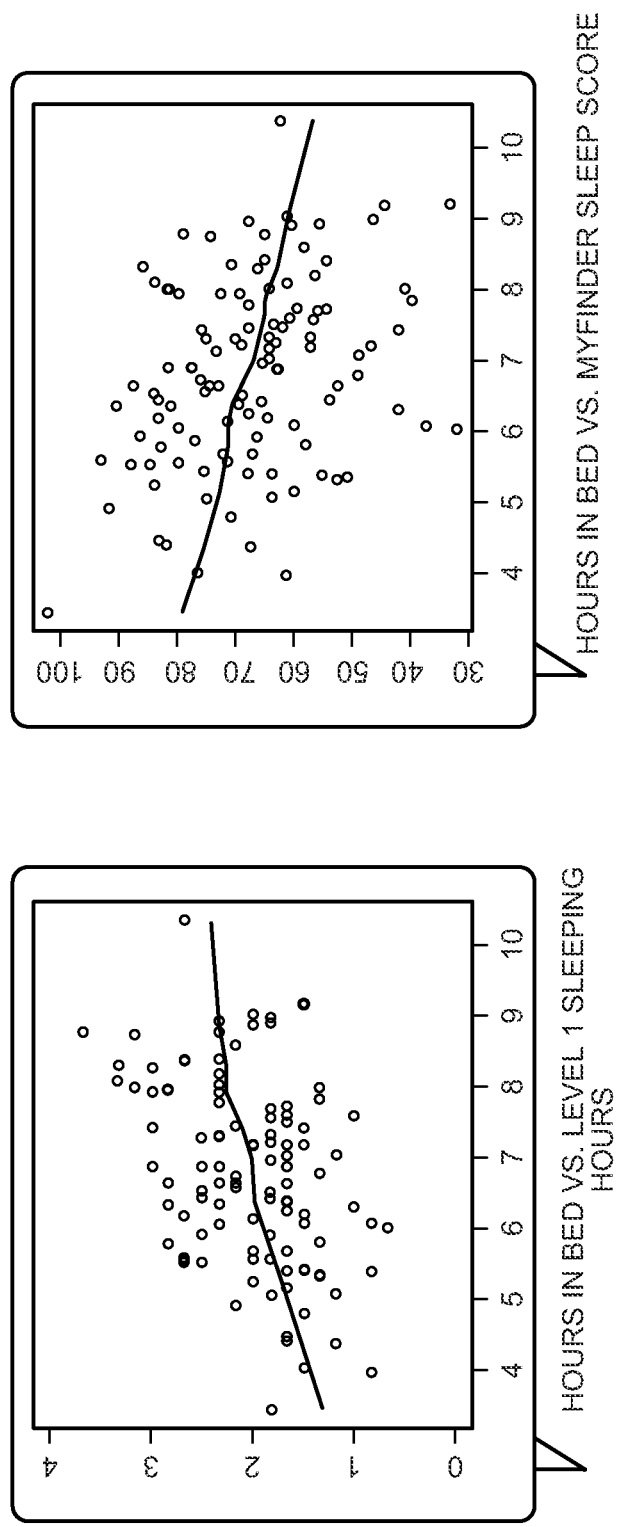
FIG. 43 is a diagram of an example of the information presentation according to the embodiment.

Examples of an information presentation function according to the present embodiment will be explained with reference to FIGS. 42 and 43. FIGS. 42 and 43 are diagrams of the examples of the information presentation according to the present embodiment.

The information presentation function implemented by the information integrating engine according to the present embodiment allows the user to interactively obtain various information displays. As shown in FIG. 42, the information integrating engine may derive MyFinder sleep scores that define the quality of sleep, and may present time-series changes in the MyFinder sleep scores. In other words, the information integrating engine finds out noteworthy indicators and derives the indicators of the sleep efficiency.

The control unit 102 may automatically derive the MyFinder sleep scores as indicators interpretable as the sleep efficiency from the self-tracking data, such as any one, some, or all of the sleeping hours, the level 1 sleeping hours (shallow sleep), the level 2 sleeping hours (deep sleep), and the waking hours. The sleep efficiency may be an indicator obtained by weighting the ratio of time in which the brain is actually in a deep sleep stage in the sense of electroencephalogram analysis to total hours in bed by a parameter. As shown in FIG. 42, the sleep scores have been observed to keep decreasing in a time series manner. Why the sleep scores decrease, and how they can be increased remain to be solved.

As knowledge obtained from the data analysis in the present embodiment, characteristic tendencies of sleeping habits have been obtained by interactively investigating the relativity of data. For example, by plotting the data for two months with the sleep efficiency on the vertical axis and the hours in bed on the horizontal axis, it has been found that the sleep efficiency decreases as the hours in bed increases. It has also been found that the level 1 sleeping hours (shallow sleep) increase as the hours in bed increase. However, the sleep efficiency does not necessarily increase (long sleep does not increase the sleep efficiency), thereby suggesting a possible room for further increase in the sleep efficiency. It has also been found that the sleep efficiency has no relation with the time of going to bed. An investigation of whether the sleep efficiency has regularity has found that a characteristic variation can be found in patterns of the sleep rhythm when the lifestyle rhythm greatly varies between weekends and weekdays as in the case of corporate employees. It has, however, been found that no characteristic pattern can be found by visualizing the sleep rhythm with a heat map in the case of a user whose lifestyle rhythm does not vary between weekends and weekdays.

As shown in FIG. 43, the information integrating engine may present to the user a change in the level 1 sleeping hours with respect to the hours in bed, or a change in a MyFinder sleep score with respect to the hours in bed.

Referring back to FIG. 40, the data mining engine (data mining unit) 102e analyzes correlations between the quality of sleep of the user and 30 variables, such as the biological information and the behavioral information of the user (Step SI-2).

Figure 44:
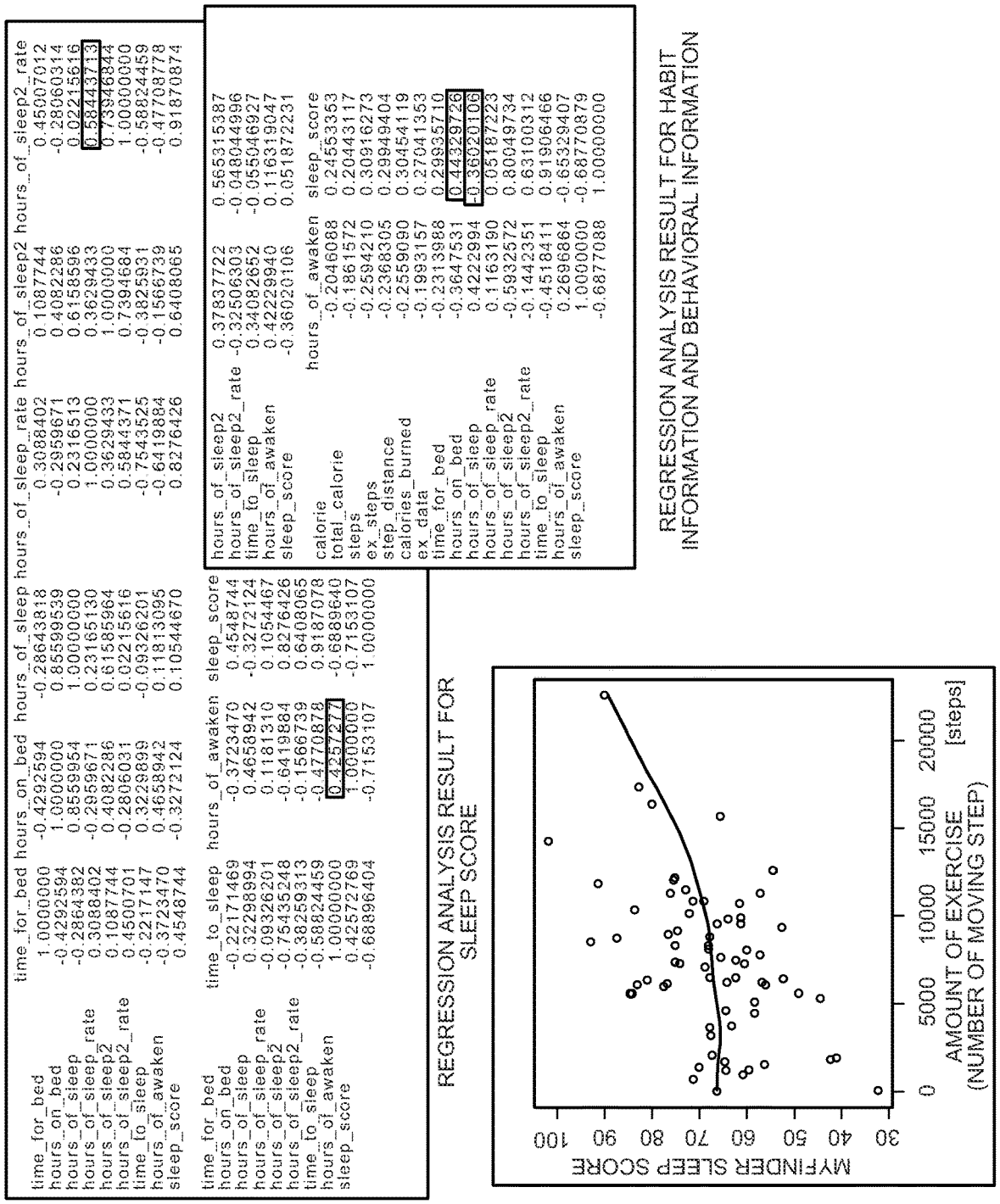
FIG. 44 is a diagram of an example of analysis results obtained by a data mining engine according to the embodiment.

An example of data mining on the sleep data performed by the data mining engine 102e according to the present embodiment will be explained with reference to FIG. 44. FIG. 44 is a diagram of an example of analysis results obtained by the data mining engine 102e according to the present embodiment.

As shown in FIG. 44, the data mining engine 102e can find out behavioral indicators that have been found to have relativity with the quality of sleep by performing regression analysis on the sleep scores, the habit information, or the behavioral information. In other words, the data mining engine 102e can perform analysis and possibility study of correlation among the data. Specifically, as shown in FIG. 44, the data mining engine 102e may analyze correlation of the 30 variables, and may automatically extract highly correlated variables. That is, a part of the execution example using a correlation matrix is shown in FIG. 44, in which a correlation between the amount of exercise and sleep is strongly detected. In particular, two correlations shown in FIG. 44 have been found that can lead to a hypothesis. A hypothesis has been presented that the sleep efficiency is increased by improving two elements based on (1) the correlation between the daily amount of exercise and the sleep score, and (2) the correlation between the bedtime and the sleep score. The related personal genome knowledge database 106c has suggested a possible contribution of blocking of the blue light before bedtime to improvement in the sleep score.

Referring back to FIG. 40, the control unit 102 determines whether relativity is found between the quality of sleep and the biological information or the behavioral information of the user (Step SI-3).

If the control unit 102 has determined that relativity is found between the quality of sleep and the biological information or the behavioral information of the user at Step SI-3 (Yes at Step SI-3), the intelligent agent engine 102f presents a change in behavior or habit and a possibility of reduction in quality of sleep or performance associated therewith, and after suggesting to the user to improve the behavior or the habit (Step SI-4), performs processing at Step SI-6. This causes the user to interactively consider sleep habits suited to the user, and advance the consideration in a trial-and-error manner.

If the control unit 102 has determined that relativity is not found between the quality of sleep and the biological information or the behavioral information of the user at Step SI-3 (No at Step SI-3), the intelligent agent engine 102f displays the state of decrease in the quality of sleep and advice to the user obtained from the sleep quality index questionnaire on the display unit 114 (Step SI-5).

The control unit 102 then uses the monitoring device unit 112 to monitor changes thereafter in the habit, the behavior, the sleep, and the biological information of the user, and feeds the results back to the user (Step SI-6).

The control unit 102 then records the content of presentation to the user and a change in sleep performance in response thereto into the personal genome knowledge database 106c (Step SI-7), and ends the processing. This allows the recorded data to be shared in the community, and the user to participate in the citizen science project for testing various hypotheses to explore relations between the recorded data and effectiveness of sleeping habits or genes.

Figure 45:
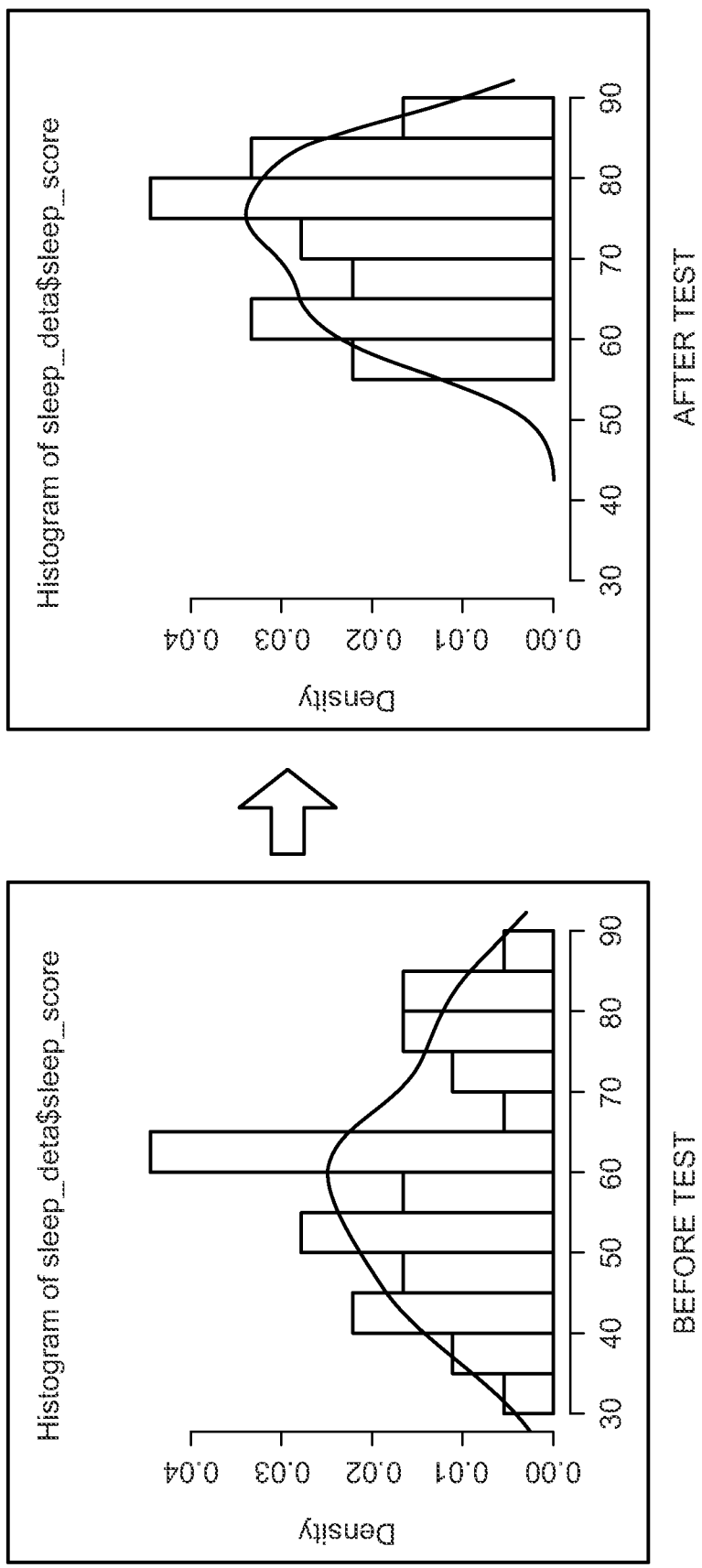
FIG. 45 is a diagram of an example of sleep scores before and after an action plan according to the embodiment is executed.

An example of an action plan based on a hypothesis obtained by the data mining according to the present embodiment will be explained with reference to FIG. 45. FIG. 45 is a diagram of an example of the sleep scores before and after the action plan according to the present embodiment is executed.

As the hypothesis obtained by the data mining according to the present embodiment, a hypothesis was set up such that the quality of sleep is changed by a change in lifestyle habit, such as taking an exercise of ten thousand or more steps a day on average, wearing blue light blocking glasses, limiting the use of a PC (not using a smartphone) 1.5 to 3 hours before bedtime, and taking a supplement. The hypothesis was tested.

In the present embodiment, the "change in the quality of sleep" was tested by comparing the distribution of the sleep scores between before and after the test. As shown in FIG. 45, the sleep scores are higher as a whole after the test is conducted, which shows that the quality of sleep has been improved, that is, the hypothesis has been proved. Specifically, the sleep scores have increased by 12 percent as a result of the change in the lifestyle habit. More specifically, the user has become aware from the actual self-tracking data that the sleep efficiency has been continuously decreasing, and has changed the lifestyle habit on the hypothesis set up for increasing the sleep efficiency; as a result, the user has been able to increase the sleep efficiency. This is a result of the fact that the user has changed the behavior and the mind by gaining awareness from the daily self-tracking data. Use of blue light blocker lenses, stopping using a PC for several hours before sleeping, and the like are highly likely to have caused the change in the quality of sleep. There is an expectation of future clarification through the citizen science effort as to which element has contributed to the improvement in the quality of sleep to what extent, and as to whether such change in the quality of sleep is merely an individual effect or is effective in general.

In this manner, carrying out the citizen science effort about the sleep rhythm is expected to formulate various hypotheses about the sleep rhythm, and test the hypotheses. In particular, applying the present invention allows the citizen science effort to be carried out about the relation between optimal sleeping hours or a tendency as to morningness or eveningness and a biological clock rhythm or genes.

In the present embodiment, using the present invention has succeeded in improving the quality of sleep by tracking behavioral data of a user (female participant in her 20's) for four months (from October 2012 to February 2013) for obtaining comfortable sleep, and by having her gain awareness by analyzing the data. In the present embodiment, the project was carried out in order for the user to obtain comfortable sleep (to increase the efficiency of deep sleep suited to the user) under the motivation of increasing the sleep efficiency, improving the quality of sleep based on the self-tracking data, finding an improvement plan of the sleeping habits, and the like.

As a second research design, the citizen science effort can carry out obesity and type 2 diabetes prevention research that investigates whether physical constitutional elements due to genetic variation are related to the risk of obesity or diabetes of a person. Various hypotheses about obesity or diabetes can be tested by using records (phenotypes) about dietary life and change in the blood sugar level and genetic data.

The present embodiment can test whether the body weight or the blood sugar level is improved by change in the dietary habit, such as restriction on eating before going to bed, exercising, a diet program, or the like, as a method for intervention. Measurement of the blood sugar level may be performed by performing self-tracking of blood glucose using a Telcare product. As a hypothesis test using genetic data, relations with SNPs related to insulin resistance clarified by intervention research in prior research may be investigated. The voluntary participation in the citizen science effort using simple self-tracking devices is expected to enhance consciousness of participants to prevention, and to cause active change in awareness and behavior through sharing of various self-monitoring experiences in the community.

The genetic data related to these diabetes research activities may be as explained below. Of SNPs affecting diabetes, the SNPs related to the heart rate during resting may be catechol-O-methyltransferase (COMT): rs4680$^3$ (Val158Met); connexin 43 (GJA1): rs9398652, rs11154022; myosin heavy chain 6 (MYH6): rs452036, rs365990; myosin heavy chain 7 (MYH7): rs223116; intergenic region: rs17287293; solute carrier family 35 member F1 (SLC35F1): rs281868; solute carrier family 12, member A9 (SLC12A9): rs314370; inactive UFm1-specific protease 1 (UFSP1): rs12666989; fatty acid desaturase 1 (FADS1): rs174547; CD34 antigen (CD34): rs2745967; or the like.

The SNPs affecting insulin resistance may be transcription factor 7-like 2 (TCF7L2): rs7903146; peroxisome proliferator-activated receptor (PPARG): rs1801282, rs6802898, rs2197423; potassium inwardly-rectifying channel J11 (KCNJ11): rs5219; insulin-like growth factor 2 mRNA binding protein 2 (IGF2BP2): rs4402960; hematopoietically expressed homeobox (HHEX): rs1111875; CDK5 regulatory subunit associated protein (CDKAL1): rs4712523; solute carrier family 30 member A8 (SLC30A8): rs13266634; wolframin (WFS1): rs10012946; cyclin dependent kinase inhibitor 2A (CDKN2A): rs2383208; potassium voltage-gated channel, KQT-like: KCNQ1: rs2237892; melatonin receptor 1B (MTNR1B): rs1387153; or the like.

As a third research design, the citizen science effort can carry out personality research by performing cognitive psychological research or social psychological research that tests various psychological hypotheses related to personality of a person by using behavioral characteristics questionnaires, such as various psychological analysis questionnaires that have been used in the cognitive psychological field and the like, or actual behavioral data. By combining the psychological data with the personal genome information, research can be carried out to explore relativity between cognitive characteristics (mental performance) or social intelligence and genes. The present embodiment can, for example, test the possibility that the genetic variation is related to the cognitive characteristics (optimism, empathy, extraversion, and altruism) of the social intelligence. The present embodiment can also test whether the social intelligence skills are improved through the intervention research.

The self-tracking data useful in the personality research may be as explained below. Of pieces of the phenotype data, the phenotypes of optimism, empathy, extraversion, and altruism may be evaluated using a widely recognized online research tool.

For example, as general personal type indicators, those from a Big Five personality test (openness, extraversion, agreeableness, conscientiousness, and neuroticism) with 44 questions (mandatory), a Revised NEO Personality Inventory (NEO-PI-R) test with 300 questions (optional), or the like may be used.

Of evaluations of empathy, an evaluation of empathy by self-reporting may be made using an interpersonal reactivity index (IRI) test with 28 questions (mandatory), an empathy quotient test (Baron-Cohen) with 60 questions (optional), or the like. An evaluation of behavioral empathy may be made using reading of mental states from eyes (Baron-Cohen) (optional), an audio/video empathy test, reading of mind in films (Baron-Cohen) (optional), reading of mind from voice (Baron-Cohen) (optional), or the like. An evaluation of optimism may be made using a revised life orientation test with 10 questions (mandatory), or the like.

An evaluation of extraversion may be made using the Big Five personality test (openness, extraversion, agreeableness, conscientiousness, and neuroticism) with 44 questions (mandatory), or the like. An evaluation of altruism may be made using the Revised NEO Personality Inventory (NEO-PI-R) test (Section A3) with 10 questions (mandatory), or the like.

The genetic data related to these personality research activities may be as explained below. The investigation may be made on at least three of the following intragenic polymorphisms that are suggested to be related to optimism, empathy, extraversion, or altruism. The SNPs related to personality may be oxytocin receptor (OXTR): rs53576; dopamine D2 receptor/ankyrin repeat and kinase domain containing 1 (ANKK1): rs1800497; catechol-O-methyltransferase (COMT): rs4680 (Val158Met); corticotropin-releasing hormone receptor 1 (CRHR1); or the like.

Figure 46:
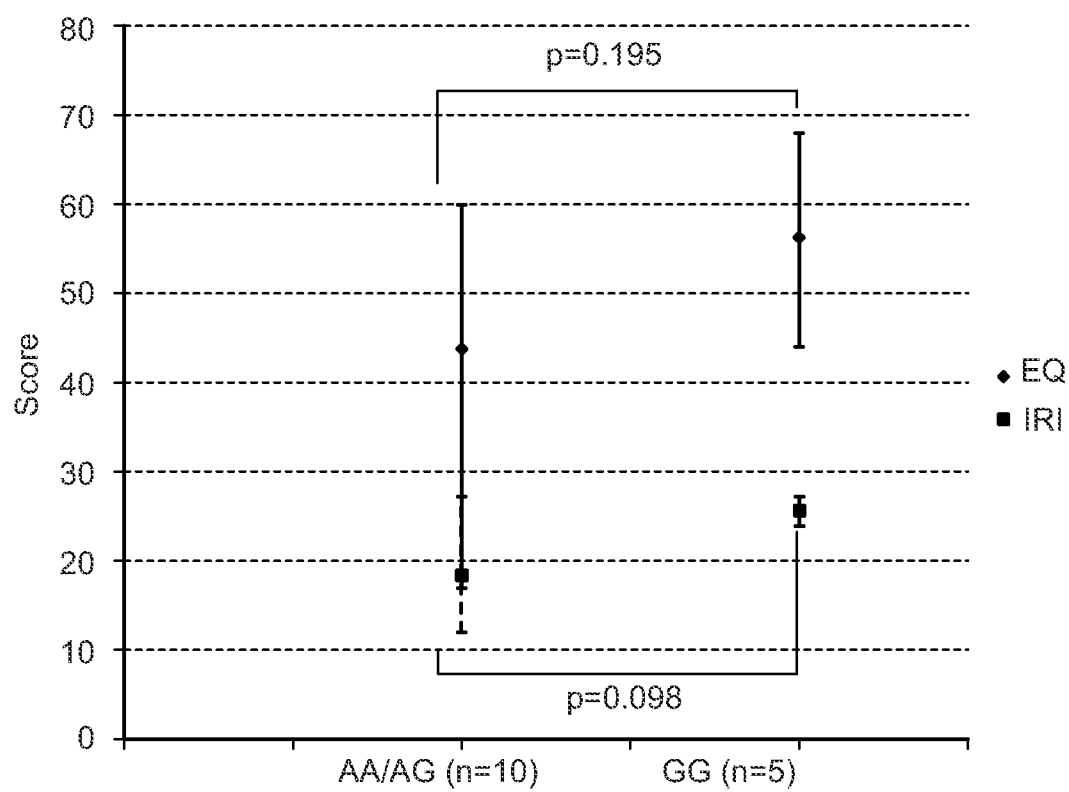
FIG. 46 is a diagram of an example of relations of variation of oxytocin receptor (OXTR) gene polymorphism with results of emotional quotient (EQ) tests and interpersonal reactivity index (IRI) tests according to the embodiment.

An example of citizen science about personality and genes (social intelligence) according to the present embodiment will be explained with reference to FIG. 46. FIG. 46 is a diagram of an example of relations of variation of OXTR gene polymorphism with results of emotional quotient (EQ) tests and IRI tests according to the present embodiment.

In the citizen science effort (personality discovery) about personality and genes of the user according to the present embodiment, a hypothesis was first set up such that the genetic variation may be related to the cognitive characteristics (optimism, empathy, extraversion, and altruism) of the social intelligence. The hypothesis was tested.

The attempt to explore the relativity between the cognitive characteristics (mental performance) or the social intelligence and genes is a latest new field of testing. In recent years, several interesting reports have been made on the relation between personal genetic profiles and social intelligence. The present embodiment tests these latest reports about genetic characteristics of social intelligence based on genetic data and replies to questionnaires (phenotypes). The present embodiment may attempt to test whether the social intelligence skills are improved through the intervention research.

The present embodiment may investigate at least three of the following intragenic polymorphisms that are suggested to be related to optimism, empathy, extraversion, or altruism, as the genotype data. Specifically, each of the intragenic polymorphisms may be oxytocin receptor (OXTR): rs53576; dopamine D2 receptor/ankyrin repeat and kinase domain containing 1 (ANKK1): rs1800497; catechol-O-methyltransferase (COMT): rs4680 (Val158Met); corticotropin-releasing hormone receptor 1 (CRHR1); or the like.

The present embodiment may use one of the following widely recognized online research tools for evaluating the phenotype of optimism, empathy, extraversion, or altruism. Specifically, the online research tool may be general personal type indicators, the Big Five personality test (openness, extraversion, agreeableness, conscientiousness, and neuroticism) with 44 questions (mandatory), the Revised NEO Personality Inventory (NEO-PI-R) test with 300 questions (optional), or the like.

In the present embodiment, the interpersonal reactivity index (IRI) test with 28 questions (mandatory), the empathy quotient test (Baron-Cohen) with 60 questions (optional), or the like may be used as a test for empathy by self-reporting among tests for empathy. The reading of mental states from eyes (Baron-Cohen) (optional), or the like may be used as a test for the behavioral empathy. The reading of mind in films (Baron-Cohen) (optional), the reading of mind from voice (Baron-Cohen) (optional), or the like may be used as an audio/video empathy test.

In the present embodiment, the revised life orientation test with 10 questions (mandatory), or the like may be used as a test for optimism. The Big Five personality test (openness, extraversion, agreeableness, conscientiousness, and neuroticism) with 44 questions (mandatory), or the like may be used as a test for extraversion. The Revised NEO Personality Inventory (NEO-PI-R) test (Section A3) with 10 questions (mandatory), or the like may be used as a test for altruism.

The method for carrying out these tests may be such that the research is performed as a participatory cohort research by crowdsourcing (a method in which the general public are asked for performing research via the Internet). These tests may be performed on a voluntary participation and continuing basis, and 100 or more participants may be recruited for a first stage research. The recruitment of members required for the research and the research for these tests may be performed in the Genomera Community via the Internet. The participants may first agree to the informed consent, then agree to share the genotypes of variants to be surveyed, and reply to the online survey. Individual feedback (that is, such as provision of the personality prediction information about the personality of the user acquired by the characteristic information acquiring unit 102c) is given to each of the participants, who, if he or she wishes, can apply for participation in the intervention research for building the social intelligence skills.

In the participatory cohort research through crowdsourcing, the characteristic information acquiring unit 102c may examine whether the result of the prior research is reproduced, as a first phase at the test stage. Then, as a second phase, the characteristic information acquiring unit 102c may analyze (examine) through the intervention research whether a causal relation holds in the relativity between genetic variation found in the first phase and social intelligence characteristics. Specifically, the characteristic information acquiring unit 102c may systematically analyze (examine) whether evaluation values of improvement in the social intelligence skills using mobile applications or the like differ between a group where the genetic variation has occurred and a group where no genetic variation has occurred, and may acquire the personality prediction information.

As an example of analysis results of the citizen science effort about personality and genes according to the present embodiment, FIG. 46 depicts the relations of variation of OXTR gene polymorphism (SNP: rs53576) with results of the emotional quotient (EQ) tests and the IRI tests given to 15 participants. No definite conclusion can be made because this citizen science project does not have sufficiently many participants. However, as shown in FIG. 46, data has been obtained that shows that a group having GG gene polymorphism yields higher results of the EQ and the IRI tests on average than those of a group with AG/AA type. This suggests that a person who has two G alleles in the above-mentioned OXTR gene polymorphism can be higher in empathy and optimism than a person who does not have two G alleles. The present embodiment may perform the intervention research about improvement in the social intelligence skills described in the research plan mentioned above. Specifically, the present embodiment may test whether the results of the EQ and the IRI tests of the user are improved by virtual coaching, using a computer program with which the virtual coaching can be performed through an interactive chat with the user.

Other Embodiments

Embodiments of the present invention have been described above, and the present invention can be implemented by various different embodiments within the scope of the technical idea described in the claims in addition to the above-described embodiments.

For example, while examples have been given on the cases where the personal genome information environment providing device 100 performs the processing in a stand-alone mode, the personal genome information environment providing device 100 may perform the processing in response to a request from a client terminal (a housing other than the personal genome information environment providing device 100) and return the processing results to the client terminal.

Moreover, among the steps of the processing described in the embodiments, all or part of the steps of the processing described as automatic processing may be performed manually and all or part of the steps of the processing described as manual processing may be performed automatically by well-known methods.

In addition, the processing procedures, the control procedures, the specific names, the information including registered data of each processing and parameters, such as retrieval conditions, the screen examples, and the database configurations, described in the literature and drawings above may be modified unless otherwise indicated.

Furthermore, the components of the personal genome information environment providing device 100 illustrated in the drawings are formed on the basis of functional concept, and need not be configured physically the same as those illustrated in the drawings.

For example, all or any part of the processing functions that the devices in the personal genome information environment providing device 100 have, and particularly each processing function performed by the control unit 102, may be implemented by a central processing unit (CPU) and a computer program interpreted and executed by the CPU, or may be implemented as hardware by wired logic. The computer program is recorded in a non-transitory and computer-readable recording medium including programmed instructions for causing a computer to execute the method in the present invention to be described later, and is mechanically read into the personal genome information environment providing device 100 as necessary. Specifically, the storage unit 106, such as a ROM and a hard disk drive (HDD), or the like records a computer program for providing instructions to the CPU in cooperation with the operating system (OS) and for executing various types of processing. This computer program is executed by being loaded into a RAM and configures the control unit in cooperation with the CPU.

Moreover, this computer program may be stored in an application program server that is connected to the personal genome information environment providing device 100 via any desirable network 300, and all or part thereof may be downloaded as necessary.

Furthermore, the program according to the present invention may be stored in a computer-readable recording medium and may be configured as a program product. The "recording medium" includes any "portable physical medium", such as a memory card, a USB memory, an SD card, a flexible disk, a magneto-optical disk, a ROM, an EPROM, an EEPROM, a CD-ROM, an MO, a DVD, and a Blu-ray (registered mark) disc.

Moreover, the "program" refers to a data processing method written in any language and any description method, and is not limited to a specific format, such as source codes and binary codes. The "program" is not necessarily configured unitarily and includes a program constituted in a dispersed manner as a plurality of modules and libraries and a program that implements its functions in cooperation with a different program represented by an OS. Well-known configurations and procedures can be used for the specific configuration and reading procedure for reading a recording medium, the installation procedure after reading a recording medium, and the like in each device illustrated in the embodiments.

Various databases and the like (the habit information database 106a, the biological signal information database 106b, and the personal genome information database 106c) stored in the storage unit 106 are each a storage unit, examples of which include memory devices, such as a RAM and a ROM, fixed disk drives, such as a hard disk, a flexible disk, and an optical disc, and store various computer programs, tables, databases, files for web pages, and the like that are used for various types of processing or providing websites.

Moreover, the personal genome information environment providing device 100 may be configured as an information processing apparatus, such as a well-known desktop or laptop personal computer, mobile terminals such as a mobile phone, a smartphone, a PHS, and a PDA, and a workstation, or may be configured by connecting any desirable peripheral device to the information processing apparatus. Moreover, the personal genome information environment providing device 100 may be implemented by installing software (including computer programs and data) that causes the information processing apparatus to execute the method of the present invention.

Furthermore, specific forms of distribution/integration of the devices are not limited to those illustrated in the drawings, and all or a part thereof can be configured by functionally or physically distributing or integrating them in any desired unit according to, for example, various additions, or according to functional loads. In other words, the above-described embodiments may be implemented by combining them in any desired manner, or the embodiments may be selectively performed.

Summary of Present Embodiments

The technique proposed in the present embodiments differs from those of conventional coaching or idea generation support systems in presenting awareness, idea generation support, a mental model, and the like to the user.

Most conventional self-development programs and coaching systems have been empirically systematized, and are not based on accumulated scientific data. Specifically, previously performed coaching and the like have been automated in the systems that support coaching, but the systems do not encourage the user to discover the behavioral characteristics or gain new awareness based on scientific evidence by accumulating data, such as habit records, biological information records, and genetic information.

In contrast, by using not only the subjective question-and-answer evaluation of the user's own state, but also the function of integrating the information such as the biological signals (such as brain waves, heart rates, sleep waveforms, blood sugar levels, and amounts of exercises) obtained by simple self-tracking, and displaying the signals in a chart form as time series events, the technique (such as the processing at Steps SC-4 to SC-6 in FIG. 6) proposed in the present embodiments can help the user to interactively discover the user's own behavioral characteristics in a self-discovering manner and to find a self-development method and a target suited to the user through accumulation of the scientific evidence based on the data. By employing the genetic information of a person, the technique proposed in the present embodiments can further help the person to discover behavioral characteristics or new awareness taking into consideration features that can be possessed only by the person.

Hence, according to the technique proposed in the present embodiments, unlike the conventional medical diagnosis systems in which a computer explicitly presents diagnostic results, the intelligent agent engine 102f interactively presents the data previously accumulated by the user and opinions of a person or people trusted by the user, along with the scientific evidence, so that the user can be more conscious of more actively discovering the user's own state, thinking, and behavioral characteristics in a self-discovering manner instead of passively receiving the results. According to the technique proposed in the present embodiments, the intelligent agent engine 102f can further help the user to interactively ask and answer the user's own questions about the user's own previous record management data and scientific knowledge, so that the user can naturally acquire a habit of self-discovery. While hardly any conventional coaching systems using biofeedback or the like use any personal genetic information, the technique proposed in the present embodiments can help the user to discover behavioral characteristics or new awareness taking the personal features into consideration by using the personal genome knowledge database 106c. While conventional genetic information systems mainly aim at medical diagnosis, the technique proposed in the present embodiments collects data for finding correlations between thinking, sensation, and behavioral characteristics, and genes by integrating the user's own daily behavioral characteristics stored in the habit record database 106a with the personal genome information by using the information integrating engine 102d. Thus, the technique proposed in the present embodiments can cause the user to gain new awareness, and can collect data for a new scientific discovery using personal genome information in the fields of cognitive science and behavioral science beyond the border of conventional medical research.

The technique proposed in the present embodiments differs from those of the conventional personal genome systems and conventional medical diagnosis systems in presenting non-medical personal genome applications or the like that can take racial variations into account. In other words, the technique proposed in the present embodiments builds a more reliable prediction model that takes racial variations into account.

The conventional personal genome systems are intended for sick people and focused on preventive medical care, and non-medical applications have hardly been assumed. The conventional personal genome systems mainly compare whether there is a significant difference in terms of genetic statistics between patients reported to medical institutions and healthy people, and search for genes related to disorders. While personal genomes and physical constitutions (such as prediction of disease risk or drug efficacy) are greatly influenced by racial variations, no calculation model has been established. Research has hardly been conducted to explore the relativity between personal genomes and behavioral characteristics, sensory characteristics, or thinking characteristics.

The technique (such as the processing at Steps SC-3 to SC-6 in FIG. 6) proposed in the present embodiments, however, introduces a mechanism that allows general healthy people to easily accumulate the personal genome information and the daily self-tracking data so as to be able to find the relativity between the behavioral characteristics and the genes of the healthy people, which has not been assumed before. The technique proposed in the present embodiments provides a framework to find new scientific knowledge that has not been found before from systems intended for sick people. The technique proposed in the present embodiments can provide a highly reliable prediction model by performing analysis on the stratified data from the same race and performing the risk estimation according to racial variations.

As a result, the technique proposed in the present embodiments can provide the function to integrate the personal genome data with the self-tracking data and the function to acquire knowledge by data mining to the healthy people who have not been given the personal genome information before. This can allow the technique proposed in the present embodiments to find new scientific knowledge that has not been found before from the systems intended for sick people. Specifically, the technique proposed in the present embodiments can provide information on the search for related genes, in particular, on the relativity between sensation, thinking, or behavioral characteristics, and genes in non-medical fields that have hardly been covered before. While risk prediction models of the conventional personal genome systems are mainly based on disease-related analysis results for Caucasians, the racial difference actually has a great influence on the disease risk. For example, it is pointed out that Europeans and Americans greatly differ from Japanese in pathogenic mechanism and risk of diabetes. The technique proposed in the present embodiments can apply a disease risk prediction model that takes the influence of racial variations into account by using the function to acquire knowledge by data mining, and thereby can predict the disease risk that takes the racial variations into account and is applicable to Japanese and others.

The technique proposed in the present embodiments differs from those of conventional biological signal data acquiring systems, life logs, and participatory community support systems in providing simple self-tracking. Specifically, the technique proposed in the present embodiments analyzes the "participatory" scientific discovery framework that completely differs from frameworks of conventional genetic exploratory research, and establishes a new personal genome information environment.

To acquire biological signal data, general people have needed a medical institution or a special environment and instruments, and thereby have needed a large expense. To acquire scientific knowledge about health, general people have needed to obtain specialized knowledge from a medical specialist or the like, which has been difficult to be put into action.

The technique (such as the processing at Steps SC-2 and SC-4 in FIG. 6) proposed in the present embodiments, however, introduces a mechanism that uses mobile terminals to easily acquire various pieces of biological signal data (such as brain waves, heartbeats, and sleep waveforms) that have so far been obtained at medical institutions or in special environments, then integrates the various pieces of biological signal data with subjective data and scientific knowledge, and displays the result in an easily understandable manner. As a result, the technique proposed in the present embodiments allows general people to easily record their own health information or behavioral characteristic information by performing self-tracking of the information, and to customize general knowledge about medical science and health by combining the self-tracking data of the user with genetic information that can be possessed only by the user. In other words, by actively using the personal genetic information, the technique proposed in the present embodiments can accumulate scientific data, and thereby can rediscover and retest programs and knowledge that have so far been empirically systematized.

As a result, by using the information integrating function for integrating the self-tracking data, the technique proposed in the present embodiments can use the mobile terminals to easily acquire the biological signal data that has so far been used at medical institutions and the like, and can integrate the biological signal data. This allows general people to check the health condition and the mental and physical state of themselves, and acquire scientific knowledge about health, without medical expert knowledge. By using the function of expressing emotions and events as the mental and physical state symbols and recording the states, the technique proposed in the present embodiments can associate the mental and physical state symbols, the biological signals, and the event information with one another. This enables the integrated display of the mental and physical state, the biological signals, and the time series events, which is not possible by conventional technologies. Thus, a person can be encouraged to conduct the interactive self-discovery.

The technique proposed in the present embodiments differs from those of conventional personal adaptive systems and community support systems in allowing a policy statement suited to the user to be selected.

Many people have hesitated so far to share personal information including genetic information in a community for scientific discovery from the viewpoint of privacy protection. Only little information has been available for making judgment on risk and benefit of participating in a participatory project by sharing information, so that people have had a sense of resistance to actively participating in citizen science projects.

The technique (such as the processing at Step SC-6 in FIG. 6) proposed in the present embodiments, however, makes an investigation on what many people feel about personal genomes, and classifies patterns of risk and benefit based on the result of analysis of the tendency. As a result, the technique proposed in the present embodiments can enhance the sense of participation in the community by presenting a participation policy suited to each person. By defining the scope of information disclosure and protecting the privacy information according to the policy statement suited to each person, the technique proposed in the present embodiments allows each person to participate in the community with a higher sense of security than before.

As a result, the technique proposed in the present embodiments can present the participation policy suited to the person to the community by making the investigation on what the person feels about use of the personal genome information, and classifying the behavioral pattern of the person through analysis of risk and benefit, so that the person can participate in the community with a higher sense of security.

Figure 47:
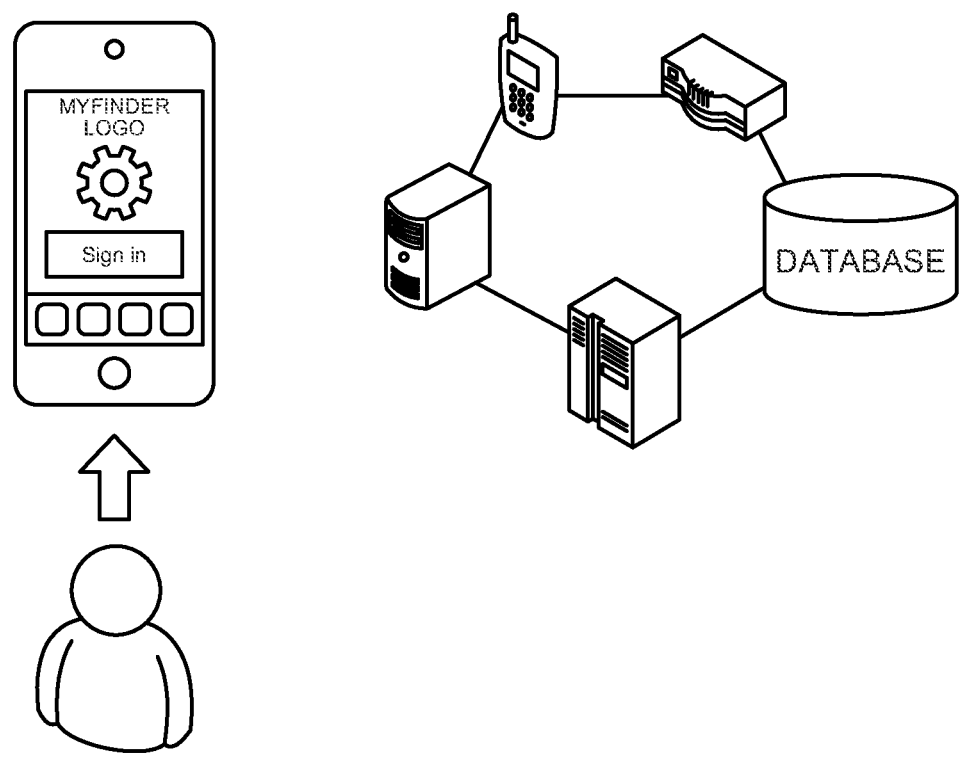
FIG. 47 is a diagram of an example of presentation processing of a participation policy according to the embodiment.

An example of the presentation processing of the participation policy according to the present embodiment will be explained with reference to FIG. 47. FIG. 47 is a diagram of the example of the presentation processing of the participation policy according to the present embodiment.

As shown in FIG. 47, in the presentation processing of the participation policy according to the present embodiment, an investigation is made on what many people who have logged in to the system feel about personal genomes, and a crawler is always started to accumulate and analyze the user information; and based on the result of the analysis, patterns about risk and benefit are classified, and a policy statement suited to each person is presented.

The technique proposed in the present embodiment differs from those of conventional self-tracking systems in feedback of habituation.

Unless a person is highly motivated, such as having a substantially high sense of health and curiosity, keeping the person's own daily behavioral records has so far involved high cost even if the self-tracking is easily operated.

However, according to the technique (such as the processing at Steps SC-1 and SC-6 in FIG. 6) proposed in the present embodiments, based on the analysis result of social statistical research and social psychological knowledge about personal genomes, the system analyzes the behavioral characteristic pattern of the person, and performs interactive feedback according to the motivation and ability of the person at appropriate timing, whereby the system can raise the motivation of the person, and can provide coaching support for physically and mentally healthy lifestyle habits suited to the person.

According to the technique proposed in the present embodiments, various icons are displayed on the dialogue board on a mobile terminal, and icons determined by the system to have high priority are displayed in a large size with a message. Using a function for animation of the positions and sizes of the icons caused by mouse operations of the user can interactively encourage the user to gain awareness, and can facilitate improvement in motivation and a sense of participation.

Figure 48:
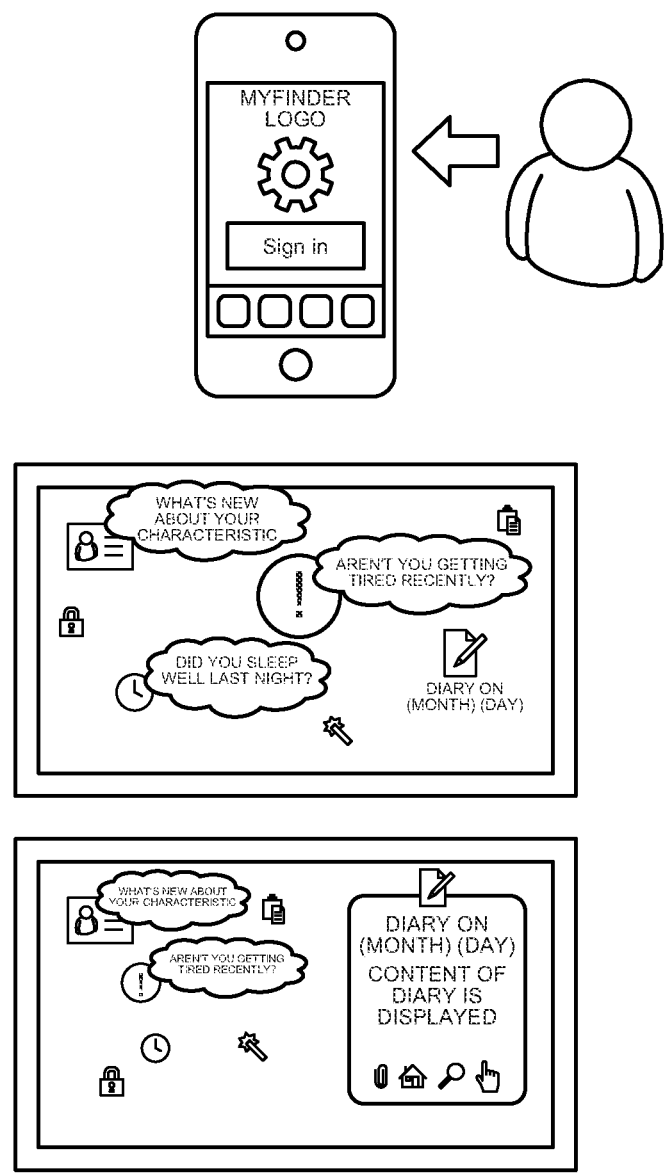
FIG. 48 is a diagram of an example of a dialogue board according to the embodiment.

An example of the dialogue board according to the present embodiment will be explained with reference to FIG. 48. FIG. 48 is a diagram of the example of the dialogue board according to the present embodiment.

As shown in FIG. 48, the login of the user to the system displays various icons on the dialogue board according to the present embodiment. Icons determined by the system to have high priority are displayed in a large size with a message. Mouse operations of the user animate the positions and sizes of the icons.

The technique proposed in the present embodiments differs from those of conventional support systems for people with developmental disorder.

People with developmental disorder differ from others in sensory and behavioral characteristics, and thereby, their unconscious behavior has been received with a feeling of strangeness by people around. This has often caused the people with developmental disorder to feel social stress and pain. The people with developmental disorder cannot also find the cause of the feeling of strangeness held by the people around, and in the circumstances where the developmental disorder is little understood by the people around, the people with developmental disorder have often weakened their own self-respect and felt psychological stress in organizations. While treatment, including drug treatment, is applied to people with developmental disorder, diagnosis of developmental disorder is difficult. In addition, the drug treatment is mainly symptomatic treatment, and side-effects or erroneous diagnoses have occurred more than a few times. Counseling and job coaching that support independence of people with developmental disorder have started, but lack human resources who can provide expert counseling. Sufficient social understanding to social participation of people with developmental disorder has not been acquired.

Using the technique (such as the processing at Steps SC-3, SC-5, and SC-6 in FIG. 6) proposed in the present embodiments allows people with developmental disorder to expand the scope of themselves recognized by themselves and themselves seen by other people by knowing the differences between their own behavioral, sensory, and thinking characteristics and other people's behavioral, sensory, and thinking characteristics. Specifically, using the technique proposed in the present embodiments causes the people with developmental disorder to broaden the Open quadrant in a Johari window (a graphic model of awareness in interpersonal relations) in communication psychology; and using the technique proposed in the present embodiments allows the people around to become aware of differences in behavioral, sensory, and thinking characteristics between people with developmental disorder and people without developmental disorder, and thereby to gain an opportunity to deepen mutual understanding by becoming aware of prejudice and a sense of discrimination that might have unconsciously arisen. Using the technique proposed in the present embodiments allows the people with developmental disorder and the people without developmental disorder to mutually recognize the difference in individuality and enhance the sense of respect for the individuality. The technique proposed in the present embodiments can also gather scientific data for use in diagnosis and treatment of the developmental disorder.

Figure 49:
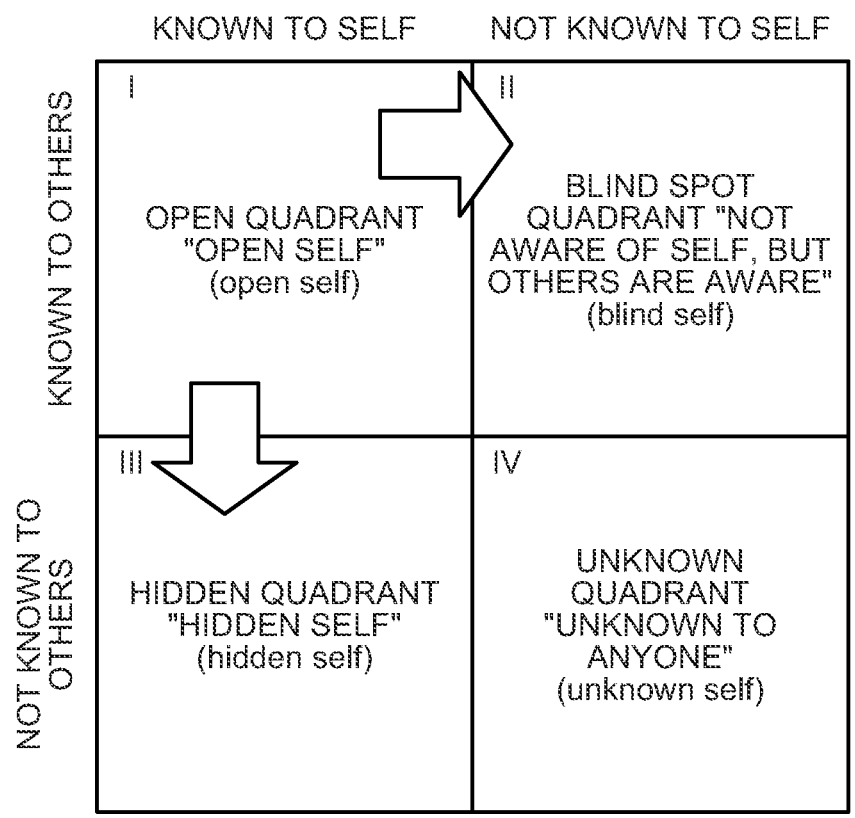
FIG. 49 is a diagram of an example of a Johari window in the embodiment.

An example of the Johari window in the present embodiment will be explained with reference to FIG. 49. FIG. 49 is a diagram of the example of the Johari window in the present embodiment.

As shown in FIG. 49, the Johari window in the present embodiment is a graphic model of awareness in interpersonal relations that consists of Open quadrant for the open self, Hidden quadrant for the hidden self, Blind Spot quadrant for the self who is not aware of oneself but is seen from others, and Unknown quadrant for the self yet to be known to anyone.

The technique proposed in the present embodiment can gather the scientific data for use in diagnosis and treatment of the developmental disorder by analyzing the relativity between behavior, sensation, and thinking characteristics and the difference in genes among individuals, and building the personal genome knowledge database 106c that stores genetic information and phenotype information related to the developmental disorder in a corresponding manner. The technique proposed in the present embodiment differs from those of conventional systems for visualizing and sharing sensory information.

Interpersonal communications have conventionally been established under the consensus that sensibility, such as how colors are seen and how time is felt, is common among all people, and it has not been assumed that such sensibility differs between individuals. There have been only limited ways to express such sensory information and collect the information as scientific data. Little consideration has been given to a perception that colors influence how a person feels time, or a possibility that stimuli by colors can influence genes in the biological clock.

The technique (such as the processing at Steps SC-5 and SC-6 in FIG. 6) proposed in the present embodiments can, however, visualize the sensory information as cognitive data about reactions to stimuli, so that each person can know the differences in sensibility. According to the technique proposed in the present embodiments, each person can imagine other people's feeling based on the visualized sensory information, and can have a simulated experience. The technique proposed in the present embodiments can collect scientific data useful for clarification of the evolution of human cognitive mechanisms by investigating the correlation between the sensory information and the differences in genes.

The technique proposed in the present embodiments visualizes the sensory information as the cognitive data about reactions to stimuli, and visualizes the differences in sensibility between individuals, thereby allowing each person to understand the differences in sensibility from other people.

Specifically, the technique proposed in the present embodiments can provide an intelligent information environment that promotes awareness by combining any one, some, or all of the life log, the habit records, and the electroencephalogram (sleep) analysis with the personal genome information including the genetic information. The technique proposed in the present embodiments can provide an intelligent information environment that promotes scientific discoveries by performing data mining on the genetic information and the behavioral records in the life log that have been mainly gathered from individuals. The technique proposed in the present embodiments can provide reliable predictions of diseases and drug efficacy. As a result, the technique proposed in the present embodiments can reliably predict discoveries of talent or ability, and can provide an intelligent information environment that uses the personal genome information for discovering personality (individuality), education, or career planning.

INDUSTRIAL APPLICABILITY

As explained above in detail, the present invention can provide the personal genome information environment providing device, the personal genome information environment providing method, and the computer program that can achieve the information providing environment in which, by employing the personal genome information serving as scientific data into the personal lifestyle of a person beyond the boundary of the medical field, the person can heuristically find awareness or a way of life suited to the person, can then use the finding for competency development, improvement in human relations, or the like, and can find a mentally and physically healthy way of life natural to the person. The present invention is highly useful in the field of healthcare industry in particular.

EXPLANATIONS OF LETTERS OR NUMERALS

100 Personal genome information environment providing device (personal genome information environment)
102 Control unit
102a Self-tracking information acquiring unit (information integrating engine)
102b Personal genome information acquiring unit
102c Characteristic information acquiring unit
102d Information integrating unit (information integrating engine)
102e Data mining unit (data mining engine)
102f Information outputting unit (intelligent agent engine)
104 Communication control interface unit
106 Storage unit
106a Habit information database (habit record database)
106b Biological signal information database (physical information record database)
106c Personal genome information database (personal genome knowledge database)
108 Input/output control interface unit
112 Monitoring device unit (monitoring device group)
114 Display unit
116 Audio output unit
118 Input unit
200 External system
300 Network

The invention claimed is:

1. A personal genome information environment providing device for increasing sleep quality of a user comprising:
a monitoring device unit that performs self-tracking of habit information and biological signal information of a user and comprising at least one mobile device configured to measure exercise data, brain waves, heartbeat, body weight, blood sugar level, or sleep data of the user from which the biological information is obtained, an output unit, a control unit, and a storage unit, wherein
the storage unit includes:
a personal genome information storage unit that stores personal genome information associating genetic information of the user with genetic knowledge information, and
the control unit includes:
a self-tracking information acquiring unit that acquires self-tracking information obtained by integrating the habit information and the obtained biological signal information that are detected by the monitoring device unit comprising the at least one mobile device;
a characteristic information acquiring unit that acquires characteristic information about characteristics of the user based on the personal genome information stored in the personal genome information storage unit and the self-tracking information acquired by the self-tracking information acquiring unit, wherein the characteristic information includes interactive knowledge information, and wherein the characteristic information acquiring unit includes:
an information integrating unit that acquires integrated information obtained by integrating the personal genome information stored in the personal genome information storage unit and the self-tracking information acquired by the self-tracking information acquiring unit to derive an indicator that defines a user characteristic; and
a data mining unit that acquires interactive knowledge information comprising identifying a relationship between a user characteristic and a biological signal and/or self-tracking information by performing data mining on the integrated information acquired by the information integrating unit, and
an information outputting unit which outputs, via the output unit, the interactive knowledge information acquired by the data mining unit;
the information outputting unit outputs, via the output unit, the characteristic information acquired by the characteristic information acquiring unit, wherein the characteristic information comprises an index that defines the user's quality of sleep; and
wherein the device presents a time-series change of the index to the user and present change of behavior and change of habit advice to the user for increasing sleep quality of the user.

2. The personal genome information environment providing device according to claim 1, wherein the characteristic information includes any one, some, or all of risk prediction information on genetic diseases, drug efficacy prediction information, and personality prediction information.

3. The personal genome information environment providing device according to claim 1, wherein
the interactive knowledge information includes correlation information on a correlation between the genetic information and the self-tracking information, and
the data mining unit acquires the interactive knowledge information by performing the data mining using genetic statistical analysis on the integrated information acquired by the information integrating unit.

4. The personal genome information environment providing device according to claim 1, wherein the habit information is information based on any one, some, or all of meals, sleep, exercises, diaries, behavioral records, and behavioral characteristics questionnaires.

5. The personal genome information environment providing device according to claim 1, wherein the biological signal information is information based on sleep waveforms.

6. A personal genome information environment providing method to increase sleep quality of a user executed by a personal genome information environment providing device that includes:
a monitoring device unit that performs self-tracking of habit information and biological signal information of a user and comprising at least one mobile device configured to measure sleep data of the user from which the biological information is obtained, an output unit, a control unit, and a storage unit, wherein
the storage unit includes:
a personal genome information storage unit that stores personal genome information associating genetic information of the user with genetic knowledge information,
the method executed by the control unit comprising:
a self-tracking information acquiring step of acquiring self-tracking information obtained by integrating the habit information and the biological signal information that are detected by the monitoring device unit comprising the at least one mobile device;
a characteristic information acquiring step of acquiring characteristic information about characteristics of the user based on the personal genome information stored in the personal genome information storage unit and the self-tracking information acquired at the self-tracking information acquiring step wherein the characteristic information acquiring step uses a characteristic information acquiring unit which includes:

an information integrating unit that acquires integrated information obtained by integrating the personal genome information stored in the personal genome information storage unit and the self-tracking information acquired by the self-tracking information acquiring unit and which identifies any decrease in quality of sleep of the user; and a data mining unit that acquires interactive knowledge information by performing data mining on the integrated information acquired by the information integrating unit, and which identifies behavioral indicators that relate to quality of sleep of the user by performing regression analysis on sleep scores, habit information, or the behavioral information, an information outputting unit which outputs, via the output unit, the interactive knowledge information acquired by the data mining unit; and an information outputting step of outputting, via the output unit, the characteristic information acquired at the characteristic information acquiring step, wherein the information output comprises an index that defines the user's quality of sleep; and a step of the device presenting a time-series change of the index to the user and present change of behavior and change of habit advice to the user so as to increase sleep quality of the user.

7. The personal genome information environment providing method according to claim 6, wherein the sleep data obtained comprises a temporal change in: wakeup time, level 1 sleeping hours (shallow sleep), level 2 sleeping hours (deep sleep), or waking hours.

8. The personal genome information environment providing method according to claim 6, wherein the characteristic information further includes any one, some, or all of risk prediction information on genetic diseases, drug efficacy prediction information, and personality prediction information.

9. The personal genome information environment providing method according to claim 7, wherein
the interactive knowledge information includes correlation information on a correlation between the genetic information and the self-tracking information, and
at the data mining step, the interactive knowledge information is acquired by performing the data mining using genetic statistical analysis on the integrated information generated at the information integrating step.

10. The personal genome information environment providing method according to claim 6, wherein the habit information is information further based on any one, some, or all of meals, exercises, diaries, behavioral records, and behavioral characteristics questionnaires.

11. The personal genome information environment providing method according to claim 6, wherein the biological signal information also comprises information based on any one, some, or all of brain waves, heart rates, sleep waveforms, blood sugar levels, body weights, and amounts of exercises.

12. A computer program product having a non-transitory tangible computer readable medium including programmed instructions for causing, when executed by a personal genome information environment providing device for increasing sleep quality of a user that includes a monitoring device unit that performs self-tracking of habit information and biological signal information of a user and comprises at least one mobile device configured to measure sleep data of the user from which the biological information is obtained, an output unit, a control unit, and a storage unit including a personal genome information storage unit that stores personal genome information associating genetic information of the user with genetic knowledge information, the personal genome information environment providing device to perform a personal genome information environment providing method comprising:

a self-tracking information acquiring step of acquiring self-tracking information obtained by integrating the habit information and the biological signal information that are detected by the monitoring device unit;

a characteristic information acquiring step of acquiring characteristic information about characteristics of the user, wherein the characteristic information does not comprise drug efficacy prediction, based on the personal genome information stored in the personal genome information storage unit and the self-tracking information acquired at the self-tracking information acquiring step, wherein the characteristic information acquiring step uses a characteristic information acquiring unit which includes:

an information integrating unit that acquires integrated information obtained by integrating the personal genome information stored in the personal genome information storage unit and the self-tracking information acquired by the self-tracking information acquiring unit and which identifies any decrease in quality of sleep of the user; and a data mining unit that acquires interactive knowledge information by performing data mining on the integrated information acquired by the information integrating unit, and which identifies behavioral indicators that relate to quality of sleep of the user by performing regression analysis on sleep scores, habit information, or the behavioral information, and an information outputting unit which outputs, via the output unit, the interactive knowledge information acquired by the data mining unit; and an information outputting step of outputting, via the output unit, the characteristic information acquired at the characteristic information acquiring step, wherein the information output comprises an index that defines the user's quality of sleep;

a step of the device presenting a time-series change of the index to the user; and presenting change of behavior and change of habit advice to the user so as to increase sleep quality of the user.

13. The computer program product according to claim 12, wherein the sleep data obtained comprises a temporal change in: wakeup time, level 1 sleeping hours (shallow sleep), level 2 sleeping hours (deep sleep), or waking hours.

14. The computer program product according to claim 12, wherein the characteristic information further includes any one, some, or all of risk prediction information on genetic diseases, and personality prediction information.

15. The computer program product according to claim 13, wherein
the interactive knowledge information includes correlation information on a correlation between the genetic information and the self-tracking information, and
at the data mining step, the interactive knowledge information is acquired by performing the data mining using genetic statistical analysis on the integrated information generated at the information integrating step.

16. The computer program product according to claim 12, wherein the habit information is information based on any one, some, or all of meals, exercises, diaries, behavioral records, and behavioral characteristics questionnaires.

17. The computer program product according to claim 12, wherein the biological signal information also comprises information based on any one, some, or all of brain waves, heart rates, sleep waveforms, blood sugar levels, body weights, and amounts of exercises.

* * * * *